US010266586B2

(12) United States Patent
James

(10) Patent No.: US 10,266,586 B2

(45) Date of Patent: Apr. 23, 2019

(54) TARGETING CLPTM1L FOR TREATMENT AND PREVENTION OF CANCER

(71) Applicant: THE MEDICAL COLLEGE OF WISCONSIN, INC., Milwaukee, WI (US)

(72) Inventor: Michael A. James, Big Bend, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 0 days.

(21) Appl. No.: 15/111,445

(22) PCT Filed: Jan. 6, 2015

(86) PCT No.: PCT/US2015/010219

§ 371 (c)(1),
(2) Date: Jul. 13, 2016

(87) PCT Pub. No.: WO2015/108719

PCT Pub. Date: Jul. 23, 2015

(65) Prior Publication Data

US 2016/0333083 A1 Nov. 17, 2016

Related U.S. Application Data

(60) Provisional application No. 61/927,330, filed on Jan. 14, 2014.

(51) Int. Cl.

| | |
|---|---|
| ***C07K 16/30*** | (2006.01) |
| ***A61K 39/395*** | (2006.01) |
| ***C07K 16/18*** | (2006.01) |
| *A61K 39/00* | (2006.01) |

(52) U.S. Cl.

CPC .............. *C07K 16/18* (2013.01); *C07K 16/30* (2013.01); *C07K 16/303* (2013.01); *C07K 16/3015* (2013.01); *C07K 16/3023* (2013.01); *C07K 16/3038* (2013.01); *C07K 16/3046* (2013.01); *C07K 16/3053* (2013.01); *C07K 16/3069* (2013.01); *A61K 39/395* (2013.01); *A61K 39/39558* (2013.01); *A61K 2039/505* (2013.01); *C07K 2317/34* (2013.01); *C07K 2317/73* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 4,816,567 A | 3/1989 | Cabilly et al. | |
| 5,229,275 A | 7/1993 | Goroff | |
| 5,545,806 A | 8/1996 | Lonberg et al. | |
| 5,545,807 A | 8/1996 | Surani et al. | |
| 5,567,610 A | 10/1996 | Borrebaeck et al. | |
| 5,569,825 A | 10/1996 | Lonberg et al. | |
| 5,591,669 A | 1/1997 | Rodriguez et al. | |
| 5,821,337 A | 10/1998 | Carter et al. | |
| 5,837,234 A | 11/1998 | Gentile et al. | |
| 5,869,046 A | 2/1999 | Presta et al. | |
| 5,969,108 A | 10/1999 | McCafferty et al. | |
| 6,300,064 B1 | 10/2001 | Knappik et al. | |
| 6,824,780 B1 | 11/2004 | Devaux et al. | |
| 7,396,920 B2 * | 7/2008 | Hemmings ........ | C07K 14/4702 536/23.1 |
| 2003/0198975 A1 * | 10/2003 | Azimzai ............ | C07K 14/4738 435/6.16 |

FOREIGN PATENT DOCUMENTS

| | | |
|---|---|---|
| JP | 2000-210089 A | 8/2000 |
| JP | 2004533829 A | 11/2004 |
| WO | 96/16673 | 6/1996 |
| WO | 97/17852 | 5/1997 |
| WO | 98/02463 | 1/1998 |
| WO | 2002097032 A2 | 12/2002 |

OTHER PUBLICATIONS

The International Search Report dated Mar. 30, 2015 for International Application No. PCT/US2015/010219.

Michael A. James et al: "Functional Characterization of CLPTMIL as a Lung Cancer Risk Candidate Gene in the 5p15.33 Locus", PLoS One, vol. 7, No. 6, Jun. 4, 2012 (Jun. 4, 2012), p. e36116. XP055175210; DOI: 10.1371/Journal.pone.0036116.

Ni Zhenhua et al: "CLPTM1L is Overexpressed in Lung Cancer and Associated with Apoptosis", PLoS One, vol. 7, No. 12, Dec. 2012 (Dec. 2012), XP055175473.

International Preliminary Report on Patentability, PCT/US2015/010219, dated Jul. 19, 2016, 7 pages.

Examination Report, EP 15701267.5, dated Aug. 31, 2018, 7 pages.

International Search Report, PCT/US2015/010219, dated Mar. 30, 2015, 11 pages.

Written Opinion, SG 11201605745V, dated Apr. 3, 2017, 8 pages.

Written Opinion, SG 11201605745V, dated Mar. 7, 2018, 6 pages.

Michael A. James et al: "Functional Characterization of CLPTM1 Las a Lung Cancer Risk Candidate Gene in the 5p15.33 Locus", PLoS ONE, vol. 7, No. 6, Jun. 4, 2012 (Jun. 4, 2012), p. e36116, XP055175210, DOI: 10.1371 / journal.pone.0036116.

Ni Zhenhua et al: "CLPTM1 L Is Overexpressed in Lung Cancer and Associated with Apoptosis", PLoS ONE, vol. 7, No. 12, Dec. 2012 (Dec. 2012), page Article No. e52598, XP002737101, ISSN: 1932-6203(print).

(Continued)

*Primary Examiner* — Hong Sang

(74) *Attorney, Agent, or Firm* — Quarles & Brady LLP

(57) ABSTRACT

Provided herein are therapeutic agents having specificity for human CLPTM1 L polypeptide, including therapeutic agents comprising one or more CLPTM1 L-targeting agents, compositions comprising such therapeutic agents, and methods of using such compositions for treating or preventing a cancer, pre-cancerous lesion, or other disease condition associated with CLPTM1 L protein dysfunction (e.g., pathogenic production, modification, or function).

8 Claims, 20 Drawing Sheets

Specification includes a Sequence Listing.

(56) References Cited

OTHER PUBLICATIONS

Omasits et al., Bioinformatics 30(6):884-6 (2014).
Skerra & Pluckthun, Science 240:1038-41 (1988).
Bird et al., Science 242:423-26 (1988).
Huston et al., Proc. Natl. Acad. Sci. USA 85:5879-83 (1988).
Jakobovits et al., Proc. Natl. Acad. Sci. USA, 90:2551 (1993).
Jakobovits et al., Nature, 362:255-258 (1993).
Scatchard et al. (Ann. N.Y. Acad. Sci. USA 51:660 (1949).
Smaglo et al., Nat. Rev. Clin. Oncol. 11(11):637-48 (2014).
Jones et al., Nature, 321:522-525 (1986).
Reichmann et al., Nature, 332:323-327 (1988).
Verhoeyen et al., Science, 239:1534-1536 (1988).
Millstein et al., Nature, 305:537-539 (1983).
Vincent and Zurini, Biotechnol. J. 7(12):1444-50 (2012).
Kaneko and Niwa, Biodrugs 25(1):1-11 (2011).
Chames et al., mAbs 1:6, 539-547 (2009).
Tutt et al., J. Immunol. 147: 60 (1991).
Gleason et al., Mol. Cancer. Ther. 11(12):2674-84 (2012).
Wang et al., J Biochem. 135(4):555-65 (2004).
Caron et al., J. Exp Med. 176:1191-1195 (1992).
Wolff et al., Cancer Research 53:2560-2565 (1993).
Stevenson et al., Anti-Cancer Drug Design 3:219-230 (1989).
Kenderian et al., Cancer Res. 74(22):6383-9 (2014).
Groves et al., J. Immunol. Methods, 313:129-39, 2006.
Barbas et al., Proc. Natl. Acad. Sci. USA, 91:3809-13, 1994.
Rohloff et al., Molecular Therapy Nucleic Acids 3:e201 (2014).
Zhu et al., Theranostics 4(9):931-944 (2014).
Ellington and Szostak, Nature 346:818-822 (1990).
Weiner et al., Nature Rev. Immunol. 10:317-327 (2010).
Slaney et al., Cancer Res. 74:7168-7174 (2014).
Therasse et al., J. Natl. Cancer Inst. 92:205-16, 2000.
Hudis, Trastuzumab—mechanism of action and use in clinical practice, N Engl J Med. Jul. 5, 2007;357(1):39-51.
Maloney, Anti-CD20 Antibody Therapy for B-Cell Lymphomas, N Engl J Med 2012; 366:2008-2016 May 24, 2012.
Chen R, Jiang X, Sun D, Han G, Wang F, Ye M, et al. Glycoproteomics analysis of human liver tissue by combination of multiple enzyme digestion and hydrazide chemistry. J Proteome Res. 2009;8:651-61.
James MA, Vikis HG, Tate E, Rymaszewski AL, You M. CRR9/CLPTM1L Regulates Survival Signaling and is Required for Oncogenic Transformation, Anchorage Independence and Lung Tumorigenesis in Ras Driven Models. Cancer Research. 2013.
Clynes RA, Towers TL, Presta LG, Ravetch JV. Inhibitory Fc receptors modulate in vivo cytotoxicity against tumor targets. Nat Med. 2000;6:443-6.
Chen XF, Cai S, Chen QG, Ni ZH, Tang JH, Xu DW, et al. Multiple variants of TERT and CLPTM1L constitute risk factors for lung adenocarcinoma. Genet Mol Res. 2012;11:370-8.
Pande M, Spitz MR, Wu X, Gorlov IP, Chen WV, Amos CI. Novel genetic variants in the chromosome 5p15.33 region associate with lung cancer risk. Carcinogenesis. 2011;32:1493-9.
Wang S, Wu J, Hu L, Ding C, Kan Y, Shen Y, et al. Common genetic variants in TERT contribute to risk of cervical cancer in a Chinese population. Mol Carcinog. 2012.
McKay JD, Hung RJ, Gaborieau V, Boffetta P, Chabrier A, Bymes G, et al. Lung cancer susceptibility locus at 5p15.33. Nat Genet. 2008;40:1404-6.
Wang Y, Broderick P, Webb E, Wu X, Vijayakrishnan J, Matakidou A, et al. Common 5p15.33 and 6p21.33 variants influence lung cancer risk. Nat Genet. 2008;40:1407-9.
Petersen GM, Amundadottir L, Fuchs CS, Kraft P, Stolzenberg-Solomon RZ, Jacobs KB, et al. A genome-wide association study identifies pancreatic cancer susceptibility loci on chromosomes 13q22.1, 1q32.1 and 5p15.33. Nat Genet. 2010;42:224-8.
Rothman N, Garcia-Closas M, Chatterjee N, Malats N, Wu X, Figueroa JD, et al. A multi-stage genome-wide association study of bladder cancer identifies multiple susceptibility loci. Nat Genet. 2010;42:978-84.
Landi MT, Chatterjee N, Yu K, Goldin LR, Goldstein AM, Rotunno M, et al. A Genome-wide Association Study of Lung Cancer Identifies a Region of Chromosome 5p15 Associated with Risk for Adenocarcinoma. The American Journal of Human Genetics. 2009;85:679-91.
Zhao Y, Chen G, Song X, Chen H, Mao Y, Lu D. Fine-mapping of a region of chromosome 5p15.33 (TERT-CLPTM1L) suggests a novel locus in TERT and a CLPTM1L haplotype are associated with glioma susceptibility in a Chinese population. Int J Cancer. 2011.
Liu P, Vikis HG, Lu Y, Wang Y, Schwartz AG, Pinney SM, et al. Cumulative effect of multiple loci on genetic susceptibility to familial lung cancer. Cancer Epidemiol Biomarkers Prev. 2010 19:517-24.
Yin J, Li Y, Yin M, Sun J, Liu L, Qin Q, et al. <italic>TERT-CLPTM1L</italic> Polymorphism rs401681 Contributes to Cancers Risk: Evidence from a Meta-Analysis Based on 29 Publications. PLoS One. 2012;7:e50650.
Zhong, et al. Genetic variations in TERT-CLPTM1L locus are associated with risk of lung cancer in chinese population. Mol Carcinog. Nov. 2013;52(S1):118-126. doi: 10.1002/mc.22043. Epub Jun. 12, 2013.
Wauters, et al. The TERT-CLPTM1L locus for lung cancer predisposes to bronchial obstruction and emphysema. Eur Respir J. Oct. 2011;38(4):924-31. doi: 10.1183/09031936.00187110. Epub May 26, 2011.
Rafnar, et al. Sequence variants at the TERT-CLPTM1L locus associate with many cancer types. Nat Genet. Feb. 2009;41(2):221-7. doi: 10.1038/ng.296. Epub Jan. 18, 2009.
Kang, et al. Gain at chromosomal region 5p15.33, containing TERT, is the most frequent genetic event in early stages of non-small cell lung cancer. Cancer Genet Cytogenet. Apr. 1, 2008; 182(1):1-11. doi: 10.1016/j.cancergencylo.2007.12.004.
Jia et al. CLPTM1L promotes growth and enhances aneuploidy in pancreatic cancer cells, Cancer Research, 2014.
Zhang, et al. Upregulation of miR-494 inhibits cell growth and invasion and induces cell apoptosis by targeting cleft lip and palate transmembrane 1-like in esophageal squamous cell carcinoma, Dig Dis Sci, 2014.

* cited by examiner

B

B.

A

Summary:

| | Mean | SEM | N | t-test |
|---|---|---|---|---|
| normal | 0 | 0 | 16 | |
| tumor | 1.456784 | 0.124848 | 31 | $p<0.05$ |

Intensity scoring - 0=negative 1=weak 2=moderate 3=strong

B Overall Survival by cipt tertile

C

B

D

Monoclonal antibody 10-2 treatment of PDAC cells

B.

A.

Characterization of in-vitro anti-tumor effects of monoclonal anti-CLPTM1L antibodies

| mAb | Targets Both Isoforms | IF Staining Intensity | Punctate Surface Staining | pAkt Inhibition | | Bcl-xL Inhibition | | CDDP Sensitization | | Tumor Spheroid Growth |
|---|---|---|---|---|---|---|---|---|---|---|
| | | A549 | A549 | A549 | H838 | A549 | H838 | A549 | H838 | H838 |
| 6-1 | - | +++ | - | ++ | +/- | + | - | + | + | - |
| 6-2 | - | + | - | + | +/- | + | - | - | +/- | - |
| 7-1 | - | ++ | - | +/- | - | +/- | - | - | - | - |
| 7-2 | - | + | - | - | - | +/- | - | - | +/- | - |
| 8 | + | ++ | + | +/- | - | - | - | + | + | - |
| 9-1 | + | ++ | + | + | - | + | - | +/- | + | - |
| 9-2 | + | + | + | - | +/- | +/- | +/- | +/- | - | - |
| 10-1 | + | ++ | + | + | +/- | - | +/- | - | +/- | +/- |
| 10-2 | + | ++ | + | ++ | + | + | + | +/- | +/- | + |
| 10-3 | + | +++ | + | ++ | + | + | + | +/- | +/- | + |

FIG. 10

SEQUENCE LISTING

<160> NUMBER OF SEQ ID NOS: 25

<210> SEQ ID NO 1
<211> LENGTH: 27311
<212> TYPE: DNA
<213> ORGANISM: Homo sapiens

<400> SEQUENCE: 1

```
gcggggccgg cgaatcccgc ggcgccaggt gggagcgggg ccggagcatg cggggcggcc     60
ggcggtctgc ggcgcgcggc gcattcgttc cccgcggcg gtggcggtgg cgcgcggcgg    120
ctctccagtg agcggcggag cccggagcgg cgggctgggc gccgggcggg cggggctcgc    180
ggctgagagg cgggcgggcc gggggcgccg ggcgcggggc cgccatgtgg agcggccgca    240
gctccttcac cagcttggtg gtgggcgtgt tcgtggtcta cgtggtgcac acctgctggg    300
tcatgtacgg catcgtctac acccgcccgt gctccggcga cgccaactgc atccagccct    360
acctggcgcg gcggcccaag ctgcaggtga gcgtccgcgg ggccgggggc cgggcgggtt    420
ggggtggggg cctctcctcc aggccccaga cgtcgccttc ccgtcccagt tcggagctgt    480
ggccgcgcga gtcgagatgg aacctttcct ggttccccag cggccaggtc ttccgccctc    540
cagctggccg tgggatttga gtgcgtcctg ccagggcctg gccgagctga ctctcgacgc    600
cccctccttt ccagctgagc gtgtacacca cgacgaggtc ccacctgggt gctgagaaca    660
acatcgacct ggtcttgaat gtggaagact ttgatgtgga gtccaaattt gaaaggtatg    720
ggcgtaggac aaaatgccag tgaaagggaa aacattactc atgttcagat tgtttaaaag    780
ttagctttct gtacataaca tgtttatttt agagaactag tcttaccgaa tgtcttgaag    840
tggtagaata tcctaactgg aggcctatgc gtggcctgta aacattcagc ctggaaggtg    900
acaggtgatg aatgtcgttt aagaagtagt tctcagcaga gtgtgatggc agtgggatgt    960
cctggacggg gaggctccga aggagcaggg gccacgcttg gtgaaccagt ggagagcaga   1020
caactctgca gtttcactac cggggaccaa cttgtctttt cctggtggaa gtagttcgct   1080
taagttactt gtgagggaaa agagatgagg atagaggaag caattttgta gaaaatcata   1140
aataagtgac atgtgacgtt agaatagatc aatgtccaaa tatgtagagt atcttaaaaa   1200
ttacatctga catggcctaa tttttttaa ttgaataagt atacttttaa atatgatttg   1260
cttctcacaa gtcaaccatt tcccttcatt gcctgggagg tatctgagga gagaataatg   1320
aaagtttgag actcatgctg gactccacgc cctctaggca gccagtccct gggggtagct   1380
ggaggcgctg gcaagccggt ttctgcctgg cctctttagg cctgtgacct caagccagtt   1440
cctgccctct ctctgcctcc atgaagggga ggccagaagt gctggtgacc aagctgcccg   1500
ctcggttgta gctgcccaca cctttcaaaa atgctcagga ttcatctgca ctgggtttaa   1560
tttcccagac atgaatactg cctcttccgt gccgggccgt gtaccagtta ccaaggacag   1620
ctagtgaggt tttccatttg acctggcaca gtgtcagcct ggaggaagtg gggagaatga   1680
gcactcttaa cacagctccg cctcaagtgt ctccaagtgc acattccacc agaaatacac   1740
agccctgcac cctctgcctg aagagagaca cttaagatgt cctggtggag acatactctt   1800
tcctgggtag tgaggagcca tagatgcctt tgtgtttttc attacaactt tggccgtaag   1860
attttttttt ttttttgaga tagagtcttg ctctgttgcc aggctggagt gcagtggcgt   1920
gatctctgct cactgcaacc tccggttccc gggttcaagg gattctcctg ccttagcctc   1980
caaagtagct gagactacag gcacccgcca ccacgcctgg ctaatttttt tatttttagt   2040
agagacaggg tttcaccatg ttggctgggc tggtctgaaa ctcctgacct cgtgatctgc   2100
```

```
ccggctcggc ctcccaaggt gctgggatta caggcgtgag ccgccgcacc cggccaaccg   2160
taagattttt aaggagaggc cgggcacagt gactcatgcc tataatccca gcagtttggg   2220
aggccaaggc gggaggatca cttgagccca gcagttcaag accagcctag gcaatgtgac   2280
aaaaccccat ctctacaaca gttttcaaag ttagccaggc atggtggcac gcccacctgt   2340
agtcccagct actcgggaga ctgaggcggg aggtcacttg agctcaggag gttgaggatg   2400
cagtgagctg tgattgcacc cctacacttt cagcctggtg acagcgagac cttgtctcaa   2460
aaaagagact tttaaagagg aagaagaact catgtaaccg taaacaggtg gaatgcgagg   2520
tttttccatg gggctgtagt atggacgtcg ggccctggtg tgcgggtgaa gagccaggca   2580
cctggtccga ggcctacagt tgtagcagct cgccgggcct ttcctcagct cgtgctggat   2640
gccacacagt caggactgac agccttgaaa gtcagtcctt tgtggctgat catcttttta   2700
tccttaaaac tacaacaccc aaaaaaacta cccacattaa atttctgagg ttccagtagt   2760
gtgggccgag gcacctggag ccctcgtggc tgctgccctt cccttctgtc gcttcggagt   2820
tgggtgattc agtgtgtgtg gtcagctggt accctggcca ggcccagaag ctgctttcca   2880
tctggctgct tcagccttgt ggcctcaggt gggttattga cctctcagcc tcctgagatg   2940
gaggcaggaa gtgcgggccg ttttgctttc ggctgtaggc gcccacacct gtgccgagtt   3000
ctcaggacgc gcacgcgtgc gcgtgcacac acacacacac acacacacac acacacgact   3060
cgtaaagccc tgggcaggtg ggtttcattt ttagtacttc tgagctaaaa ttagtttatt   3120
gaagcagctt tataaaggta tttgaatagg ttctagagac ccagaatata atatgtatgt   3180
agtggaaatg attgttctgt ttcaggacag ttaatgtttc tgtaccaaag aaaacgagaa   3240
acaatgggac gctgtatgcc tacatcttcc tccatcacgc tggggtcctg ccgtggcacg   3300
acgggaagca ggtgcacctg gtcagtcctc tgaccaccta catggtcccc aagccagaag   3360
aaatcaacct gctcaccggg gagtctgata cacaggtgag ggtcttcatg ggttactgat   3420
aacaggctgt gcctctccgt cagaacggac atgtctttct ccacacaggt gggcgatgtc   3480
tagggctcca gtgactttgt tgggagtaaa gccaaaagcc attggaatgt tactggcgtg   3540
catttctgac tttcagctga atcatatcca tgagtttgca gacaagtttt atctaaaatt   3600
agggacagtt gaagtgatcg ctggcattct cgatgcagag tccctcgggg aatgggccct   3660
ctcagtctct gggggcacct actgcacctg gtgggatgga gcgctggtcc tgcagagctg   3720
gcctgcagct tctcaccagg agctctgggg atgagagctg ggctcattct gcattctgtg   3780
taggactggg ctattcctag atgtttattc taagaatgta attggagatc atggaaaagg   3840
tagaggtaca agttgtagtt tgtacatctg tagaaaggtg tatgcgcaaa taaaaactgg   3900
aagtcactta agtgatcatg aatacaggcc aaggataaag caagggaatt ctgacaccca   3960
cctttgtgtt gagtggaagg tgagataatt tacaaaacaa ggccgggcgc agtggctcat   4020
gcctgtaatc ccagcacttt gggaggctga ggcaggtgga tcacctgcag tcaggagttc   4080
gagactagcc tggccaacat ggtgaaaccc cgtctctact aaaaatacaa aaattagctg   4140
gatgtggtgg cacgcgcctg taatcccagc tactcaggag gctgagggag gagaatcgtt   4200
tgaacccgtg aggtgagatg atgccactgc attccagcct gggcgacaga gggagactct   4260
gcctcagaaa aatttacaaa acaagaaaga tggcagcttt ccaggaagag gctgtgaaat   4320
tgttccagac agagagaaag agaggtctct cggagttgat ggggttttga aagccctacc   4380
aacacctgct cctgcctctc cccagtttgc atctgtctcc ttaggaacat ccctcacctg   4440
```

-continued

```
ccccctctccg tgtcccctca tctggggccc ccatccctcc tctccagtgt cctgaaaagt   4500
gggtggggtg atgggcatgt agcatgtagc gcaggaagcc tcccttgcag gtagcaaatg   4560
tgaggaggtg tggaaaaccg tttgtaatgt aaattatcgc taaactgcat ctttaggtag   4620
gaaatgggtg aggcgatagt gcttcctagg atgtatcaga tctgagccga gctaagattt   4680
ccctgtcagt ccatgtcctg tttaacttca tgtaagagcc gtgtgtaatc ctcagtatgt   4740
ctcctttagg cagccccaca tgcttggttt tagaagctga ctccctctca gtctccttac   4800
agccacaggg ctgtgtgagc cctggacttg cacagtcttc tgccaaggtc agggggctct   4860
caccctctca acttctgaga agtgggccca cttagtttga ggacctcaaa aaaggaattg   4920
gtgaagtccg tgaccacatg ttgcaaagca gcaccccctg gcttccgtgg agataaggat   4980
ggggggctgt ttggcgagag tctggcggaa ttggcagctg tggggccgct gtgccctctc   5040
tgctgggctc tcccccggtt gtgcctgtgc gtggccatct gttcacaggt tagggtgccg   5100
accctgctgt ccgggcgcgg tttttccatg tgcgtggcca tctgttcaca ggttagggcg   5160
ctgaccctgc tgtcccgggc acagtttgcc cgtctgtgtg gccatctgtt cacaggttag   5220
ggcgctgacc ctgctgtccc gagcacagtt tgcccgtctg tgtggccgtt ctcttcacag   5280
gttagggtgc tgaccctgct gtccgggcgc ggtttttcca tgtgcgtggc catctgttca   5340
caggttaggg cgctgactct gctgtcccgg gcacagtttg cccatctgtg tggccatctg   5400
ttcacaggtt agggcgctga ccctgctgtc ccgagcacag tttgcccgtc tgtgtggccg   5460
ttctcttcac aggttagggt gccgaccctg ctgtccgggc gcggtttttc catgtgcgtg   5520
gccatctgtt cacaggttag ggcgctgacc ctgctgtccc gggcacagtt tgcccgtctg   5580
tgtggccatc tgttcacagg ttagggcgct gaccctgctg tcccgggcac agtttgcccg   5640
tctgtgtggc cgttctcttc acaggttagg gtgctgaccc tgctgtccgg gtgcggtttt   5700
tccatgtgcg tggccatctg ttcacaggtt agggcgctga ccctgctgtc ccgggcacag   5760
tttgccagtc tgtgtggcca tctgttcaca ggttagggca ctgaccctgc tgtcccgggc   5820
acagtttgcc cgtctgtgtg gccgttctct tcacaggtta gggtgctgac cctgctgtcc   5880
cgggcacagt ttgcccgtct gtgtggccat ctcttcacag gttagggggc tgaccctgct   5940
gtcccgggca cagtttgcct gtctgtgtgg ccgttctgtt cgcaggttag gggctgacc    6000
ctgctgtcct gggcatggtt ttctgtccca gcattggcct ctgttttcct cacttaacag   6060
cagatcgagg cggagaagaa gccgacgagt gccctggatg agccagtgtc ccactggcga   6120
ccgcggctgg cgctgaacgt gatggcggac aactttgtct ttgacgggtc ctccctgcct   6180
gccgatgtgc atcggtacat gaagatgtaa gtggggcccc agagctggag cgccgggggg   6240
agggtgctgg gaccctggct ggccagaact cgccagcagg tcactcctgc accgtggagt   6300
cccctctgtg gggaggcact tgctgcccgg gcctcccagc tctttcccac ttcctcattg   6360
aggttgtgct gctaccacag ggctggaagg ggggagaaag gaattcaagc tggagcatcc   6420
tgccctttgc tcctggctgg cgaaggcttc catggagaga aaacggaagg cgctgatggg   6480
aacgggttgc tttgctcccc ttgtgatttt ttaacttggc ttatttagat ttacttaaaa   6540
gttaatcttt agattattta gtatcacttg ccatcagtta aatacaatta ttggaattca   6600
cgtgtttggc cacctgagct cacctcgtct ctcccatgtg ttggggatcc cccccccaac   6660
tcctgcgcca cagctccgcc tcccaggtgg ctgcaggtga ctcgcccttc caagtgtagt   6720
ggccacatcc tgggattgct ccgtgtcagt gcatcctggg attgctccgt gtcagtgcgc   6780
agagggccct gggttctgct gtacggccgt gtccctgtaa ttcccccgct cctagtggcc   6840
```

```
gtggaggcat tttcccacct gtggccatca cttcctgggg agcgggtctc acaagcgtgc   6900
atatgttgtc aggctctctg cttccgtttg gggaggctgt gccctggggt cattgtgact   6960
gagaagcagt tgagggtggt gctgggggca cttctctggg gtaaacccag tgtctggatg   7020
tgttcattca ttgaaaggta aaagccttgg tgctgacttt ggaaagttgt gctttaatcc   7080
caggatccag ctggggaaaa ccgtgcatta cctgcccatc ctgttcatcg accagctcag   7140
caaccgcgtg aaggacctga tggtgagtga cacctctgcc cgctggttgt gcagctggcg   7200
agacactgac cccaagactg gccccgcagc ccctgcaccc taatggaccg ggccattgct   7260
gacatttgac acggtgcttt tacccgtgct gggaagcact gccttcgagt gtgcgagggt   7320
tgtgacaggg gggccctggt ggtgtgctgg gtttgccgtt ggctggctgc ggggtcctgc   7380
tgagcctctg gactgtcact ggtgaaaggc ccctggaaga ttgtttatgc agcgcataga   7440
gggcagcgct tagagagcag gcacatgagc accgtgtgaa acagcgtctg cgtgtgagct   7500
cctggtgtgc catgtagatt aattcacagt atcctgagca aactcctgct ttccccacca   7560
gggctggtcc tgcacaggcg gccagaggag cgggtgacag cccttcctcg gagctggagc   7620
ccccggggtg gcccctggca aggcggaagg cctttgcgaa tagaagtggc tgctctctgg   7680
gctctggcgc cctgtgatta cgggcagtga cagcgcctgc tctcccatag ttgctttgag   7740
aggagatgaa atgtggccaa cctttggcca gtattgagac tcacagaagc agttaatatt   7800
taatgtctct tactgcacat gaggcactgt gctaagcact ttgtgaatct ttccgtaatt   7860
gtggtgctgg gagctgtggc gttgtttcac ggatgaggtt atttggggtt cagaggtgaa   7920
cgctcagctg gggccctgca ggatcgctgc cctgccctgc ctccctgcaa gccatcactg   7980
tcactccgga tcacccacta ggagccggcc acttccactt aaggctctcg gcacctctga   8040
cctctgaggc gggccctttc ccctttttttg ttgaagagga aacagtcctg gggagagcag   8100
agggcttgct agcggggggg tgcagctggg aaacggagaa gcgagcacct ggctgctttg   8160
atctctgccc aggccctgct gcctcctcct gactgcggct ctcagaacag tccccctgta   8220
ctgctgttcc ctcagacccc ttgcagtccc taacatactg cctccttcac ttctggggtc   8280
actgattgct cctatacaac ctgcaggctg gggctgcac aggcagtggc tggcgagcag   8340
gtctggcgct gcagcctatc cctgagtagt ttctctgtcg gcccctgcaa ttccaacctc   8400
tttctctgtt tgctggagtt tgctggtgtg ctgctgacaa acctcaggac agcaagttct   8460
gctaaaatgc cccatacaga gctgtgtgag ctgtggcacc agctcgtggt cacctcttgt   8520
gaagcctcat gccgctgact ccttgcaggc attcaggaga tggtggacag gggcaggcag   8580
ctgcagaagg ctgccctgtg tgtctgtctg cagatctgtc ttgttagagg cccggggcag   8640
gctttgcggc gcagctgtgc cagtggtggc ctgcgttcca gtggttatgg agacacgtgt   8700
gccgacagca gcttttcccc caaatcacag tctctctcat gtgtcgctgt tgctgtgtct   8760
cacttggggc cagattcgag aggtgctgtc ttgagagagg aagcaggcag ctgggatgca   8820
gcaggtgcag gaagtcggca ccttctgtgg ctgggcccag cactgccaga tggaggaggc   8880
agtgacaccc ttcggacacg cttggcagct cgaggggtgc ctggaggcca ccatccatgt   8940
gcactgatgc cacttggcta cgtggggcgc cctgacagcc gctctcaggg caacctggca   9000
cctgctggtt gtggctctga ttccaccaca ccctgacacc agcagtgccc gccatagcag   9060
agcaggtgga ttagagcaca gccctcgctg gatgttccag cacgtggagg gtggcgggtc   9120
agggcttgag gcagggcagg tggattagag cacagccctc gctggatgtt ccagaacgtg   9180
```

-continued

```
gagggtggtg ctcaccgggt gtggtcactg cccacgtgct gtagggtgtg ggctcgcgct   9240
tgtgaacccg ttcctcaccc tcctacctcg gcaccctggg acctggccca cagcctgtgt   9300
gcgtgaggcc ccggcaggct gcaggactaa gctcgtggtt ctgagaccta cacatccacc   9360
ctactgcccc tgctagcttt gcgttccaga agctttctgt tgtccccacg gccacccccct   9420
gctctgtgct ttaggccctg aggcactttg cccatgtgct gcagggctgt gcttgtcccg   9480
tggtctccaa ctcttaggac aggccagggc tctgcaggcc aagctcagcg ccgtatgctg   9540
cgccatggag tcctagcagc tgggtggcaa gcaccacctc cggggcacca ggacttgtgc   9600
ggcttaaaat tgaaggggca cgtgcagcaa aacagaccag gcactgctag cgctgctgag   9660
ctcacggggt cctggtgggg gtgggaacct ccctgtgctg gaacgcagca cgctggggcc   9720
tgaggcctgt ggtgacagaa ggagggaccg ggggatgctt gctgggccca gtcatggctg   9780
acctggggcc acacagggat gggaaggggg atggcagggt tggcgagggc tgccaggcag   9840
ctgggtgcaa gggtatgagg gcagggccct cagtgtggct ttcttcatca ggtcataaac   9900
cgctccacca ccgagctgcc cctcaccgtg tcctacgaca aggtctcact ggggcggctg   9960
cgcttctgga tccacatgca ggacgccgtg tactccctgc agcagttcgg tatgtgccgc  10020
acacggccgg cgcctgggtg aggccgccct ggagcccctc gggcatccaa gtgcgaatcc  10080
tgacacaggc cggggcctcc tcgcctcctg ctgcagatcc ttgcacagac gttgaatcag  10140
aggctagcag cgcctgcctc acttctctcc ttggagatga cctggttgat tgtctggaaa  10200
ttggctttat taagaacata atatgtgaaa tgccatgagt ttggtcaaat gaaccttaac  10260
tgttgatgag atttattttt attgtttgtt tgtttgtttg tttgtttgtt ttgagacaga  10320
gtctcgctct gttgcccagg ctggagtgca gtggcacaat ctctggttac tgcagcctcc  10380
gcccccgga ttcaagcgat tctcgttcct cagtcccccc agtagctagg attacaggcg  10440
cgtgccccca cgcccagcta atttttgtat ttttagtaga gatggagttt caccatgttt  10500
accaggctgg tcttgaactc ctgacttcaa gtgatctgcc tgcctgagat tcccaaagtg  10560
ctgggtttac aggcatgagc cactgcgccc ggcctaaatt tttatattga aaactgtatt  10620
tgtaatgtta ggtaagattg acattgcctg ttttatattg tatgtttttt tttccttgac  10680
agggttttca gagaaagatg ctgatgaggt gaaaggaatt tttgtagata ccaacttata  10740
cttcctggcg ctgaccttct ttgtcgcagc gttccatgtg agtcatccac cggggggctt  10800
gccgcaggca cttgggggc tccctgggcc ccgggcctcc tgcaggggtc ctggacctgg  10860
ggtttgtggg cgccgtccag ccctgtggcc ctcaagtgtc cactcccatc actcagcagc  10920
cagcacgcct gacaccaggc gaccattgtc ccagtgggcg gtttctccca gttctgaaaa  10980
gggagggacc ataaagctcc gtccacagcc ttggcgactt gggctgtgct ggctttgggg  11040
gcggttttga aaaggatcca gggtactctg agcagtgtcc acaccaatga gatgaatagg  11100
tgcaggcatc tcactctccc ctgcccaggc cccgacccca tgcagagcca ggggcggagc  11160
tgggcagcct ctagcagaaa gtagttctct tgtataaatt ctaacacact gatttttaaa  11220
tgtaaaaagt cagtcctgtg tgtatacagt agttcccct tacccgatgt gtatacagta  11280
gtcccccctt atcctcatcc ggtgtgtata cagtagtccc cccttatcct catccggtgt  11340
gtatacagta gtcccccctt atcctcttgc ggtgtgtcta cagtagtccc cccttatcct  11400
cagccggtgt gtatacagta gtccccctta tcctcatctg gtgtgtatac aatagtccct  11460
catcctcatc ccgtgtgtat acagtagtct ccccttatcc tcatccggtg tgtatacagt  11520
agtccccct tatcctcatc tggtgtgtat acagtagtcc cccttatcc tcatctggtg  11580
```

```
tgtatacaat agtcccccct tatcctcatc caatgtgtat acagtagtcc ccccttatcc  11640
tcatcccgtg tgtgtataca gtagtccccc cttatcctca tctggtgtgt atacagtagt  11700
ccccccttat cctcatgtgg tgtgtataca atagtccctc atcctcatcc cgtgtgtata  11760
cagtagtctc cccttatcct catctggtgt gtatacagta gtcccccctt atctggtgtg  11820
tatacagtag tccccccctta tccggtgtgt ctacagtagt ccccccttat cctcatccgg  11880
tgtgtataca gtagtccccc cttatcctca tccggtgtgt atacagtagt ccccccttat  11940
ccggtgtgtc tacagtagtc ccccttatc ctcatccggt gtgtatacag tagtcccccc  12000
ttatcctcat ccggtgtgta tacagtagtc ccccccttatc cggtgtgtct acagtattcc  12060
ccccttatcc tcatcccgtg tgtatacagt agtccccccct tgttctcatc cagtgtatat  12120
acagtagtcc gccccttatc ctcatctggt gttatacagt agtccctcat cctcaggggg  12180
tgtgttcaaa gaccctcatt ggatgtctga atatgtgtat caaataacgt aatgaatgaa  12240
tatatgtatt atgtaatggt tttgataaag ttcaatttat aagttaagca cagtaagaga  12300
ttacccacaa taactggtaa cagaaacagg acaggacagt gtgataaagt tacgtgggtg  12360
tggtctcact ctcagaatat ctgtctcatc gcactgctcc gtgctaaccg aaaccatgga  12420
cagtaaacca tgggtaaagc aaggctgctg tgctcttact gttgttcgtg gagctgagct  12480
gctagggaga gccatccttg tggctgttag gctggcctgt ggttaggcgg cacccaggag  12540
tgcggccggc actggttctg agtgcctggg agtttggctg ccagtcaagc taaaactttc  12600
caaagccgta ctagagaatt aaacgatttt tattaaaagg tcagtgtctc taaggatgag  12660
atcatgcatg gttaggtttt tttaagtttt ttttggagac aggtctcagt acgttgccca  12720
ggctggtctc aaacccctgg gcttaggtgg tcctttggcc ttggccttgc agtagctggg  12780
atcacaggca tgggccacca tgcccagccc ttgcgttttt agcacagttg agagatgagg  12840
ctgccctgag tgggcacaac ccgagagcag gggtgcccag ccaggcccat gatccagggg  12900
aatccagagc ctccaattgc ctgggggcct ttccagcagt tcaagtcaaa ggtacgtatt  12960
atttcagaag tgcccctgca aagcccgcct gggcactcta ggttctgaca tggcaggcca  13020
ggcgcgtaga ggcatgggtc ccgagtgtag acacttatcc tgatgcatcc tgaggctgag  13080
tacacctgca gtctcacggt cacacacgaa gcctctatct ctgtctcaca ggagatggaa  13140
acagcaggag atgtgagttg ctgtcgtgtg tgttctctct agcttctctt tgatttcctg  13200
gcctttaaaa atgacatcag tttctggaag aagaagaaga gcatgatcgg catgtccacc  13260
aaggcaggta ggccccccga gcgtggccct gctcagatac tctgccccag ggagctcact  13320
ggagcctgcg gtagagggct gcctgcctca ctgctggctg cagacacagc cccgggtgtg  13380
tgcttggctc ttgagaagcc tctgagacca ggcaccgtaa agcccaggga gccgttgcgg  13440
caattgtggt gggaccatca gaggctgcac ggctcagggc ctccagcggc tgcacagctc  13500
agggcctggc tgcggactct ggcgtgcatg gggtctgggt ctgggctgtg gagagtgaga  13560
tgcatggacc tctcgagcct tcccggctgc tcatgggcgc tgagcagggc tggggcctca  13620
catcccctgt cttggttccc tcgccccgtc ctcccgccgg tgttccttcc ccgaccagcg  13680
caggcctggg cgtgtggggc ctgccaggtg atggcagtta ataggcccgt ggtgctgtgc  13740
ccagcagtga caggcagtgt gcagctgtta ggtagggcag tcagggaccc ctgaggccag  13800
gcagcccagg caggaggcct gccaagatct gggaccagtg ttcctggcca agggtgcctg  13860
ccgtggttta aggggcccaa gtgagtgagg ggtcctcctg accttgcagg ggtggaggtt  13920
```

-continued

```
gtcacagtgg ggtggggagc ggcggtctgg acaggggcga gtggttgatg ggtgtgagga  13980
cgaggagtgg gtgtgtcctg ttggttagga gtgaggagca tttggctcca gtatcagacc  14040
cgaacaagtt gtttttctcg catggaaaag acgcccaagc aggtggccct ggctgcctgg  14100
gggccgtgcc gtgttctgcg ttgttgtctc ctaaccctaa tgcctttcct ggcgtcctgg  14160
gttggagtgg ccagcagaca gtggctgtgg ccttgaccac tgtttgtcct gtggctccat  14220
ggatctgctt cccctgcttg ccctcagggc ttgcaggagg aggaagacgt gttgaataag  14280
ctggagtggt tcttaaggta cagctgggga ggaaacaaat ccagacttga aaagccacgc  14340
acttatcaca gaactggcat aagacacgcc cggaagcaaa gctgtgctgg ccccgtcatc  14400
cgacctctgc ccacgttcca tgctcatttg caagtgtggc tcagacacgt gtttgtggag  14460
ctggtgtggg gccagctgtt cagttcagca gccttccaaa cactttccta gctgctgaat  14520
gcttcattgt tctttttaaa cggggtgacg tggactgggg agtacctgaa gcttcttggg  14580
cgtggtgggt tgggatgggg gactgggggt atgtgtgtga cttggggaac acaggtgggg  14640
tctgccctgc accccctccc agcccgacca tcctgtcccc agtgctctgg cgctgcttca  14700
gcaccgtggt catctttctg ttcctgctgg acgagcagac gagcctgctg gtgctggtcc  14760
cggcgggtgt tggagccgcc attgaggtga gttccgggca gtgacctgaa ctgtctgagg  14820
tccatgtgcc tccacgcact caggaaaggc tttcagcccc gggacctgag accttctgtg  14880
gaagcctgtg tgcttgttcc cgatggcctc agtgttctgg aagctgtagg atggcaggca  14940
gtgggtgtaa aggctttgaa caagtggaga gcaaggaaat gcgtgttcgg gtggtatcag  15000
ctcatgaggc tctgtccacc aagcagtggt gagtcctgag gccctgtcca ccaagcagat  15060
agtcctgagg ctctgtccac caagcagtgg tgagtcctga ggccctgtcc accaagcaga  15120
gagtcctgag gccctgtcca ccaagcagag agtcctgagg ctctgtccac caagcagaga  15180
gtcctgaggc tctgtccacc aagcagagag tcctgaggcc ctgtccacca agcagagagt  15240
cctgaggccc tgtccaccaa gcagagagtc ctgaggctct gtccaccagg cagagagtcc  15300
tgaggccctg tccaccaggc agagagtcct gaggctctgt ccaccaagca gagagtcctg  15360
aggccctgtc caccaggcag agagtcctga ggccctgtcc accaggcaga gagtcctgag  15420
gccctgtcca ccaggcagag agtcctgagg ccctgtccac caggcagaga gtcctgaggc  15480
cctgtccacc aagcagagag tcctgaggcc ctgtccacca agcagagagt cctgaggctc  15540
tgtccaccaa gcagagagtc ctgaggctct gtccaccaag cagagagtcc tgaggccctg  15600
tccaccaagc agtggtgagt cctgaggccc tgtccaccaa gcagaggcct gaggccctgt  15660
ccaccaaaca gagtgttttc atgtgcttga gaaatcccac catgtgcaaa gcagaggtgt  15720
aaaccgtggg gccttgagag gctcgtgctg tggctggaga tctgagcaca gcggccaggt  15780
aggcactgac ggaaatcact cggtgccctg tggtccagcc ttggttgttc cggagctcag  15840
aaaagccggc caaaagggag cctcgtgggg caagaccagc tcaggagcaa accettgagg  15900
ggggcgatgg ccttcagggt gagagggccc aggcttaagc ctagctcctc actgagctct  15960
gtgccacacc ggcaggagcc ggagtctgag gtctctgcag ttggtggccc acctgtgggt  16020
gggggcctct gcggccgtca tgcctgtaga ggaggagctg gatgcaatgt ctctgtagag  16080
gaggagctgt atgaaatgtg tctgtagagg aggagctgga tggaatgtcc ctgtagagga  16140
ggagctggat gaaatgtgtc tgtagaggag gagctggatg gaatgtgtct gtagaggagg  16200
agctggatga aatgtgtctg tagaggagga gctggatgca atgtgtctgt agagcaggag  16260
ctggatgaaa tgtgtctgta gaggaggatc tggatggagt gtccctgtag aggaggagct  16320
```

```
ggatgaaatg tgtctgtaga ggaggagctg gatggaatgt gtctatagag gaggagctgg  16380
atgaaatgtg tctgtagaca aggagctgga agaaaactgt ctgtagagga ggagctggat  16440
gaagtgtgtc tgtagaggag gagctggatg aaatctgtct gtagaggagg agctggatga  16500
aatgtgtccg tagaggagga gctggatgaa atgtgtctgc agaggaggag ctggatgaaa  16560
tgtgtctgta gaggaggagc tggatggaat gtgtctgcag aggaggagct ggatgaaatg  16620
tgtctgtaga ggaggagctg gatggaatgt gtctgtagag gaggagctgg aagaaatgtc  16680
cctgtagagg aggagctgga tgaaatgtgt ccgtagagga ggagctggat gaaatgtgtc  16740
cgtagaggag tagctggatg aaatgtatcc tgtagaggag gagctggatg gaatgtatcc  16800
tgtagaggag gagctggatg gaatgtgtct gcagaggagg agctggatga aatgtgtctg  16860
tagaggagga gctggatgga atgtgtctgt agaggaggag ctggatggaa tgtgtctgta  16920
gaggaggagc tggatggaat gtgtctgtag aggaggagct ggatggaatg tgtctgtaga  16980
ggaggagctg gatggaatgt gtctgtagag gaggagctgg atggaatgtg tctgtagagg  17040
aggagctgga tggaatgtgt ccgtagagga ggagctggat ggaatgtgtc tgtagaggag  17100
gagctggatg gaatgtgtct gtcgaggagg agctggatgg aatgtgtctg tagaggagga  17160
gctggatgga atgtccctgt agaggaggag ctggatgaaa tgtgtctgta gaggaggagc  17220
tggatggaat gtgtctgtag aggaggagct ggatggaatg tgtctgtaga ggaggagctg  17280
ggtggaatgt ccctgtagag gaggagctgg gtggaatgtc cctgtagagg aggagctgga  17340
tgaaatgtcc ctgtagagga ggagcaggat gaaatgtgtc tgtagaggag gagctggatg  17400
aaatgtgtct gtagaggagg agctgggtgg aatgtgtctg tagaggagga gctggatgaa  17460
atgtgtctgt agaggaggag ctggatggaa tgtccctgta gagcaggagc tggatggaat  17520
gtccctgtag aggaggagct ggatggaatg tccctgtaga ggaggagctg gatgaaatgt  17580
ccctgtagag gaggagctgg atggaatgtc cctgtagagg aggagctgga tgaaatatgt  17640
ctgtagagga ggagctggat ggaatgtgcc tgtagaggag gagctggatg gaatgtgcct  17700
gtagaggagg agctggatgg aatgtgtctg tagaggagga gctggatgga atgtgtctgt  17760
agaggaggag ctggatgaaa tgtccctgta gaggaggagc tggatggaat gtgtctgtcg  17820
aggaggagct ggatgaaatg tgtctgtaga ggaggagctg gatggaatgt gtctgtagag  17880
gaggagctgg atggaatgtg cctgtagagg aggagctgga tgaaatgtgt ctgtagagga  17940
ggagctggat ggaatgtgtc tgtcgaggag gagctgggtg gaatgtccct gtcgaggagg  18000
agctgggtgg aatgtccctg tagaggagga gctgggtgga atgtccctgt agaggaggag  18060
ctggatgaaa tgtccctgtg gaggaggagc tggatggaat gtgtccgtag aggaggagct  18120
ggatgaaatg tgtccgtaga ggaggagctg gatgaaatgt gtccgtagag gaggagctgg  18180
atgaaatgtg tctgtcgagg aggagctgga tgaaatgtgt ctgtcgagga ggagctggat  18240
gaaatgtccc tgtaggggag gagctggatg aaatgtccct gtagaggagg agctggatgg  18300
attgtccctg tagaggagga gctggatgaa atgtccccgt agaggaggag ctggatggaa  18360
tgtccccgta gaggaggagc tggatggaat gtccccgtag aggaggagct ggatgaaatg  18420
tgtctgtaga ggaggagctg gatgaaatgt gtctgtagag gaggagctgg atgaaatgtg  18480
tctgtagagg aggagctgga tggaatgtgt ctagaggagg agctggatga aatgtgtcgg  18540
tagaggagga gctggatgga atgtccctgt agaggaggag ctggatgaaa tgtgtctgtg  18600
gaggaggagc tggatgaaat gaaatgtgtc tgtcgaggag gagctggatg aaatgtgtct  18660
```

-continued

```
gtagaggagg agctggatga aatgtgtctg tagaggagga gctgcatgga atgtgtctgt  18720
agaggaggag ctggatggaa tgtccctgta gaggaggagc tggatgaaat gacgctggag  18780
ctccacaggc agggtccctc cataggtacg agtcacagtg ccgtgcccgg ctctggcacc  18840
cgtcctgagc tccgtgggtg atgccttcca agcatttagc catgaggtgg cggctctcag  18900
agcggtccca aaactggctc cagggctgcc cgagtggcag gcagaagtag gtgggggctt  18960
atttgggtgc aggcagagtg gcgtaaagaa ctgccctcac atgctgtttt tgttgtccgc  19020
tgggcggtgg ctgtgcagcc cacctgacca ggtacgcctg ccgtgtgtgg gttagaggcc  19080
caggtccagc ctccagcgct ctggcctgag ctgtgggagg gacaggaaga ggacagtggg  19140
ctgcgcgggg ccatgggcag caggtcctac ccgttactgt ctgggtcgtt cattcgtggc  19200
tcctggcctt cgaatattaa aggaactatt tcctgatttc tcccctcagc tgtggaaagt  19260
gaagaaggca ttgaagatga ctattttttg gagaggcctg atgcccgaat ttcaggtagg  19320
atttagttgt aatggctgaa ccccaagcct ctctgaagag tgtgattttg ccccctgtgc  19380
aaagagtaag atggccatct gcagatgagt cactgcgggc ctctgtcagg ggagcctccg  19440
tggtggaggc agcactggtt tctgatcgca gccactctct tcgcctgagg attccccggt  19500
catataccta gttctgaccg tcttcagtgc agacggcagc acttctgggc ctgagccggc  19560
ctctgggagg aaggatgctg gctggccagc acgtgtgctt cgttttggca ccttgtccag  19620
aggcgctccc gaggctggtg ctgactgggg tccgtacagt cctggcagtc ctgaagtgag  19680
tgagcccctg ccctgagctg gtggctgccc cagtgcctgg gcgcccataa ggcccctagg  19740
cagatgaggg ctggggcaga gctggagttg aatctcagtg cccacggatg gaccttgatt  19800
gaggcggggc cctcagcagt cacaggctga gattttccat gctgtgggca ggggggtcag  19860
gaagcccagc acacgcagcg cagccactgt gttccacctt gccccatggc tcccggccgg  19920
ctggttcgga gcagtgttgg ctgtgcctgt gtgctctgca gtgttctcac tgaagcggtg  19980
gcactgaaaa ctgagccacc tgagcaagga acagcagtga ggccgcgttg cccccatcag  20040
gcttgtggga cccagggcca gggtgaggcg ggaaggatcc atgcggatcc ccgtcctctg  20100
ggtcctctcc tcgcctggta gggacctgag cgccctctgt agtgaggcct gggtcagctc  20160
tgcagccata tgtgacgccc cttagtcaca gctcagctgt gctcagatcc tccctgagtc  20220
tattaatatc actgtgttga atttcacaac agtttggcac ttacagcgaa tctgagagga  20280
aaaccgagga gtacgatact caggtaagtc acttgtgatt cagggcacgt gcatgccagg  20340
caaatccaac accctcaaag acgggtcttt tactgtcatt gctcagtgcg gaagtctcct  20400
tggagtacgg gtcagcccgc cttgagcagg gatcccaaga gtgaacacat aaaacccaaa  20460
tttcttactg ggaagggcgg gggctcgcag agactcattt cccagtcctt acaggcacag  20520
cctgcctgtg tcaccgtata gtagggatat tttcatcgtt tgtaagtcac attcgccagg  20580
cagctgacgc aggccatggt gtctgctgtg gttgctggga acgcacttgc cgtcaccaag  20640
gccataatgg ccgcggccgc acagtggcct ggaggaatgg ccccagcagc acagggcgtc  20700
acctttcccc attgctgttg ggggagctgg aattctcagt tccagttaat agaacatttc  20760
tgcacagatg attttagttt ggtttaatct tcaccagctt atatccaact tgcatggcgt  20820
tgtaaagctg aaatcagaat ggatacagct ggcgatgtaa ctacattact tagtaggcag  20880
ttttttccgg tttctttcca ttatgtttat tgatctgttg tgggttggtt ggttttgacc  20940
aaccagaatt gatctattat tgttaactag cgcctgtagt tacacccggg ctctggcgtg  21000
tgcggtgcct cctggggctg tggcgagtgt gcgatgccct gcctgtgccc ctcacgccgc  21060
```

-continued

```
cccctgcaga gcagccctgc caccctgagc gctgtagctc gttctgtctg tccctgtcgg  21120
ggtgagctcc atgcagtgtg tttacagagg cttggcgttt gggcctctaa ctggaagcca  21180
tctttgttcc ctgcaggcca tgaagtactt gtcatacctg ctgtaccctc tctgtgtcgg  21240
gggtgctgtc tattcactcc tgaatatcaa atataagagg taggaggccg cacacgcttc  21300
ccctgctgcg tctttcccct gagaaagcca tttggatgac tgagccagag cggggtgcga  21360
ctggagggca aactcggggc cggggcactt gggccagcgc ctgggagggg tcctgcccct  21420
gcagctgcac acggtgggct ctgggcctca gtgtccccct ggtaaggtgt agctgagagg  21480
actgactcca gccaccaggc ttcatgggag gcttgggcct gagctgagag gggtcctgga  21540
gcccctggcc tctgctgccc gtgtggggtg ctggccctga gctgagaggg ttcccggagc  21600
ccccggcctc tgctgcctgg gtggggtgtt ggccctgagc cgagaggggt cctggagcct  21660
ccagcctctg ctgcccgggt ggggtgctgg ccctgagcca agagggatcc cggagccccc  21720
agcctctgtt gcccaggtgg gctgctggcc ctgagccaag agggatcccg gagcctccag  21780
cctctgctgc ccaggtgggg tgctggccct gagctgaggg gttcctggag tgcccggcct  21840
ctgctgcccg ggcagggtgc tggccctgag ctgagagggg tcctggagcc cctggcctct  21900
gctgcccagg tggggtgctg gccctgagct gaggggttcc tggagtgccc ggcctctgct  21960
gcccggccgg gggtgctcag cgctatctcc agcttgagaa ccaggctcag cactgctgct  22020
cttggctgcc gagctgccgt gagagcatct gggtattttc agaggatttt taatgaaaga  22080
attatttttc atcaatttaa tacagatatt aagctatgcg agaaatagga cttctccttt  22140
tttttccgtt tcagctggta ctcctggtta atcaacagct tcgtcaacgg tgagtccatg  22200
tgcttccctg cttcagtact agtgtttcca gcaggcagcg atttaattgt tcttgcattg  22260
aaacccagtg tggcaagccc ccctgtgatt tgaggctaat ccctccccac cctgttctgg  22320
cacatgtgcg gtgcccaggg ctccccccag gctgtgagca gataaagccc tgcgtggctt  22380
cacaacagtg actggttctg agaaacaggt ccttgtacaa gcgacaggga gtgctcacac  22440
cagatgtggc agcccctcca cgccaggctg tgtggtgcag ccgcctggta tatgtgtcca  22500
tcgctgatga aaacagcatt gtgtggtgca tgactgttgt ctgttttctt catggaaaca  22560
aggaaaccta agcattaaaa caacaccatc cacgtctggt tccttagagc aaatggaagc  22620
accaggctct ggtgcacggc gcgccccctc ctgcagatgc agtgtgggga ccctgcaggg  22680
ccctgtgctc ggggccacat gtcctgggag gcccgcctgc cccaggtggc accttcagct  22740
gcatgggctg ctgtgtccat cccccagccc caccagacca gccctgatcg cagctttgtg  22800
gtctctttgg gaagtggtcc cgtgagcatt aagggcgagg gcctgtctgg tgcagagcag  22860
gtgggtcccg cactgccgtc ctccctggta ggagtcccac acctgacccc tggggcagga  22920
ccttgtgggt caggaggccg tgtcctcata gccccagggt gctccagtgc tctcactgac  22980
ttgaccccgt gggcagcagt tacactgatt aataaataga agagctttgc tctccaaagt  23040
tgtcgtagac tcttgataaa cttaccagcc agaaagctgc ttcacaccat gatggactct  23100
gaagttgtct ggatagcaga ccttgttttc tgcccactat gcatagacgt ggcagctcgg  23160
ccctccacac ctcgtgagtg ccgtctgtgc gtagatgtgg cagcccggcc ctccgcacct  23220
cgtgagtgct gtctgtcttt ctgcaggggt ctatgccttt ggtttcctct tcatgctgcc  23280
ccagctcttt gtgaactaca aggtaaggcg gtgtgtgctg cccgcggccc ggcccccgtc  23340
tcctgtgctg cccacagctg acctgggcct gtctctcctg tttcagttga agtcagtggc  23400
```

```
acatctgccc tggaaggcct tcacctacaa ggtgagtgtg acagccggtg aggaatccct  23460
tctcactgag cagagcgtga gcaagggcgt cttccagcca acagcattac tggggccatc  23520
tctgcccaga gtgcatctgc acctgtccct ttcattgaag aatattgagg aggctccttt  23580
aaaaaaaaaa gcgaagagct atagagtaac ttcagaccct gaaagactgg ggtggttctc  23640
tcacttgtca cagatttggt tttctttttc tttttagtg tttatgtttc ttcttagcac  23700
atgtgtcaag acacagaccc cctgtggctc agtaaccggt gcctggggac aacggattca  23760
ggcctcccag gcaggaatgg aagcccccat gggccgtggc cattccccgc tggcagagct  23820
gtggaggccc ccttggctcc gtgtgggatt agaagtgcct cggcattgca ggcggagctg  23880
agttaatggg acatgatttg cacttttctg aagtcaatta caagctccca gaggaaaggg  23940
caatgctcag gtggctctgc ccttggctct ccccttggct gtggtctcgg gcggctctaa  24000
ccttggctct ggtctcaggt ggctctgccc ttggctctgt ctcgggcggc tccagccttg  24060
gctctggttt caggccattc tctttgggtt ccccgatgtg ggagcctggg caagacccgc  24120
agtgtgtcgg gtgccagcag ctgtggggag cccatgaggg aacagagctc cgtatctcca  24180
cttgccggct ttctgctctt tttgttgttg ctgtgaggag ttccagttag ttccaagcat  24240
ctgccaaaag ccgttggctt ggttaggtta ccaaaaacag taggattcca gccccagcaa  24300
ctggggttca ccctcctccc gtctggccct gcaggctttc aacaccttca ttgatgacgt  24360
ctttgccttc atcatcacca tgcccacgtc tcaccggctg gcctgcttcc gggacgacgt  24420
ggtgtttctg gtctacctgt accagcggtg gtgagtgcgg ctgcgtatgc tcggccgttg  24480
ctccgtctca gcggcgtggc tgctgctgaa cggaatgacg gctttcaccg caccctgcgc  24540
ctgtttatcc atttgaggga aaagataatt tgcaggtggt ggtttttcct gtcttgccta  24600
aacttgggtt ccagttgccc atgatatgtc ctggcaagaa actgttccag ctctgtctcc  24660
tcactgtgct ttagaaatgc tcgtttctat gtgaattatt gatgagccac tgaaagcaaa  24720
tgtctctcct taagcgattt atttacctat tcacagtcat tgctattgag cagaacagag  24780
accgtagcat ggctaatcca tacttggcgc tagcctcgaa gtgtccagcc agcagtgtgg  24840
acctgcaggg cacaatgtca ctggggagct cactcacctc agcattggcc gcacccctta  24900
aaccagccac cagggcctct gaagactgca ttgcgtggac ctctcagctt ggccttcagg  24960
ttgaaggctg acggctgagg aaaaggcttt gtggaatttt ctaaaggcag aggttcaggc  25020
cccaccccgg gcctcggaat tttccaaatg cagaggctca ggccccaccc tgggcctccc  25080
gcttccctcc agggctgaca tctgccctct cagtcagcaa aacctccctc cagctctgct  25140
gtgccagggt aggagccagg gatctggggc tcccctcggg agggttgcat ctggaccact  25200
gcaagcactg ccctcacctc cagtgccggc cccagggcct tgtccagggg tcgaaggagt  25260
gtgtgtcacc cccaagacct gctgccaagt gtctcagagc ctcctggctg tgtcctttct  25320
ctggccctca aggtcccttt tcccatctcc ctcccccgac caggaggcca cctcacacac  25380
cacggctgtg acacttccct gtgcccttcc ctcagggcct ggggccatcc tactagtgca  25440
ggagagggat cctcttcccc caggccgtcc tggcgggtcc tgcctaggtc cggggtgccg  25500
gcccttgggg agcgcagtgc tcccgtcccc gccctgtctc cacactcaac ctcgccaggt  25560
gttcagagcc tctgtcccag ccagcatgag gctggcatgg ttctgcctgg tttaactctt  25620
tgttcgggtg cagttggcac atccacacag tggctcatgg ccgcccttgc ccagctctcc  25680
aggcctggcc gccggctgcc cccccccacc ctgttgctgt ctcgtgcagc ccctgcacgg  25740
gagctccagc ttgtgtcagc gggaagggct atttcaccat aagcaacact cacactcaca  25800
```

```
cggggcttgg ttcctgtccc ccgttcacca ttctcagatc ccccagctgg ccgcctgccc  25860
cctgcagagc ctgaggttgt ccaagccacg gagccccgga cgctgctgcg cctggtgtgg  25920
ttgtctcaac tgtgagccct tcaagtggct cccaagtcct cgcaggtggc ccggggcgtg  25980
cctgaaactg tgctgtactc aggctctgtg ttaatggctc cagacctgca aacggtgttt  26040
ggccaggatc acagggccct tggtgggcag caggtctgtt tttaagctga aaccctgtac  26100
ttctgttcgc ggccgtgtag agctgcccct tatgccacag cttcctcatc catacgtagg  26160
ggtgatgttg gcaaggcctc cggggcgctc aggatcaaag gcggcggcag tgtcctgcca  26220
agtgttcaca gctgatgaga cgtggtccct gaacacagcg gttcctgttc tgatcactcg  26280
agtctccgtg atgccaccgt tcccagaagg cagcccgtgc agcctccggg tccccccttc  26340
agccatggca gcccgtgcag cctccgggtc gtcccttcgg ccaagcttcc ctttccttga  26400
gagcagcacg ctggcctggc catgcagaac aaaacacaac tcagaaatcc ctcctcagcc  26460
ctcggcagta aaacttctga ggattcgact ttttagttaa tttgctcact gtggcagctc  26520
actggaaaat aaatcgagga tgccaagtcc tcctcttaga aaaatagccc ctgcagtggg  26580
gtttgctgat gtgctcattt gtgtcattgc aggctttatc ctgtggataa acgcagagtg  26640
aacgagtttg gggagtccta cgaggagaag gccacgcggg cgccccacac ggactgaagg  26700
ccgcccgggc tgccgccagc caagtgcaac ttgaattgtc aatgagtatt tttggaagca  26760
tttggaggaa ttcctagaca ttgcgttttc tgtgttgcca aaatcccttc ggacatttct  26820
cagacatctc ccaagttccc atcacgtcag atttggagct ggtagcgctt acgatgcccc  26880
cacgtgtgaa catctgtctt ggtcacagag ctgggtgctg ccggtcacct tgagctgtgg  26940
tggctcccgg cacacgagtg tccggggttc ggccatgtcc tcacgcgggc aggggtggga  27000
gccctcacag gcaagggggc tgttggattt ccatttcagg tggttttcta agtgctcctt  27060
atgtgaattt caaacacgta tggaattcat tccgcatgga ctctgggatc aaaggctctt  27120
tcctcttttg tttgagagtt ggttgtttta aagcttaatg tatgtttcta ttttaaaata  27180
aatttttctg gctgtggcat ttttcttgac ctggtataat gaaagtattt cggatatttg  27240
agtttaaccc ttttccagaa agtaatacat gatatggatt tatttatgca ttaaaagagc  27300
aaatttaaag a                                                       27311
```

```
<210> SEQ ID NO 2
<211> LENGTH: 538
<212> TYPE: PRT
<213> ORGANISM: Homo sapiens

<400> SEQUENCE: 2

Met Trp Ser Gly Arg Ser Ser Phe Thr Ser Leu Val Val Gly Val Phe
1               5                   10                  15

Val Val Tyr Val Val His Thr Cys Trp Val Met Tyr Gly Ile Val Tyr
            20                  25                  30

Thr Arg Pro Cys Ser Gly Asp Ala Asn Cys Ile Gln Pro Tyr Leu Ala
        35                  40                  45

Arg Arg Pro Lys Leu Gln Leu Ser Val Tyr Thr Thr Thr Arg Ser His
    50                  55                  60

Leu Gly Ala Glu Asn Asn Ile Asp Leu Val Leu Asn Val Glu Asp Phe
65                  70                  75                  80

Asp Val Glu Ser Lys Phe Glu Arg Thr Val Asn Val Ser Val Pro Lys
                85                  90                  95
```

```
Lys Thr Arg Asn Asn Gly Thr Leu Tyr Ala Tyr Ile Phe Leu His His
            100                 105                 110

Ala Gly Val Leu Pro Trp His Asp Gly Lys Gln Val His Leu Val Ser
        115                 120                 125

Pro Leu Thr Thr Tyr Met Val Pro Lys Pro Glu Glu Ile Asn Leu Leu
    130                 135                 140

Thr Gly Glu Ser Asp Thr Gln Gln Ile Glu Ala Glu Lys Lys Pro Thr
145                 150                 155                 160

Ser Ala Leu Asp Glu Pro Val Ser His Trp Arg Pro Arg Leu Ala Leu
                165                 170                 175

Asn Val Met Ala Asp Asn Phe Val Phe Asp Gly Ser Ser Leu Pro Ala
            180                 185                 190

Asp Val His Arg Tyr Met Lys Met Ile Gln Leu Gly Lys Thr Val His
        195                 200                 205

Tyr Leu Pro Ile Leu Phe Ile Asp Gln Leu Ser Asn Arg Val Lys Asp
    210                 215                 220

Leu Met Val Ile Asn Arg Ser Thr Thr Glu Leu Pro Leu Thr Val Ser
225                 230                 235                 240

Tyr Asp Lys Val Ser Leu Gly Arg Leu Arg Phe Trp Ile His Met Gln
                245                 250                 255

Asp Ala Val Tyr Ser Leu Gln Gln Phe Gly Phe Ser Glu Lys Asp Ala
            260                 265                 270

Asp Glu Val Lys Gly Ile Phe Val Asp Thr Asn Leu Tyr Phe Leu Ala
        275                 280                 285

Leu Thr Phe Phe Val Ala Ala Phe His Leu Leu Phe Asp Phe Leu Ala
    290                 295                 300

Phe Lys Asn Asp Ile Ser Phe Trp Lys Lys Lys Lys Ser Met Ile Gly
305                 310                 315                 320

Met Ser Thr Lys Ala Val Leu Trp Arg Cys Phe Ser Thr Val Val Ile
                325                 330                 335

Phe Leu Phe Leu Leu Asp Glu Gln Thr Ser Leu Leu Val Leu Val Pro
            340                 345                 350

Ala Gly Val Gly Ala Ala Ile Glu Leu Trp Lys Val Lys Lys Ala Leu
        355                 360                 365

Lys Met Thr Ile Phe Trp Arg Gly Leu Met Pro Glu Phe Gln Phe Gly
    370                 375                 380

Thr Tyr Ser Glu Ser Glu Arg Lys Thr Glu Glu Tyr Asp Thr Gln Ala
385                 390                 395                 400

Met Lys Tyr Leu Ser Tyr Leu Leu Tyr Pro Leu Cys Val Gly Gly Ala
                405                 410                 415

Val Tyr Ser Leu Leu Asn Ile Lys Tyr Lys Ser Trp Tyr Ser Trp Leu
            420                 425                 430

Ile Asn Ser Phe Val Asn Gly Val Tyr Ala Phe Gly Phe Leu Phe Met
        435                 440                 445

Leu Pro Gln Leu Phe Val Asn Tyr Lys Leu Lys Ser Val Ala His Leu
    450                 455                 460

Pro Trp Lys Ala Phe Thr Tyr Lys Ala Phe Asn Thr Phe Ile Asp Asp
465                 470                 475                 480

Val Phe Ala Phe Ile Ile Thr Met Pro Thr Ser His Arg Leu Ala Cys
                485                 490                 495

Phe Arg Asp Asp Val Val Phe Leu Val Tyr Leu Tyr Gln Arg Trp Leu
            500                 505                 510

Tyr Pro Val Asp Lys Arg Arg Val Asn Glu Phe Gly Glu Ser Tyr Glu
```

```
        515                 520                 525

Glu Lys Ala Thr Arg Ala Pro His Thr Asp
    530                 535


<210> SEQ ID NO 3
<211> LENGTH: 27311
<212> TYPE: DNA
<213> ORGANISM: Homo sapiens

<400> SEQUENCE: 3

gcggggccgg cgaatcccgc ggcgccaggt gggagcgggg ccggagcatg cggggcggcc      60

ggcggtctgc ggcgcgcggc gcattcgttc cccgcggcgg gtggcggtgg cgcgcggcgg     120

ctctccagtg agcggcggag cccggagcgg cgggctgggc gccgggcggg cggggctcgc     180

ggctgagagg cgggcgggcc gggggcgccg ggcgcggggc cgccatgtgg agcggccgca     240

gctccttcac cagcttggtg gtgggcgtgt tcgtggtcta cgtggtgcac acctgctggg     300

tcatgtacgg catcgtctac acccgcccgt gctccggcga cgccaactgc atccagccct     360

acctggcgcg gcggcccaag ctgcaggtga gcgtccgcgg ggccgggggc cgggcgggtt     420

ggggtggggg cctctcctcc aggccccaga cgtcgccttc ccgtcccagt tcggagctgt     480

ggccgcgcga gtcgagatgg aacctttcct ggttccccag cggccaggtc ttccgccctc     540

cagctggccg tgggatttga gtgcgtcctg ccagggcctg gccgagctga ctctcgacgc     600

cccctccttt ccagctgagc gtgtacacca cgacgaggtc ccacctgggt gctgagaaca     660

acatcgacct ggtcttgaat gtggaagact ttgatgtgga gtccaaattt gaaaggtatg     720

ggcgtaggac aaaatgccag tgaaagggaa aacattactc atgttcagat tgtttaaaag     780

ttagctttct gtacataaca tgtttatttt agagaactag tcttaccgaa tgtcttgaag     840

tggtagaata tcctaactgg aggcctatgc gtggcctgta aacattcagc ctggaaggtg     900

acaggtgatg aatgtcgttt aagaagtagt tctcagcaga gtgtgatggc agtgggatgt     960

cctggacggg gaggctccga aggagcaggg gccacgcttg gtgaaccagt ggagagcaga    1020

caactctgca gtttcactac cggggaccaa cttgtctttt cctggtggaa gtagttcgct    1080

taagttactt gtgagggaaa agagatgagg atagaggaag caattttgta gaaaatcata    1140

aataagtgac atgtgacgtt agaatagatc aatgtccaaa tatgtagagt atcttaaaaa    1200

ttacatctga catggcctaa tttttttaa ttgaataagt atacttttaa atatgatttg    1260

cttctcacaa gtcaaccatt tcccttcatt gcctgggagg tatctgagga gagaataatg    1320

aaagtttgag actcatgctg gactccacgc cctctaggca gccagtccct gggggtagct    1380

ggaggcgctg gcaagccggt ttctgcctgg cctctttagg cctgtgacct caagccagtt    1440

cctgccctct ctctgcctcc atgaagggga ggccagaagt gctggtgacc aagctgcccg    1500

ctcggttgta gctgcccaca cctttcaaaa atgctcagga ttcatctgca ctgggtttaa    1560

tttcccagac atgaatactg cctcttccgt gccgggccgt gtaccagtta ccaaggacag    1620

ctagtgaggt tttccatttg acctggcaca gtgtcagcct ggaggaagtg gggagaatga    1680

gcactcttaa cacagctccg cctcaagtgt ctccaagtgc acattccacc agaaatacac    1740

agccctgcac cctctgcctg aagagagaca cttaagatgt cctggtggag acatactctt    1800

tcctgggtag tgaggagcca tagatgcctt tgtgtttttc attacaactt tggccgtaag    1860

attttttttt ttttttgaga tagagtcttg ctctgttgcc aggctggagt gcagtggcgt    1920

gatctctgct cactgcaacc tccggttccc gggttcaagg gattctcctg ccttagcctc    1980
```

```
caaagtagct gagactacag gcacccgcca ccacgcctgg ctaatttttt tatttttagt   2040
agagacaggg tttcaccatg ttggctgggc tggtctgaaa ctcctgacct cgtgatctgc   2100
ccggctcggc ctcccaaggt gctgggatta caggcgtgag ccgccgcacc cggccaaccg   2160
taagattttt aaggagaggc cgggcacagt gactcatgcc tataatccca gcagtttggg   2220
aggccaaggc gggaggatca cttgagccca gcagttcaag accagcctag gcaatgtgac   2280
aaaaccccat ctctacaaca gttttcaaag ttagccaggc atggtggcac gcccacctgt   2340
agtcccagct actcgggaga ctgaggcggg aggtcacttg agctcaggag gttgaggatg   2400
cagtgagctg tgattgcacc cctacacttt cagcctggtg acagcgagac cttgtctcaa   2460
aaaagagact tttaaagagg aagaagaact catgtaaccg taaacaggtg gaatgcgagg   2520
tttttccatg gggctgtagt atggacgtcg ggccctggtg tgcgggtgaa gagccaggca   2580
cctggtccga ggcctacagt tgtagcagct cgccgggcct ttcctcagct cgtgctggat   2640
gccacacagt caggactgac agccttgaaa gtcagtcctt tgtggctgat catcttttta   2700
tccttaaaac tacaacaccc aaaaaaacta cccacattaa atttctgagg ttccagtagt   2760
gtgggccgag gcacctggag ccctcgtggc tgctgccctt cccttctgtc gcttcggagt   2820
tgggtgattc agtgtgtgtg gtcagctggt accctggcca ggcccagaag ctgctttcca   2880
tctggctgct tcagccttgt ggcctcaggt gggttattga cctctcagcc tcctgagatg   2940
gaggcaggaa gtgcgggccg ttttgctttc ggctgtaggc gcccacacct gtgccgagtt   3000
ctcaggacgc gcacgcgtgc gcgtgcacac acacacacac acacacacac acacacgact   3060
cgtaaagccc tgggcaggtg ggtttcattt ttagtacttc tgagctaaaa ttagtttatt   3120
gaagcagctt tataaaggta tttgaatagg ttctagagac ccagaatata atatgtatgt   3180
agtggaaatg attgttctgt ttcaggacag ttaatgtttc tgtaccaaag aaaacgagaa   3240
acaatgggac gctgtatgcc tacatcttcc tccatcacgc tggggtcctg ccgtggcacg   3300
acgggaagca ggtgcacctg gtcagtcctc tgaccaccta catggtcccc aagccagaag   3360
aaatcaacct gctcaccggg gagtctgata cacaggtgag ggtcttcatg ggttactgat   3420
aacaggctgt gcctctccgt cagaacggac atgtctttct ccacacaggt gggcgatgtc   3480
tagggctcca gtgactttgt tgggagtaaa gccaaaagcc attggaatgt tactggcgtg   3540
catttctgac tttcagctga atcatatcca tgagtttgca gacaagtttt atctaaaatt   3600
agggacagtt gaagtgatcg ctggcattct cgatgcagag tccctcgggg aatgggccct   3660
ctcagtctct gggggcacct actgcacctg gtgggatgga gcgctggtcc tgcagagctg   3720
gcctgcagct tctcaccagg agctctgggg atgagagctg ggctcattct gcattctgtg   3780
taggactggg ctattcctag atgtttattc taagaatgta attggagatc atggaaaagg   3840
tagaggtaca agttgtagtt tgtacatctg tagaaaggtg tatgcgcaaa taaaaactgg   3900
aagtcactta agtgatcatg aatacaggcc aaggataaag caagggaatt ctgacaccca   3960
cctttgtgtt gagtggaagg tgagataatt tacaaaacaa ggccgggcgc agtggctcat   4020
gcctgtaatc ccagcacttt gggaggctga ggcaggtgga tcacctgcag tcaggagttc   4080
gagactagcc tggccaacat ggtgaaaccc cgtctctact aaaaatacaa aaattagctg   4140
gatgtggtgg cacgcgcctg taatcccagc tactcaggag gctgagggag gagaatcgtt   4200
tgaacccgtg aggtgagatg atgccactgc attccagcct gggcgacaga gggagactct   4260
gcctcagaaa aatttacaaa acaagaaaga tggcagcttt ccaggaagag gctgtgaaat   4320
tgttccagac agagagaaag agaggtctct cggagttgat ggggttttga aagccctacc   4380
```

```
aacacctgct cctgcctctc cccagtttgc atctgtctcc ttaggaacat ccctcacctg   4440
cccctctccg tgtcccctca tctggggccc ccatccctcc tctccagtgt cctgaaaagt   4500
gggtggggtg atgggcatgt agcatgtagc gcaggaagcc tcccttgcag gtagcaaatg   4560
tgaggaggtg tggaaaaccg tttgtaatgt aaattatcgc taaactgcat ctttaggtag   4620
gaaatgggtg aggcgatagt gcttcctagg atgtatcaga tctgagccga gctaagattt   4680
ccctgtcagt ccatgtcctg tttaacttca tgtaagagcc gtgtgtaatc ctcagtatgt   4740
ctcctttagg cagccccaca tgcttggttt tagaagctga ctccctctca gtctccttac   4800
agccacaggg ctgtgtgagc cctggacttg cacagtcttc tgccaaggtc agggggctct   4860
caccctctca acttctgaga agtgggccca cttagtttga ggacctcaaa aaaggaattg   4920
gtgaagtccg tgaccacatg ttgcaaagca gcacccccctg gcttccgtgg agataaggat   4980
ggggggctgt ttggcgagag tctggcggaa ttggcagctg tggggccgct gtgccctctc   5040
tgctgggctc tcccccggtt gtgcctgtgc gtggccatct gttcacaggt tagggtgccg   5100
accctgctgt ccgggcgcgg tttttccatg tgcgtggcca tctgttcaca ggttagggcg   5160
ctgaccctgc tgtcccgggc acagtttgcc cgtctgtgtg gccatctgtt cacaggttag   5220
ggcgctgacc ctgctgtccc gagcacagtt tgcccgtctg tgtggccgtt ctcttcacag   5280
gttagggtgc tgaccctgct gtccgggcgc ggtttttcca tgtgcgtggc catctgttca   5340
caggttaggg cgctgactct gctgtcccgg gcacagtttg cccatctgtg tggccatctg   5400
ttcacaggtt agggcgctga ccctgctgtc ccgagcacag tttgcccgtc tgtgtggccg   5460
ttctcttcac aggttagggt gccgaccctg ctgtccgggc gcggtttttc catgtgcgtg   5520
gccatctgtt cacaggttag ggcgctgacc ctgctgtccc gggcacagtt tgcccgtctg   5580
tgtggccatc tgttcacagg ttagggcgct gaccctgctg tcccgggcac agtttgcccg   5640
tctgtgtggc cgttctcttc acaggttagg gtgctgaccc tgctgtccgg gtgcggtttt   5700
tccatgtgcg tggccatctg ttcacaggtt agggcgctga ccctgctgtc ccgggcacag   5760
tttgccagtc tgtgtggcca tctgttcaca ggttagggca ctgaccctgc tgtcccgggc   5820
acagtttgcc cgtctgtgtg gccgttctct tcacaggtta gggtgctgac cctgctgtcc   5880
cgggcacagt ttgcccgtct gtgtggccat ctcttcacag gttagggggc tgaccctgct   5940
gtcccgggca cagtttgcct gtctgtgtgg ccgttctgtt cgcaggttag gggctgacc   6000
ctgctgtcct gggcatggtt ttctgtccca gcattggcct ctgttttcct cacttaacag   6060
cagatcgagg cggagaagaa gccgacgagt gccctggatg agccagtgtc ccactggcga   6120
ccgcggctgg cgctgaacgt gatggcggac aactttgtct ttgacgggtc ctccctgcct   6180
gccgatgtgc atcggtacat gaagatgtaa gtggggcccc agagctggag cgccgggggg   6240
agggtgctgg gaccctggct ggccagaact cgccagcagg tcactcctgc accgtggagt   6300
cccctctgtg gggaggcact tgctgcccgg gcctcccagc tctttcccac ttcctcattg   6360
aggttgtgct gctaccacag ggctggaagg ggggagaaag gaattcaagc tggagcatcc   6420
tgccctttgc tcctggctgg cgaaggcttc catggagaga aaacggaagg cgctgatggg   6480
aacgggttgc tttgctcccc ttgtgatttt ttaacttggc ttatttagat ttacttaaaa   6540
gttaatcttt agattattta gtatcacttg ccatcagtta aatacaatta ttggaattca   6600
cgtgtttggc cacctgagct cacctcgtct ctcccatgtg ttggggatcc cccccccaac   6660
tcctgcgcca cagctccgcc tcccaggtgg ctgcaggtga ctcgcccttc caagtgtagt   6720
```

-continued

```
ggccacatcc tgggattgct ccgtgtcagt gcatcctggg attgctccgt gtcagtgcgc   6780
agagggccct gggttctgct gtacggccgt gtccctgtaa ttccccgct cctagtggcc    6840
gtggaggcat tttcccacct gtggccatca cttcctgggg agcgggtctc acaagcgtgc   6900
atatgttgtc aggctctctg cttccgtttg gggaggctgt gccctggggt cattgtgact   6960
gagaagcagt tgagggtggt gctgggggca cttctctggg gtaaacccag tgtctggatg   7020
tgttcattca ttgaaaggta aaagccttgg tgctgacttt ggaaagttgt gctttaatcc   7080
caggatccag ctggggaaaa ccgtgcatta cctgcccatc ctgttcatcg accagctcag   7140
caaccgcgtg aaggacctga tggtgagtga cacctctgcc cgctggttgt gcagctggcg   7200
agacactgac cccaagactg gccccgcagc ccctgcaccc taatggaccg ggccattgct   7260
gacatttgac acggtgcttt tacccgtgct gggaagcact gccttcgagt gtgcgagggt   7320
tgtgacaggg gggccctggt ggtgtgctgg gtttgccgtt ggctggctgc ggggtcctgc   7380
tgagcctctg gactgtcact ggtgaaaggc ccctggaaga ttgtttatgc agcgcataga   7440
gggcagcgct tagagagcag gcacatgagc accgtgtgaa acagcgtctg cgtgtgagct   7500
cctggtgtgc catgtagatt aattcacagt atcctgagca aactcctgct ttccccacca   7560
gggctggtcc tgcacaggcg gccagaggag cgggtgacag cccttcctcg gagctggagc   7620
ccccggggtg gcccctggca aggcggaagg cctttgcgaa tagaagtggc tgctctctgg   7680
gctctggcgc cctgtgatta cggcagtga cagcgcctgc tctcccatag ttgctttgag    7740
aggagatgaa atgtggccaa cctttggcca gtattgagac tcacagaagc agttaatatt   7800
taatgtctct tactgcacat gaggcactgt gctaagcact ttgtgaatct ttccgtaatt   7860
gtggtgctgg gagctgtggc gttgtttcac ggatgaggtt atttggggtt cagaggtgaa   7920
cgctcagctg gggccctgca ggatcgctgc cctgccctgc ctccctgcaa gccatcactg   7980
tcactccgga tcacccacta ggagccggcc acttccactt aaggctctcg gcacctctga   8040
cctctgaggc gggccctttc cccttttttg ttgaagagga aacagtcctg ggagagcag    8100
agggcttgct agcggggggg tgcagctggg aaacggagaa gcgagcacct ggctgctttg   8160
atctctgccc aggccctgct gcctcctcct gactgcggct ctcagaacag tccccctgta   8220
ctgctgttcc ctcagacccc ttgcagtccc taacatactg cctccttcac ttctggggtc   8280
actgattgct cctatacaac ctgcaggctg gggctgcac aggcagtggc tggcgagcag    8340
gtctggcgct gcagcctatc cctgagtagt ttctctgtcg gcccctgcaa ttccaacctc   8400
tttctctgtt tgctggagtt tgctggtgtg ctgctgacaa acctcaggac agcaagttct   8460
gctaaaatgc cccatacaga gctgtgtgag ctgtggcacc agctcgtggt cacctcttgt   8520
gaagcctcat gccgctgact ccttgcaggc attcaggaga tggtggacag gggcaggcag   8580
ctgcagaagg ctgccctgtg tgtctgtctg cagatctgtc ttgttagagg cccggggcag   8640
gctttgcggc gcagctgtgc cagtggtggc ctgcgttcca gtggttatgg agacacgtgt   8700
gccgacagca gcttttcccc caaatcacag tctctctcat gtgtcgctgt tgctgtgtct   8760
cacttggggc cagattcgag aggtgctgtc ttgagagagg aagcaggcag ctgggatgca   8820
gcaggtgcag gaagtcggca ccttctgtgg ctgggcccag cactgccaga tggaggaggc   8880
agtgacaccc ttcggacacg cttggcagct cgaggggtgc ctggaggcca ccatccatgt   8940
gcactgatgc cacttggcta cgtggggcgc cctgacagcc gctctcaggg caacctggca   9000
cctgctggtt gtggctctga ttccaccaca ccctgacacc agcagtgccc gccatagcag   9060
agcaggtgga ttagagcaca gccctcgctg gatgttccag cacgtggagg gtggcgggtc   9120
```

```
agggcttgag gcagggcagg tggattagag cacagccctc gctggatgtt ccagaacgtg   9180
gagggtggtg ctcaccgggt gtggtcactg cccacgtgct gtagggtgtg ggctcgcgct   9240
tgtgaacccg ttcctcaccc tcctacctcg gcaccctggg acctggccca cagcctgtgt   9300
gcgtgaggcc ccggcaggct gcaggactaa gctcgtggtt ctgagaccta cacatccacc   9360
ctactgcccc tgctagcttt gcgttccaga agctttctgt tgtccccacg gccacccccct   9420
gctctgtgct ttaggccctg aggcactttg cccatgtgct gcagggctgt gcttgtcccg   9480
tggtctccaa ctcttaggac aggccagggc tctgcaggcc aagctcagcg ccgtatgctg   9540
cgccatggag tcctagcagc tgggtggcaa gcaccacctc cggggcacca ggacttgtgc   9600
ggcttaaaat tgaaggggca cgtgcagcaa aacagaccag gcactgctag cgctgctgag   9660
ctcacggggt cctggtgggg gtgggaacct ccctgtgctg gaacgcagca cgctggggcc   9720
tgaggcctgt ggtgacagaa ggagggaccg ggggatgctt gctgggccca gtcatggctg   9780
acctggggcc acacagggat gggaaggggg atggcagggt tggcgagggc tgccaggcag   9840
ctgggtgcaa gggtatgagg gcagggccct cagtgtggct ttcttcatca ggtcataaac   9900
cgctccacca ccgagctgcc cctcaccgtg tcctacgaca aggtctcact ggggcggctg   9960
cgcttctgga tccacatgca ggacgccgtg tactccctgc agcagttcgg tatgtgccgc  10020
acacggccgg cgcctgggtg aggccgccct ggagcccctc gggcatccaa gtgcgaatcc  10080
tgacacaggc cggggcctcc tcgcctcctg ctgcagatcc ttgcacagac gttgaatcag  10140
aggctagcag cgcctgcctc acttctctcc ttggagatga cctggttgat tgtctggaaa  10200
ttggctttat taagaacata atatgtgaaa tgccatgagt ttggtcaaat gaaccttaac  10260
tgttgatgag atttattttt attgtttgtt tgtttgtttg tttgtttgtt ttgagacaga  10320
gtctcgctct gttgcccagg ctggagtgca gtggcacaat ctctggttac tgcagcctcc  10380
gccccccgga ttcaagcgat tctcgttcct cagtcccccc agtagctagg attacaggcg  10440
cgtgccccca cgcccagcta atttttgtat ttttagtaga gatggagttt caccatgttt  10500
accaggctgg tcttgaactc ctgacttcaa gtgatctgcc tgcctgagat tcccaaagtg  10560
ctgggtttac aggcatgagc cactgcgccc ggcctaaatt tttatattga aaactgtatt  10620
tgtaatgtta ggtaagattg acattgcctg ttttatattg tatgtttttt tttccttgac  10680
agggttttca gagaaagatg ctgatgaggt gaaaggaatt tttgtagata ccaacttata  10740
cttcctggcg ctgaccttct ttgtcgcagc gttccatgtg agtcatccac cgggggggctt  10800
gccgcaggca cttggggggc tccctgggcc ccgggcctcc tgcaggggtc ctggacctgg  10860
ggtttgtggg cgccgtccag ccctgtggcc ctcaagtgtc cactcccatc actcagcagc  10920
cagcacgcct gacaccaggc gaccattgtc ccagtgggcg gtttctccca gttctgaaaa  10980
gggagggacc ataaagctcc gtccacagcc ttggcgactt gggctgtgct ggctttgggg  11040
gcggttttga aaaggatcca gggtactctg agcagtgtcc acaccaatga gatgaatagg  11100
tgcaggcatc tcactctccc ctgcccaggc cccgaccccca tgcagagcca ggggcggagc  11160
tgggcagcct ctagcagaaa gtagttctct tgtataaatt ctaacacact gatttttaaa  11220
tgtaaaaagt cagtcctgtg tgtatacagt agttccccct tacccgatgt gtatacagta  11280
gtccccccctt atcctcatcc ggtgtgtata cagtagtccc cccttatcct catccggtgt  11340
gtatacagta gtccccccctt atcctcttgc ggtgtgtcta cagtagtccc cccttatcct  11400
cagccggtgt gtatacagta gtccccctta tcctcatctg gtgtgtatac aatagtccct  11460
```

```
catcctcatc ccgtgtgtat acagtagtct cccccttatcc tcatccggtg tgtatacagt  11520
agtcccccct tatcctcatc tggtgtgtat acagtagtcc cccccttatcc tcatctggtg  11580
tgtatacaat agtcccccct tatcctcatc caatgtgtat acagtagtcc cccccttatcc  11640
tcatcccgtg tgtgtataca gtagtccccc cttatcctca tctggtgtgt atacagtagt  11700
ccccccttat cctcatgtgg tgtgtataca atagtccctc atcctcatcc cgtgtgtata  11760
cagtagtctc cccttatcct catctggtgt gtatacagta gtccccccctt atctggtgtg  11820
tatacagtag tccccccctta tccggtgtgt ctacagtagt cccccccttat cctcatccgg  11880
tgtgtataca gtagtccccc cttatcctca tccggtgtgt atacagtagt cccccccttat  11940
ccggtgtgtc tacagtagtc ccccccttatc ctcatccggt gtgtatacag tagtcccccc  12000
ttatcctcat ccggtgtgta tacagtagtc ccccccttatc cggtgtgtct acagtattcc  12060
cccccttatcc tcatcccgtg tgtatacagt agtcccccct tgttctcatc cagtgtatat  12120
acagtagtcc gccccttatc ctcatctggt gttatacagt agtccctcat cctcaggggg  12180
tgtgttcaaa gaccctcatt ggatgtctga atatgtgtat caaataacgt aatgaatgaa  12240
tatatgtatt atgtaatggt tttgataaag ttcaatttat aagttaagca cagtaagaga  12300
ttacccacaa taactggtaa cagaaacagg acaggacagt gtgataaagt tacgtgggtg  12360
tggtctcact ctcagaatat ctgtctcatc gcactgctcc gtgctaaccg aaaccatgga  12420
cagtaaacca tgggtaaagc aaggctgctg tgctcttact gttgttcgtg gagctgagct  12480
gctagggaga gccatccttg tggctgttag gctggcctgt ggttaggcgg cacccaggag  12540
tgcggccggc actggttctg agtgcctggg agtttggctg ccagtcaagc taaaactttc  12600
caaagccgta ctagagaatt aaacgatttt tattaaaagg tcagtgtctc taaggatgag  12660
atcatgcatg gttaggtttt tttaagtttt ttttggagac aggtctcagt acgttgccca  12720
ggctggtctc aaacccctgg gcttaggtgg tcctttggcc ttggccttgc agtagctggg  12780
atcacaggca tgggccacca tgcccagccc ttgcgttttt agcacagttg agagatgagg  12840
ctgccctgag tgggcacaac ccgagagcag gggtgcccag ccaggcccat gatccagggg  12900
aatccagagc ctccaattgc ctgggggcct ttccagcagt tcaagtcaaa ggtacgtatt  12960
atttcagaag tgcccctgca aagcccgcct gggcactcta ggttctgaca tggcaggcca  13020
ggcgcgtaga ggcatgggtc ccgagtgtag acacttatcc tgatgcatcc tgaggctgag  13080
tacacctgca gtctcacggt cacacacgaa gcctctatct ctgtctcaca ggagatggaa  13140
acagcaggag atgtgagttg ctgtcgtgtg tgttctctct agcttctctt tgatttcctg  13200
gcctttaaaa atgacatcag tttctggaag aagaagaaga gcatgatcgg catgtccacc  13260
aaggcaggta ggccccccga gcgtggccct gctcagatac tctgccccag ggagctcact  13320
ggagcctgcg gtagagggct gcctgcctca ctgctggctg cagacacagc cccgggtgtg  13380
tgcttggctc ttgagaagcc tctgagacca ggcaccgtaa agcccaggga gccgttgcgg  13440
caattgtggt gggaccatca gaggctgcac ggctcagggc ctccagcggc tgcacagctc  13500
agggcctggc tgcggactct ggcgtgcatg gggtctgggt ctgggctgtg gagagtgaga  13560
tgcatggacc tctcgagcct tcccggctgc tcatgggcgc tgagcagggc tggggcctca  13620
catcccctgt cttggttccc tcgccccgtc ctcccgccgg tgttccttcc ccgaccagcg  13680
caggcctggg cgtgtggggc ctgccaggtg atggcagtta ataggcccgt ggtgctgtgc  13740
ccagcagtga caggcagtgt gcagctgtta ggtagggcag tcagggaccc ctgaggccag  13800
gcagcccagg caggaggcct gccaagatct gggaccagtg ttcctggcca agggtgcctg  13860
```

```
ccgtggttta aggggcccaa gtgagtgagg ggtcctcctg accttgcagg ggtggaggtt  13920
gtcacagtgg ggtggggagc ggcggtctgg acaggggcga gtggttgatg ggtgtgagga  13980
cgaggagtgg gtgtgtcctg ttggttagga gtgaggagca tttggctcca gtatcagacc  14040
cgaacaagtt gtttttctcg catggaaaag acgcccaagc aggtggccct ggctgcctgg  14100
gggccgtgcc gtgttctgcg ttgttgtctc ctaaccctaa tgcctttcct ggcgtcctgg  14160
gttggagtgg ccagcagaca gtggctgtgg ccttgaccac tgtttgtcct gtggctccat  14220
ggatctgctt cccctgcttg ccctcagggc ttgcaggagg aggaagacgt gttgaataag  14280
ctggagtggt tcttaaggta cagctgggga ggaaacaaat ccagacttga aaagccacgc  14340
acttatcaca gaactggcat aagacacgcc cggaagcaaa gctgtgctgg ccccgtcatc  14400
cgacctctgc ccacgttcca tgctcatttg caagtgtggc tcagacacgt gtttgtggag  14460
ctggtgtggg gccagctgtt cagttcagca gccttccaaa cactttccta gctgctgaat  14520
gcttcattgt tctttttaaa cggggtgacg tggactgggg agtacctgaa gcttcttggg  14580
cgtggtgggt tgggatgggg gactgggggt atgtgtgtga cttggggaac acaggtgggg  14640
tctgccctgc accccctccc agcccgacca tcctgtcccc agtgctctgg cgctgcttca  14700
gcaccgtggt catctttctg ttcctgctgg acgagcagac gagcctgctg gtgctggtcc  14760
cggcgggtgt tggagccgcc attgaggtga gttccgggca gtgacctgaa ctgtctgagg  14820
tccatgtgcc tccacgcact caggaaaggc tttcagcccc gggacctgag accttctgtg  14880
gaagcctgtg tgcttgttcc cgatggcctc agtgttctgg aagctgtagg atggcaggca  14940
gtgggtgtaa aggctttgaa caagtggaga gcaaggaaat gcgtgttcgg gtggtatcag  15000
ctcatgaggc tctgtccacc aagcagtggt gagtcctgag gccctgtcca ccaagcagat  15060
agtcctgagg ctctgtccac caagcagtgg tgagtcctga ggccctgtcc accaagcaga  15120
gagtcctgag gccctgtcca ccaagcagag agtcctgagg ctctgtccac caagcagaga  15180
gtcctgaggc tctgtccacc aagcagagag tcctgaggcc ctgtccacca agcagagagt  15240
cctgaggccc tgtccaccaa gcagagagtc ctgaggctct gtccaccagg cagagagtcc  15300
tgaggccctg tccaccaggc agagagtcct gaggctctgt ccaccaagca gagagtcctg  15360
aggccctgtc caccaggcag agagtcctga ggccctgtcc accaggcaga gagtcctgag  15420
gccctgtcca ccaggcagag agtcctgagg ccctgtccac caggcagaga gtcctgaggc  15480
cctgtccacc aagcagagag tcctgaggcc ctgtccacca agcagagagt cctgaggctc  15540
tgtccaccaa gcagagagtc ctgaggctct gtccaccaag cagagagtcc tgaggccctg  15600
tccaccaagc agtggtgagt cctgaggccc tgtccaccaa gcagaggcct gaggccctgt  15660
ccaccaaaca gagtgttttc atgtgcttga gaaatcccac catgtgcaaa gcagaggtgt  15720
aaaccgtggg gccttgagag gctcgtgctg tggctggaga tctgagcaca gcggccaggt  15780
aggcactgac ggaaatcact cggtgccctg tggtccagcc ttggttgttc cggagctcag  15840
aaaagccggc caaaagggag cctcgtgggg caagaccagc tcaggagcaa acccttgagg  15900
ggggcgatgg ccttcagggt gagagggccc aggcttaagc ctagctcctc actgagctct  15960
gtgccacacc ggcaggagcc ggagtctgag gtctctgcag ttggtggccc acctgtgggt  16020
gggggcctct gcggccgtca tgcctgtaga ggaggagctg gatgcaatgt ctctgtagag  16080
gaggagctgt atgaaatgtg tctgtagagg aggagctgga tggaatgtcc ctgtagagga  16140
ggagctggat gaaatgtgtc tgtagaggag gagctggatg gaatgtgtct gtagaggagg  16200
```

```
agctggatga aatgtgtctg tagaggagga gctggatgca atgtgtctgt agagcaggag  16260
ctggatgaaa tgtgtctgta gaggaggatc tggatggagt gtccctgtag aggaggagct  16320
ggatgaaatg tgtctgtaga ggaggagctg gatggaatgt gtctatagag gaggagctgg  16380
atgaaatgtg tctgtagaca aggagctgga agaaaactgt ctgtagagga ggagctggat  16440
gaagtgtgtc tgtagaggag gagctggatg aaatctgtct gtagaggagg agctggatga  16500
aatgtgtccg tagaggagga gctggatgaa atgtgtctgc agaggaggag ctggatgaaa  16560
tgtgtctgta gaggaggagc tggatggaat gtgtctgcag aggaggagct ggatgaaatg  16620
tgtctgtaga ggaggagctg gatggaatgt gtctgtagag gaggagctgg aagaaatgtc  16680
cctgtagagg aggagctgga tgaaatgtgt ccgtagagga ggagctggat gaaatgtgtc  16740
cgtagaggag tagctggatg aaatgtatcc tgtagaggag gagctggatg gaatgtatcc  16800
tgtagaggag gagctggatg gaatgtgtct gcagaggagg agctggatga aatgtgtctg  16860
tagaggagga gctggatgga atgtgtctgt agaggaggag ctggatggaa tgtgtctgta  16920
gaggaggagc tggatggaat gtgtctgtag aggaggagct ggatggaatg tgtctgtaga  16980
ggaggagctg gatggaatgt gtctgtagag gaggagctgg atggaatgtg tctgtagagg  17040
aggagctgga tggaatgtgt ccgtagagga ggagctggat ggaatgtgtc tgtagaggag  17100
gagctggatg gaatgtgtct gtcgaggagg agctggatgg aatgtgtctg tagaggagga  17160
gctggatgga atgtccctgt agaggaggag ctggatgaaa tgtgtctgta gaggaggagc  17220
tggatggaat gtgtctgtag aggaggagct ggatggaatg tgtctgtaga ggaggagctg  17280
ggtggaatgt ccctgtagag gaggagctgg gtggaatgtc cctgtagagg aggagctgga  17340
tgaaatgtcc ctgtagagga ggagcaggat gaaatgtgtc tgtagaggag gagctggatg  17400
aaatgtgtct gtagaggagg agctgggtgg aatgtgtctg tagaggagga gctggatgaa  17460
atgtgtctgt agaggaggag ctggatggaa tgtccctgta gagcaggagc tggatggaat  17520
gtccctgtag aggaggagct ggatggaatg tccctgtaga ggaggagctg gatgaaatgt  17580
ccctgtagag gaggagctgg atggaatgtc cctgtagagg aggagctgga tgaaatatgt  17640
ctgtagagga ggagctggat ggaatgtgcc tgtagaggag gagctggatg gaatgtgcct  17700
gtagaggagg agctggatgg aatgtgtctg tagaggagga gctggatgga atgtgtctgt  17760
agaggaggag ctggatgaaa tgtccctgta gaggaggagc tggatggaat gtgtctgtcg  17820
aggaggagct ggatgaaatg tgtctgtaga ggaggagctg gatggaatgt gtctgtagag  17880
gaggagctgg atggaatgtg cctgtagagg aggagctgga tgaaatgtgt ctgtagagga  17940
ggagctggat ggaatgtgtc tgtcgaggag gagctgggtg gaatgtccct gtcgaggagg  18000
agctgggtgg aatgtccctg tagaggagga gctgggtgga atgtccctgt agaggaggag  18060
ctggatgaaa tgtccctgtg gaggaggagc tggatggaat gtgtccgtag aggaggagct  18120
ggatgaaatg tgtccgtaga ggaggagctg gatgaaatgt gtccgtagag gaggagctgg  18180
atgaaatgtg tctgtcgagg aggagctgga tgaaatgtgt ctgtcgagga ggagctggat  18240
gaaatgtccc tgtaggggag gagctggatg aaatgtccct gtagaggagg agctggatgg  18300
attgtccctg tagaggagga gctggatgaa atgtccccgt agaggaggag ctggatggaa  18360
tgtccccgta gaggaggagc tggatggaat gtccccgtag aggaggagct ggatgaaatg  18420
tgtctgtaga ggaggagctg gatgaaatgt gtctgtagag gaggagctgg atgaaatgtg  18480
tctgtagagg aggagctgga tggaatgtgt ctagaggagg agctggatga aatgtgtcgg  18540
tagaggagga gctggatgga atgtccctgt agaggaggag ctggatgaaa tgtgtctgtg  18600
```

```
gaggaggagc tggatgaaat gaaatgtgtc tgtcgaggag gagctggatg aaatgtgtct  18660
gtagaggagg agctggatga aatgtgtctg tagaggagga gctgcatgga atgtgtctgt  18720
agaggaggag ctggatggaa tgtccctgta gaggaggagc tggatgaaat gacgctggag  18780
ctccacaggc agggtccctc cataggtacg agtcacagtg ccgtgcccgg ctctggcacc  18840
cgtcctgagc tccgtgggtg atgccttcca agcatttagc catgaggtgg cggctctcag  18900
agcggtccca aaactggctc cagggctgcc cgagtggcag gcagaagtag gtgggggctt  18960
atttgggtgc aggcagagtg gcgtaaagaa ctgccctcac atgctgtttt tgttgtccgc  19020
tgggcggtgg ctgtgcagcc cacctgacca ggtacgcctg ccgtgtgtgg gttagaggcc  19080
caggtccagc ctccagcgct ctggcctgag ctgtgggagg gacaggaaga ggacagtggg  19140
ctgcgcgggg ccatgggcag caggtcctac ccgttactgt ctgggtcgtt cattcgtggc  19200
tcctggcctt cgaatattaa aggaactatt tcctgatttc tcccctcagc tgtggaaagt  19260
gaagaaggca ttgaagatga ctattttttg gagaggcctg atgcccgaat ttcaggtagg  19320
atttagttgt aatggctgaa ccccaagcct ctctgaagag tgtgattttg ccccctgtgc  19380
aaagagtaag atggccatct gcagatgagt cactgcgggc ctctgtcagg ggagcctccg  19440
tggtggaggc agcactggtt tctgatcgca gccactctct tcgcctgagg attccccggt  19500
catataccta gttctgaccg tcttcagtgc agacggcagc acttctgggc ctgagccggc  19560
ctctgggagg aaggatgctg gctggccagc acgtgtgctt cgttttggca ccttgtccag  19620
aggcgctccc gaggctggtg ctgactgggg tccgtacagt cctggcagtc ctgaagtgag  19680
tgagcccctg ccctgagctg gtggctgccc cagtgcctgg gcgcccataa ggcccctagg  19740
cagatgaggg ctggggcaga gctggagttg aatctcagtg cccacggatg gaccttgatt  19800
gaggcggggc cctcagcagt cacaggctga gattttccat gctgtgggca ggggggtcag  19860
gaagcccagc acacgcagcg cagccactgt gttccacctt gccccatggc tcccggccgg  19920
ctggttcgga gcagtgttgg ctgtgcctgt gtgctctgca gtgttctcac tgaagcggtg  19980
gcactgaaaa ctgagccacc tgagcaagga acagcagtga ggccgcgttg cccccatcag  20040
gcttgtggga cccagggcca gggtgaggcg ggaaggatcc atgcggatcc ccgtcctctg  20100
ggtcctctcc tcgcctggta gggacctgag cgccctctgt agtgaggcct gggtcagctc  20160
tgcagccata tgtgacgccc cttagtcaca gctcagctgt gctcagatcc tccctgagtc  20220
tattaatatc actgtgttga atttcacaac agtttggcac ttacagcgaa tctgagagga  20280
aaaccgagga gtacgatact caggtaagtc acttgtgatt cagggcacgt gcatgccagg  20340
caaatccaac accctcaaag acgggtcttt tactgtcatt gctcagtgcg gaagtctcct  20400
tggagtacgg gtcagcccgc cttgagcagg gatcccaaga gtgaacacat aaaacccaaa  20460
tttcttactg ggaagggcgg gggctcgcag agactcattt cccagtcctt acaggcacag  20520
cctgcctgtg tcaccgtata gtagggatat tttcatcgtt tgtaagtcac attcgccagg  20580
cagctgacgc aggccatggt gtctgctgtg gttgctggga acgcacttgc cgtcaccaag  20640
gccataatgg ccgcggccgc acagtggcct ggaggaatgg ccccagcagc acagggcgtc  20700
acctttcccc attgctgttg ggggagctgg aattctcagt tccagttaat agaacatttc  20760
tgcacagatg attttagttt ggtttaatct tcaccagctt atatccaact tgcatggcgt  20820
tgtaaagctg aaatcagaat ggatacagct ggcgatgtaa ctacattact tagtaggcag  20880
ttttttccgg tttctttcca ttatgtttat tgatctgttg tgggttggtt ggttttgacc  20940
```

```
aaccagaatt gatctattat tgttaactag cgcctgtagt tacacccggg ctctggcgtg  21000
tgcggtgcct cctggggctg tggcgagtgt gcgatgccct gcctgtgccc ctcacgccgc  21060
cccctgcaga gcagccctgc caccctgagc gctgtagctc gttctgtctg tccctgtcgg  21120
ggtgagctcc atgcagtgtg tttacagagg cttggcgttt gggcctctaa ctggaagcca  21180
tctttgttcc ctgcaggcca tgaagtactt gtcatacctg ctgtaccctc tctgtgtcgg  21240
gggtgctgtc tattcactcc tgaatatcaa atataagagg taggaggccg cacacgcttc  21300
ccctgctgcg tctttcccct gagaaagcca tttggatgac tgagccagag cggggtgcga  21360
ctggagggca aactcggggc cggggcactt gggccagcgc ctgggagggg tcctgcccct  21420
gcagctgcac acggtgggct ctgggcctca gtgtccccct ggtaaggtgt agctgagagg  21480
actgactcca gccaccaggc ttcatgggag gcttgggcct gagctgagag gggtcctgga  21540
gcccctggcc tctgctgccc gtgtggggtg ctggccctga gctgagaggg ttcccggagc  21600
ccccggcctc tgctgcctgg gtggggtgtt ggccctgagc cgagaggggt cctggagcct  21660
ccagcctctg ctgcccgggt ggggtgctgg ccctgagcca agagggatcc cggagccccc  21720
agcctctgtt gcccaggtgg gctgctggcc ctgagccaag agggatcccg gagcctccag  21780
cctctgctgc ccaggtgggg tgctggccct gagctgaggg gttcctggag tgcccggcct  21840
ctgctgcccg ggcagggtgc tggccctgag ctgagagggg tcctggagcc cctggcctct  21900
gctgcccagg tggggtgctg gccctgagct gaggggttcc tggagtgccc ggcctctgct  21960
gcccggccgg gggtgctcag cgctatctcc agcttgagaa ccaggctcag cactgctgct  22020
cttggctgcc gagctgccgt gagagcatct gggtattttc agaggatttt taatgaaaga  22080
attatttttc atcaatttaa tacagatatt aagctatgcg agaaatagga cttctccttt  22140
tttttccgtt tcagctggta ctcctggtta atcaacagct tcgtcaacgg tgagtccatg  22200
tgcttccctg cttcagtact agtgtttcca gcaggcagcg atttaattgt tcttgcattg  22260
aaacccagtg tggcaagccc ccctgtgatt tgaggctaat ccctccccac cctgttctgg  22320
cacatgtgcg gtgcccaggg ctccccccag gctgtgagca gataaagccc tgcgtggctt  22380
cacaacagtg actggttctg agaaacaggt ccttgtacaa gcgacaggga gtgctcacac  22440
cagatgtggc agcccctcca cgccaggctg tgtggtgcag ccgcctggta tatgtgtcca  22500
tcgctgatga aaacagcatt gtgtggtgca tgactgttgt ctgttttctt catggaaaca  22560
aggaaaccta agcattaaaa caacaccatc cacgtctggt tccttagagc aaatggaagc  22620
accaggctct ggtgcacggc gcgccccctc ctgcagatgc agtgtgggga ccctgcaggg  22680
ccctgtgctc ggggccacat gtcctgggag gcccgcctgc cccaggtggc accttcagct  22740
gcatgggctg ctgtgtccat cccccagccc caccagacca gccctgatcg cagctttgtg  22800
gtctctttgg gaagtggtcc cgtgagcatt aagggcgagg gcctgtctgg tgcagagcag  22860
gtgggtcccg cactgccgtc ctccctggta ggagtcccac acctgacccc tggggcagga  22920
ccttgtgggt caggaggccg tgtcctcata gccccagggt gctccagtgc tctcactgac  22980
ttgaccccgt gggcagcagt tacactgatt aataaataga agagctttgc tctccaaagt  23040
tgtcgtagac tcttgataaa cttaccagcc agaaagctgc ttcacaccat gatggactct  23100
gaagttgtct ggatagcaga ccttgttttc tgcccactat gcatagacgt ggcagctcgg  23160
ccctccacac ctcgtgagtg ccgtctgtgc gtagatgtgg cagcccggcc ctccgcacct  23220
cgtgagtgct gtctgtcttt ctgcaggggt ctatgccttt ggtttcctct tcatgctgcc  23280
ccagctcttt gtgaactaca aggtaaggcg gtgtgtgctg cccgcggccc ggcccccgtc  23340
```

```
tcctgtgctg cccacagctg acctgggcct gtctctcctg tttcagttga agtcagtggc  23400
acatctgccc tggaaggcct tcacctacaa ggtgagtgtg acagccggtg aggaatccct  23460
tctcactgag cagagcgtga gcaagggcgt cttccagcca acagcattac tggggccatc  23520
tctgcccaga gtgcatctgc acctgtccct ttcattgaag aatattgagg aggctccttt  23580
aaaaaaaaaa gcgaagagct atagagtaac ttcagaccct gaaagactgg ggtggttctc  23640
tcacttgtca cagatttggt tttctttttc ttttttagtg tttatgtttc ttcttagcac  23700
atgtgtcaag acacagaccc cctgtggctc agtaaccggt gcctggggac aacggattca  23760
ggcctcccag gcaggaatgg aagccccccat gggccgtggc cattccccgc tggcagagct  23820
gtggaggccc ccttggctcc gtgtgggatt agaagtgcct cggcattgca ggcggagctg  23880
agttaatggg acatgatttg cacttttctg aagtcaatta caagctccca gaggaaaggg  23940
caatgctcag gtggctctgc ccttggctct cccccttggct gtggtctcgg gcggctctaa  24000
ccttggctct ggtctcaggt ggctctgccc ttggctctgt ctcgggcggc tccagccttg  24060
gctctggttt caggccattc tctttgggtt ccccgatgtg ggagcctggg caagacccgc  24120
agtgtgtcgg gtgccagcag ctgtggggag cccatgaggg aacagagctc cgtatctcca  24180
cttgccggct ttctgctctt tttgttgttg ctgtgaggag ttccagttag ttccaagcat  24240
ctgccaaaag ccgttggctt ggttaggtta ccaaaaacag taggattcca gccccagcaa  24300
ctggggttca ccctcctccc gtctggccct gcaggctttc aacaccttca ttgatgacgt  24360
ctttgccttc atcatcacca tgcccacgtc tcaccggctg gcctgcttcc gggacgacgt  24420
ggtgtttctg gtctacctgt accagcggtg gtgagtgcgg ctgcgtatgc tcggccgttg  24480
ctccgtctca gcggcgtggc tgctgctgaa cggaatgacg gctttcaccg caccctgcgc  24540
ctgtttatcc atttgaggga aaagataatt tgcaggtggt ggtttttcct gtcttgccta  24600
aacttgggtt ccagttgccc atgatatgtc ctggcaagaa actgttccag ctctgtctcc  24660
tcactgtgct ttagaaatgc tcgtttctat gtgaattatt gatgagccac tgaaagcaaa  24720
tgtctctcct taagcgattt atttacctat tcacagtcat tgctattgag cagaacagag  24780
accgtagcat ggctaatcca tacttggcgc tagcctcgaa gtgtccagcc agcagtgtgg  24840
acctgcaggg cacaatgtca ctggggagct cactcacctc agcattggcc gcacccctta  24900
aaccagccac cagggcctct gaagactgca ttgcgtggac ctctcagctt ggccttcagg  24960
ttgaaggctg acggctgagg aaaaggcttt gtggaatttt ctaaaggcag aggttcaggc  25020
cccaccccgg gcctcggaat tttccaaatg cagaggctca ggccccaccc tgggcctccc  25080
gcttccctcc agggctgaca tctgccctct cagtcagcaa aacctccctc cagctctgct  25140
gtgccagggt aggagccagg gatctggggc tcccctcggg agggttgcat ctggaccact  25200
gcaagcactg ccctcacctc cagtgccggc cccagggcct tgtccagggg tcgaaggagt  25260
gtgtgtcacc cccaagacct gctgccaagt gtctcagagc ctcctggctg tgtcctttct  25320
ctggccctca aggtcccttt tcccatctcc ctcccccgac caggaggcca cctcacacac  25380
cacggctgtg acacttccct gtgcccttcc ctcagggcct ggggccatcc tactagtgca  25440
ggagagggat cctcttcccc caggccgtcc tggcgggtcc tgcctaggtc cggggtgccg  25500
gcccttgggg agcgcagtgc tcccgtcccc gccctgtctc cacactcaac ctcgccaggt  25560
gttcagagcc tctgtcccag ccagcatgag gctggcatgg ttctgcctgg tttaactctt  25620
tgttcgggtg cagttggcac atccacacag tggctcatgg ccgcccttgc ccagctctcc  25680
```

```
aggcctggcc gccggctgcc cccccccacc ctgttgctgt ctcgtgcagc ccctgcacgg  25740
gagctccagc ttgtgtcagc gggaagggct atttcaccat aagcaacact cacactcaca  25800
cggggcttgg ttcctgtccc ccgttcacca ttctcagatc ccccagctgg ccgcctgccc  25860
cctgcagagc ctgaggttgt ccaagccacg gagccccgga cgctgctgcg cctggtgtgg  25920
ttgtctcaac tgtgagccct tcaagtggct cccaagtcct cgcaggtggc ccggggcgtg  25980
cctgaaactg tgctgtactc aggctctgtg ttaatggctc cagacctgca aacggtgttt  26040
ggccaggatc acagggccct tggtgggcag caggtctgtt tttaagctga aaccctgtac  26100
ttctgttcgc ggccgtgtag agctgcccct tatgccacag cttcctcatc catacgtagg  26160
ggtgatgttg gcaaggcctc cggggcgctc aggatcaaag gcggcggcag tgtcctgcca  26220
agtgttcaca gctgatgaga cgtggtccct gaacacagcg gttcctgttc tgatcactcg  26280
agtctccgtg atgccaccgt tcccagaagg cagcccgtgc agcctccggg tccccccttc  26340
agccatggca gcccgtgcag cctccgggtc gtcccttcgg ccaagcttcc ctttccttga  26400
gagcagcacg ctggcctggc catgcagaac aaaacacaac tcagaaatcc ctcctcagcc  26460
ctcggcagta aaacttctga ggattcgact ttttagttaa tttgctcact gtggcagctc  26520
actggaaaat aaatcgagga tgccaagtcc tcctcttaga aaaatagccc ctgcagtggg  26580
gtttgctgat gtgctcattt gtgtcattgc aggctttatc ctgtggataa acgcagagtg  26640
aacgagtttg gggagtccta cgaggagaag gccacgcggg cgccccacac ggactgaagg  26700
ccgcccgggc tgccgccagc caagtgcaac ttgaattgtc aatgagtatt tttggaagca  26760
tttggaggaa ttcctagaca ttgcgttttc tgtgttgcca aaatcccttc ggacatttct  26820
cagacatctc ccaagttccc atcacgtcag atttggagct ggtagcgctt acgatgcccc  26880
cacgtgtgaa catctgtctt ggtcacagag ctgggtgctg ccggtcacct tgagctgtgg  26940
tggctcccgg cacacgagtg tccggggttc ggccatgtcc tcacgcgggc aggggtggga  27000
gccctcacag gcaagggggc tgttggattt ccatttcagg tggttttcta agtgctcctt  27060
atgtgaattt caaacacgta tggaattcat tccgcatgga ctctgggatc aaaggctctt  27120
tcctcttttg tttgagagtt ggttgtttta aagcttaatg tatgtttcta ttttaaaata  27180
aatttttctg gctgtggcat ttttcttgac ctggtataat gaaagtattt cggatatttg  27240
agtttaaccc ttttccagaa agtaatacat gatatggatt tatttatgca ttaaaagagc  27300
aaatttaaag a                                                        27311
```

```
<210> SEQ ID NO 4
<211> LENGTH: 12
<212> TYPE: PRT
<213> ORGANISM: Homo sapiens

<400> SEQUENCE: 4

Arg Arg Pro Lys Leu Gln Leu Ser Val Tyr Thr Thr
1               5                   10


<210> SEQ ID NO 5
<211> LENGTH: 12
<212> TYPE: PRT
<213> ORGANISM: Homo sapiens

<400> SEQUENCE: 5

Glu Asn Asn Ile Asp Leu Val Leu Asn Val Glu Asp
1               5                   10
```

```
<210> SEQ ID NO 6
<211> LENGTH: 12
<212> TYPE: PRT
<213> ORGANISM: Homo sapiens

<400> SEQUENCE: 6

Glu Asp Phe Asp Val Glu Ser Lys Phe Glu Arg Thr
1               5                   10


<210> SEQ ID NO 7
<211> LENGTH: 12
<212> TYPE: PRT
<213> ORGANISM: Homo sapiens

<400> SEQUENCE: 7

His Ala Gly Val Leu Pro Trp His Asp Gly Lys Gln
1               5                   10


<210> SEQ ID NO 8
<211> LENGTH: 12
<212> TYPE: PRT
<213> ORGANISM: Homo sapiens

<400> SEQUENCE: 8

Asp Gly Ser Ser Leu Pro Ala Asp Val His Arg Tyr
1               5                   10


<210> SEQ ID NO 9
<211> LENGTH: 12
<212> TYPE: PRT
<213> ORGANISM: Homo sapiens

<400> SEQUENCE: 9

His Arg Tyr Met Lys Met Ile Gln Leu Gly Lys Thr
1               5                   10


<210> SEQ ID NO 10
<211> LENGTH: 12
<212> TYPE: PRT
<213> ORGANISM: Homo sapiens

<400> SEQUENCE: 10

Thr Glu Leu Pro Leu Thr Val Ser Tyr Asp Lys Val
1               5                   10


<210> SEQ ID NO 11
<211> LENGTH: 12
<212> TYPE: PRT
<213> ORGANISM: Homo sapiens

<400> SEQUENCE: 11

Gln Gln Phe Gly Phe Ser Glu Lys Asp Ala Asp Glu
1               5                   10


<210> SEQ ID NO 12
<211> LENGTH: 10
<212> TYPE: PRT
<213> ORGANISM: Homo sapiens

<400> SEQUENCE: 12

Thr Arg Pro Cys Ser Gly Asp Ala Asn Cys
1               5                   10


<210> SEQ ID NO 13
<211> LENGTH: 12
```

<212> TYPE: PRT
<213> ORGANISM: Homo sapiens

<400> SEQUENCE: 13

Arg Arg Pro Lys Leu Gln Leu Ser Val Tyr Thr Thr
1 5 10

<210> SEQ ID NO 14
<211> LENGTH: 11
<212> TYPE: PRT
<213> ORGANISM: Homo sapiens

<400> SEQUENCE: 14

Glu Asn Asn Ile Asp Leu Val Leu Asn Val Glu
1 5 10

<210> SEQ ID NO 15
<211> LENGTH: 10
<212> TYPE: PRT
<213> ORGANISM: Homo sapiens

<400> SEQUENCE: 15

Phe Asp Val Glu Ser Lys Phe Glu Arg Thr
1 5 10

<210> SEQ ID NO 16
<211> LENGTH: 12
<212> TYPE: PRT
<213> ORGANISM: Homo sapiens

<400> SEQUENCE: 16

His Ala Gly Val Leu Pro Trp His Asp Gly Lys Gln
1 5 10

<210> SEQ ID NO 17
<211> LENGTH: 10
<212> TYPE: PRT
<213> ORGANISM: Homo sapiens

<400> SEQUENCE: 17

Thr Thr Tyr Met Val Pro Lys Pro Glu Glu
1 5 10

<210> SEQ ID NO 18
<211> LENGTH: 10
<212> TYPE: PRT
<213> ORGANISM: Homo sapiens

<400> SEQUENCE: 18

Ile Asn Leu Leu Thr Gly Glu Ser Asp Thr
1 5 10

<210> SEQ ID NO 19
<211> LENGTH: 10
<212> TYPE: PRT
<213> ORGANISM: Homo sapiens

<400> SEQUENCE: 19

Glu Ser Asp Thr Gln Gln Ile Glu Ala Glu
1 5 10

<210> SEQ ID NO 20
<211> LENGTH: 11
<212> TYPE: PRT
<213> ORGANISM: Homo sapiens

```
<400> SEQUENCE: 20

Lys Lys Pro Thr Ser Ala Leu Asp Glu Pro Val
1               5                   10


<210> SEQ ID NO 21
<211> LENGTH: 10
<212> TYPE: PRT
<213> ORGANISM: Homo sapiens

<400> SEQUENCE: 21

Asp Gly Ser Ser Leu Pro Ala Asp Val His
1               5                   10


<210> SEQ ID NO 22
<211> LENGTH: 12
<212> TYPE: PRT
<213> ORGANISM: Homo sapiens

<400> SEQUENCE: 22

His Arg Tyr Met Lys Met Ile Gln Leu Gly Lys Thr
1               5                   10


<210> SEQ ID NO 23
<211> LENGTH: 10
<212> TYPE: PRT
<213> ORGANISM: Homo sapiens

<400> SEQUENCE: 23

Leu Pro Leu Thr Val Ser Tyr Asp Lys Val
1               5                   10


<210> SEQ ID NO 24
<211> LENGTH: 11
<212> TYPE: PRT
<213> ORGANISM: Homo sapiens

<400> SEQUENCE: 24

Met Gln Asp Ala Val Tyr Ser Leu Gln Gln Phe
1               5                   10


<210> SEQ ID NO 25
<211> LENGTH: 9
<212> TYPE: PRT
<213> ORGANISM: Homo sapiens

<400> SEQUENCE: 25

Gly Phe Ser Glu Lys Asp Ala Asp Glu
1               5
```

TARGETING CLPTM1L FOR TREATMENT AND PREVENTION OF CANCER

CROSS-REFERENCE TO RELATED APPLICATIONS

This application is a U.S. national stage application under 35 U.S.C. § 371 of PCT Application No. PCT/US2015/010219, filed Jan. 6, 2015, published on Jul. 23, 2015 as WO 2015/108719, which claims priority under 35 U.S.C. § 119 from U.S. Provisional Patent Application No. 61/927,330, filed Jan. 14, 2014; each of which is incorporated herein by reference as if set forth in its entirety.

STATEMENT REGARDING FEDERALLY SPONSORED RESEARCH

This invention was made with government support under Grant No. U19 CA128147 awarded by the National Institutes of Health. The government has certain rights in the invention.

FIELD OF THE INVENTION

The present invention generally relates to compounds and compositions for targeting CLPTM1L polypeptides and methods for using such compounds and compositions to treat or prevent a cancer or other condition associated with CLPTM1L protein dysfunction (e.g., pathogenic production, modification, or function). In particular, the present invention relates to therapeutic agents comprising CLPTM1L targeting moieties and to methods of administering such therapeutic agents to a subject to treat or prevent a disease or condition associated with CLPTM1L protein dysfunction such as non-small cell lung cancer. Therapeutic agents, pharmaceutical compositions, and methods are provided herein.

BACKGROUND

Cancer is a disease that begins with mutation of oncogenes and tumor suppressor genes. Mutation of these critical genes allows for a cancer cell to evolve and ultimately results in pathogenic replication (a loss of normal regulatory control leading to excessive cell proliferation) of various given types of cells found in the human body. Tumor formation, tumor survival, and cancer metastasis require anchorage-independent growth and protection from genotoxin-induced apoptosis and anoikis, a programmed cell death mechanism associated with detachment of tumor cells from an extracellular substrate. Tumor cells require protection from apoptosis and anoikis to invade surrounding tissue and to undergo metastasis.

There remains a need in the art for methods for treating or preventing cancer and, in particular, for methods which slow or curb tumor growth and prevent metastasis.

BRIEF SUMMARY OF THE INVENTION

In a first aspect, the present invention provides a compound comprising a CLPTM1L-targeting agent selected from the group consisting of an antibody, a peptide, an aptamer, or a fragment thereof. The CLPTM1L-targeting agent can be a monoclonal antibody specific for at least a portion of a CLPTM1L polypeptide. The CLPTM1L polypeptide can have the amino acid sequence set forth in SEQ ID NO: 2 or a portion thereof. The monoclonal antibody can be specific to peptide having an amino acid sequence selected from the group consisting of SEQ ID NO:4-25. The monoclonal antibody can be a monoclonal anti-CLPTM1L clone selected from the group consisting of 6-1, 6-2, 10-1, 10-2, and 10-3. The monoclonal antibody can be specific to a CLPTM1L polypeptide having one or more of the mutations set forth in Table 2. In some cases, the CLPTM1L-targeting agent is a peptide having an amino acid sequence selected from the group consisting of SEQ ID NO:4-25.

In another aspect, the present invention provides a pharmaceutical composition comprising a compound provided herein and a pharmaceutically acceptable carrier.

In yet another aspect, provided herein is an agent according to a compound or composition provided herein for use as a medicament. Further provided is use of such an agent in the manufacture of a medicament.

In a further aspect, provided herein is an article of manufacture comprising a pharmaceutical composition of the invention and instructions for administration to a human subject.

In another aspect, provided herein is a method for treating or preventing a tumor pre-in a subject. The method typically comprises administering a therapeutically effective amount of a compound comprising a CLPTM1L-targeting agent to a subject in need thereof, whereby the tumor is treated or prevented in the subject. In some cases, the CLPTM1L-targeting agent is selected from the group consisting of an antibody, a peptide, and aptamer, or a fragment thereof. The CLPTM1L-targeting agent can be a monoclonal antibody specific for at least a portion of a CLPTM1L polypeptide. The CLPTM1L polypeptide can have the amino acid sequence set forth in SEQ ID NO:2 or a portion thereof. The monoclonal antibody can be specific to a peptide having an amino acid sequence selected from the group consisting of SEQ ID NO:4-25. The monoclonal antibody can be specific to a CLPTM1L polypeptide having one or more of the mutations set forth in Table 2. The CLPTM1L-targeting agent can be a peptide having an amino acid sequence selected from the group consisting of SEQ ID NO:4-25.

In some cases, the tumor is a solid tumor selected from the group consisting of glioblastoma, sarcoma, carcinoma, and lymphoma. In some cases, the tumor is associated with a cancer or pre-neoplastic lesion selected from the group consisting of lung cancer, pancreatic cancer, prostate cancer, skin cancer, bladder cancer, kidney cancer, ovarian cancer, colon cancer, colorectal cancer, breast cancer, cervical cancer, brain cancer, esophageal cancer, and stomach cancer, or a pre-neoplastic lesion thereof. The tumor can be associated with lung cancer or a pre-neoplastic lesion thereof. The tumor can exhibit resistance to a chemotherapeutic agent. The chemotherapeutic agent can be selected from the group consisting of cisplatin and gemcitabine. In some cases, the compound is administered with a pharmaceutically acceptable carrier.

In yet another aspect, provided herein is a method of treating or preventing a disease or condition associated with over-expression or inappropriate expression of a nucleic acid sequence encoding CLPTM1L in a subject. The method typically comprises administering a compound comprising a CLPTM1L-targeting agent to a cell, tissue, or organ of a subject at risk of, diagnosed as having, or exhibiting a symptom of the disease or condition. The disease or condition can be a cancer, tumor, (e.g., solid tumor) or a pre-neoplastic lesion. The tumor, cancer, or pre-neoplastic lesion can be selected from the group consisting of lung cancer, pancreatic cancer, glioblastoma, prostate cancer, skin cancer, bladder cancer, kidney cancer, ovarian cancer, colon cancer, colorectal cancer, breast cancer, cervical cancer, brain cancer, esophageal cancer, stomach cancer, lymphoma, chronic leukemia, and acute leukemia. The tumor can exhibit resistance to a chemotherapeutic agent. The chemotherapeutic agent can be selected from the group consisting of cisplatin and gemcitabine. The CLPTM1L-targeting agent can be selected from the group consisting of an antibody, a peptide, and aptamer, or a fragment thereof. The CLPTM1L-targeting agent can be a monoclonal antibody specific for at least a portion of a CLPTM1L polypeptide. The CLPTM1L polypeptide can have the amino acid sequence set forth in SEQ ID NO: 2 or a portion thereof. In some cases, the monoclonal antibody is specific to a peptide having an amino acid sequence selected from the group consisting of SEQ ID NO:4-25. The monoclonal antibody can be specific to a CLPTM1L polypeptide having one or more of the mutations set forth in Table 2. The CLPTM1L-targeting agent can be a peptide having an amino acid sequence selected from the group consisting of SEQ ID NO:4-25. The compound can be administered with a pharmaceutically acceptable carrier.

In another aspect, provided herein is a method of treating or preventing a disease or condition associated with CLPTM1 L protein dysfunction, the method comprising administering a compound comprising a CLPTM1 L-targeting agent to a cell, tissue, or organ of a subject at risk of, diagnosed as having, or exhibiting a symptom of the disease or condition. The CLPTM1 L protein dysfunction can comprise one or more of pathogenic protein production, pathogenic protein modification, or pathogenic protein function. The disease or condition can be a tumor, a cancer, or a preneoplastic lesion. The tumor can be a solid tumor selected from the group consisting of glioblastoma, sarcoma, carcinoma, and lymphoma. The tumor can exhibit resistance to a chemotherapeutic agent. The chemotherapeutic agent can be selected from the group consisting of cisplatin and gemcitabine. The CLPTM1 L-targeting agent can be selected from the group consisting of an antibody, a peptide, and aptamer, or a fragment thereof. The CLPTM1 L-targeting agent can be a monoclonal antibody specific for at least a portion of a CLPTM1 L polypeptide. The monoclonal antibody can be specific to a CLPTM1 L polypeptide having one or more of the mutations set forth in Table 2. The monoclonal antibody can be specific to a peptide having an amino acid sequence selected from the group consisting of SEQ ID NO:4-25. The compound can be administered with a pharmaceutically acceptable carrier.

These and other features, aspects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects and advantages other than those set forth above will become apparent when consideration is given to the following detailed description thereof. The detailed description makes reference to the following drawings, wherein:

FIG. 10 summarizes characterization of in vitro antitumor effects of monoclonal anti-CLPTM1L antibodies.

DETAILED DESCRIPTION OF THE INVENTION

Figure 1:
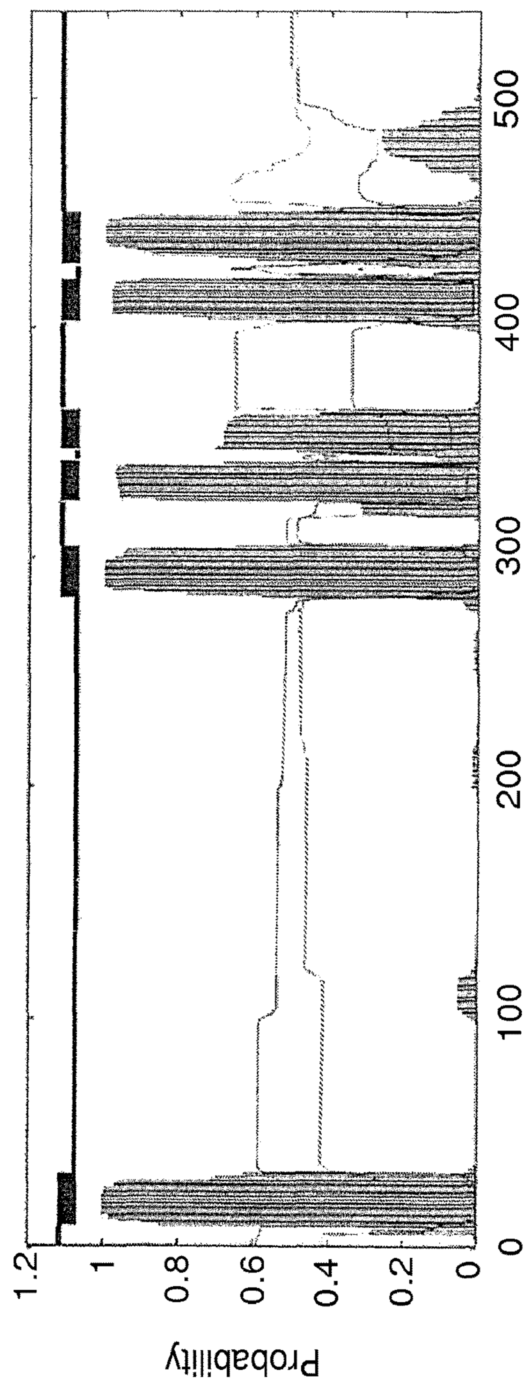
FIGS. 1A-1B present structural data demonstrating the presence of two separate globular domains separated by a small disordered region (amino acid residues 142-162) within the larger extracellular region.
Figure 1:
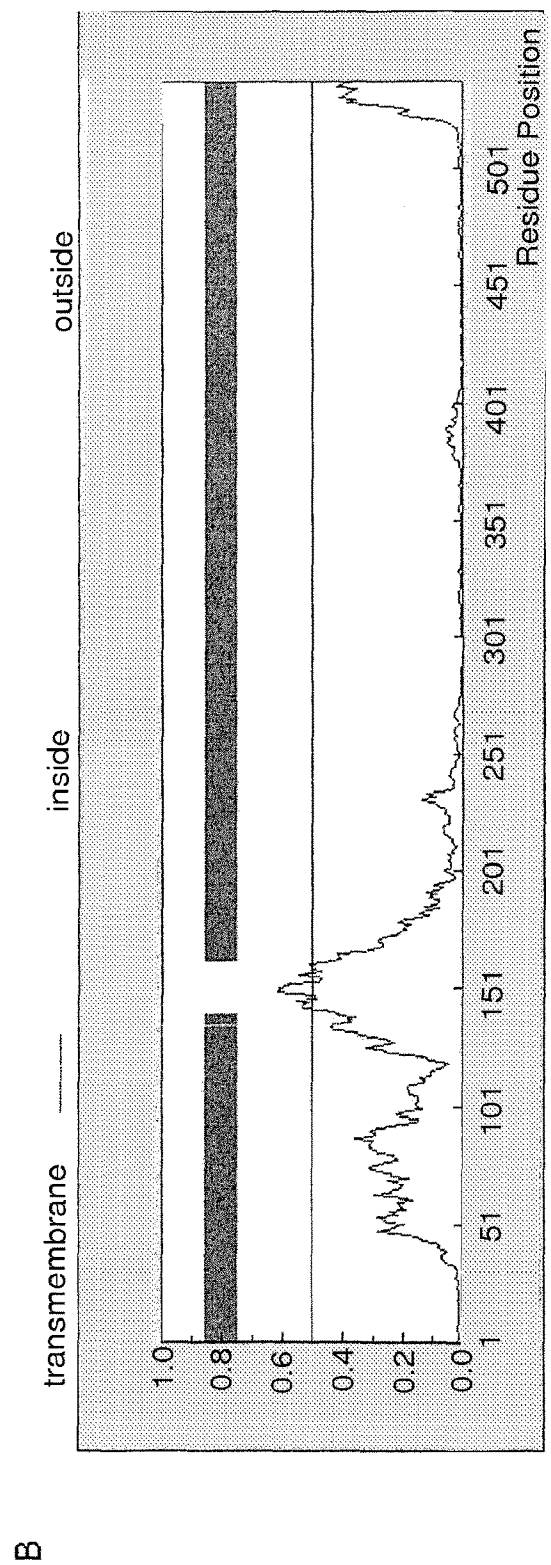

All publications, patents, and patent applications mentioned in this specification are herein incorporated by reference in their entirety as if each individual publication, patent, and patent application was specifically and individually indicated to be incorporated by reference.

The present invention is based at least in part on the Inventors' discovery that CLPTM1L is commonly overexpressed in non-small cell lung cancer (NSCLC) and that it protects lung tumor cells from genotoxic apoptosis. In particular, depletion of CLPTM1L robustly and significantly inhibited tumorigenesis in vivo in multiple models. Cisplatin Resistance Related Protein-9 (CRR9), otherwise known as Cleft-Lip and Palate Transmembrane Protein-Like Protein 1 (CLPTM1L), is located at chromosome 5p15.33 as defined by multiple Genome Wide Association (GWA) studies. The CLPTM1L gene lies within a locus on chromosome 5 that is frequently gained in copy number early in lung cancer and that is associated by genotype with lung cancer susceptibility. For example, genetic variants near and within the CLPMT1L gene are associated with lung cancer, cervical cancer, ovarian cancer, pancreatic cancer, bladder cancer, glioma, prostate cancer, basal cell carcinoma, and melanoma. Although the mechanism of action remains to be fully elucidated, it is believed that CLPTM1L is involved in Bcl-xL survival protein accumulation. Indeed, the Inventors previously demonstrated that CLPTM1L protects chemotherapeutically treated tumor cells from genotoxin-induced apoptosis and that CLPTM1L is required for anchorage independent growth and for Ras-driven lung tumorigenesis.

The Inventors further discovered that CLPTM1L localizes to the plasma membrane, and that polyclonal antibodies targeting the N-terminal region of the CLPTM1L protein, which is predicted to be extracellular, elicit comparable phenotypes to those elicited by RNA interference-mediated depletion of CLPTM1L; specifically, Bcl-xL and Akt inhibition, chemosensitization, and anchorage dependence. Accordingly, the present invention relates to immunoglobulins, compositions, and methods of using such compositions for targeting human CLPTM1L for the prevention or treatment of solid tumors and cancers and for chemosensitization of tumor cells. As used herein, the term "solid tumor" refers to an abnormal mass of tissue that usually does not contain cysts or liquid areas. Non-cancerous tumors are described as "benign," while cancerous tumors are described as "malignant." Different types of solid tumors are named for the particular cells that form them, for example, sarcomas formed from connective tissue cells (such as bone cartilage, fat), carcinomas formed from epithelial tissue cells (such as breast, colon, pancreas), and lymphomas formed from lymphatic tissue cells (such as lymph nodes, spleen, thymus). Treatment of all types of solid tumors is within the scope of this invention.

The human CLPTM1L gene (SEQ ID NO:1; Genbank ID AAH25305.1) encodes a 538 amino acid polypeptide (SEQ ID NO:2; UniProt ID: Q96KA5.1). Gene products of human CLPTM1L include a primary mRNA (Genbank ID BC016399.1; SEQ ID NO:3) and two additional predicted transcript splice variants (Ensembl transcript IDs: ENST00000320927 and ENST00000507807). These predicted splice variants encode proteins of 502 and 369 amino acids, respectively. Splice variant prediction methods are available at useast.ensembl.org/info/docs/genebuild/genome_annotation.html on the World Wide Web.

Compositions of the Invention

In one aspect, the present invention provides compositions comprising CLPTM1L-targeting agent having specificity for at least a portion of a CLPTM1L polypeptide. As described herein, compositions of the present invention are useful as therapeutic agents and pharmaceutical compositions for a variety of clinical applications. In particular, provided herein are therapeutic compositions comprising one or more CLPTM1L-targeting agent including antibodies, antibody fragments, immunoconjugates, bispecific antibodies, trispecific antibodies, and chimeric antigen receptors having specificity for (i.e., targeted to) one or more CLPTM1L epitopes. Also provided are compositions comprising one or more CLPTM1L-targeting peptides. As used herein, a CLPTM1L-targeting agent is a molecule or complex that specifically binds to a CLPTM1L polypeptide or to one or more epitopes of a CLPTM1L polypeptide or fragment thereof and/or competes for binding at one or more epitopes of a CLPTM1L polypeptide or fragment thereof.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with, any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

As used herein, the terms "antibody" and "antibodies" are synonymous with "immunoglobulin" and "immunoglobulins," and the terms are used interchangeably herein. The terms "antibody" and "antibodies" include whole immunoglobulins including, without limitation, polyclonal antibodies or monoclonal antibodies (mAbs). The term antibody encompasses various broad classes of polypeptides that can be distinguished biochemically. Those skilled in the art will appreciate that heavy chains are classified as gamma, mu, alpha, delta, or epsilon (γ, μ, α, δ, ε v) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization.

Antibodies appropriate for the present invention also include antibody fragments or modified products thereof, provided that they can be suitably used in the present invention. Appropriate antibody fragments comprise at least one variable domain of an immunoglobulin, such as single variable domains Fv (Skerra & Pluckthun, *Science* 240: 1038-41 (1988)), scFv (Bird et al., *Science* 242:423-26 (1988); Huston et al., *Proc. Natl. Acad. Sci. USA* 85:5879-83 (1988)), Fab, $(Fab')_2$ or other proteolytic fragments. The terms "antibody" and "antibodies" further include chimeric antibodies; human and humanized antibodies; recombinant and engineered antibodies, conjugated antibodies, and fragments thereof. Humanized antibodies are antibodies wherein the complementarity determining regions (CDRs) of an antibody from a mammal other than human (e.g., a mouse antibody) are transferred into the CDRs of human antibodies. Chimeric and humanized antibodies can be made according to standard protocols such as those disclosed in U.S. Pat. No. 5,565,332. Other antibody formats are described in, for example, "Antibody Engineering," McCafferty et al. (Eds.) (IRL Press 1996). Also encompassed in the invention are CLPTM1L-targeting immunoglobulins that have been conjugated or bound in some manner to various molecules including, without limitation, polyethylene glycol (PEG), radioactive substances, and drugs. Such conjugated antibodies can be obtained by chemically modifying a CLPTM1L-targeting immunoglobulin. Methods for obtaining conjugated antibodies are known and available in the art.

The antibodies of the present invention may be polyclonal or monoclonal antibodies. Preferably, the CLPTM1L-targeting immunoglobulins are monoclonal. Methods of producing polyclonal and monoclonal antibodies are known in the art and described generally, e.g., in U.S. Pat. No. 6,824,780. Typically, the antibodies of the present invention are produced recombinantly, using vectors and methods available in the art, as described further below. Human antibodies may also be generated by in vitro activated B cells (see U.S. Pat. Nos. 5,567,610 and 5,229,275). Human antibodies may also be produced in transgenic animals (e.g., mice) that are capable of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice results in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggemann et al., *Year in Immuno.,* 7:33 (1993); U.S. Pat. Nos. 5,545,806, 5,569,825, 5,591,669; 5,545,807; and WO 97/17852. Such animals may be genetically engineered to produce human antibodies comprising a polypeptide of the present invention.

The source of the antibodies described herein is not particularly restricted in the present invention; however, the antibodies are preferably derived from mammals, and more preferably derived from humans. Monoclonal antibodies appropriate for the present invention can be prepared by standard hybridoma methods. For example, standard hybridoma methods employ differential binding assays to ensure that the resulting monoclonal antibodies are specific for a CLPTM1L polypeptide and do not show cross-reactivity between related proteins. Alternatively, monoclonal antibodies appropriate for the present invention can be prepared using antibody engineering methods such as phage display. Methods for obtaining highly specific antibodies from antibody phage display libraries are known in the art, and several phage antibody libraries are commercially available from, for example, MorphoSys (Martinsried, Germany), Cambridge Antibody Technology (Cambridge UK) and Dyax (Cambridge Mass.). Suitable phage display methods are described, for example, in U.S. Pat. Nos. 6,300,064 and 5,969,108, and in "Antibody Engineering," McCafferty et al. (Eds.) (IRL Press 1996)). Once the antibody heavy and light chain genes are recovered from the phage antibodies, antibodies in any suitable format may be prepared for use according to the present invention, e.g., whole antibodies, Fab fragments, scFv, etc.

Antibodies disclosed herein may be from any animal origin including birds and mammals. Preferably, the antibodies are human, murine, donkey, rabbit, goat, guinea pig, camel, llama, horse, or chicken antibodies.

Polyclonal antibodies appropriate for the present invention can be prepared by may also be prepared using traditional animal-based methods. For example, an appropriate animal can be immunized using a polypeptide immunogen (e.g., peptide of CLPTM1L). Polypeptide antibody titers in the immunized animal can be monitored over time by standard techniques, such as with an enzyme linked immunosorbent assay (ELISA) using immobilized polypeptide. Antibodies specific to the antigen can be isolated from the mammal (e.g., from the blood) and further purified by techniques known to those practicing in the art including, for example, protein A chromatography to obtain the IgG fraction. In some cases, at an appropriate time after immunization (e.g., when the antibody titers are highest) antibody-producing cells can be obtained from the animal and used to prepare monoclonal antibodies.

As used herein, the terms "epitope" or "antigenic determinant" refer to a site on an antigen (e.g., on CLPTM1L) to which an immunoglobulin or antibody specifically binds. Generally, an epitope includes at least 3, 4, 5, 6, 7, 8, 9, 10, 11, 12, 13, 14, or 15 consecutive or non-consecutive amino acids in a unique spatial conformation. See, e.g., Epitope Mapping Protocols in Methods in Molecular Biology, Vol. 66, G. E. Morris, Ed. (1996). As used herein, the terms "specific binding," "selective binding," "selectively binds," and "specifically binds," refer to an antibody binding to an epitope via its antigen-binding domain, and that the binding entails some complementarity between the antigen-binding domain and the epitope. Generally, an antibody specifically or selectively binds with an affinity (generally represented by the dissociation constant $K_D$) of approximately less than $10^{-7}$ M, such as approximately less than $10^{-8}$ M, $10^{-9}$ M, or $10^{-10}$ M, or lower. As used herein, the term "affinity" denotes the strength of the sum total of non-covalent interactions between a single binding site of a molecule (e.g., a peptide, polypeptide, or antibody) and its binding partner (e.g., a target or an antigen). Unless indicated otherwise, as used herein, "binding affinity" refers to intrinsic binding affinity which reflects a 1:1 interaction between members of a binding pair (e.g., between a peptide and its target, or between an antibody and its antigen). The terms "$K_D$" and "$K_d$" are synonymous and refer to the dissociation equilibrium constant of a particular molecule X-binding partner Y interaction. Affinities of antibodies can be readily determined using methods known in the art such as surface plasmon resonance. Other conventional techniques for determining antibody affinities are known in the art, such as those described by Scatchard et al. (*Ann. N.Y. Acad. Sci. USA* 51:660 (1949)). Binding properties of an antibody to antigens, cells or tissues thereof may generally be determined and assessed using immunodetection methods including, for example, immunofluorescence-based assays, such as immuno-histochemistry (IHC), and/or fluorescence-activated cell sorting (FACS).

In exemplary embodiments, antibodies of the present invention bind to CLPTM1L with a dissociation equilibrium constant ($K_D$) of less than approximately $10^{-7}$ M, such as approximately less than $10^{-8}$ M, $10^{-8}$ M, or $10^{-10}$ M, or lower.

Table 1 presents amino acid sequences of epitopes useful for producing CLPTM1L-targeted monoclonal antibodies. The "start" and "end" positions are numbered relative to numbered relative to the amino acid sequence of human CLPTM1L set forth as SEQ ID NO:2 (UniProt ID: Q96AK5-1).

TABLE 1

Peptides and Epitopes For Monoclonal Antibody Production

| Start position | End position | Epitope sequences | SEQ ID NO: |
|---|---|---|---|
| 49 | 60 | RRPKLQLSVYTT | 4 |
| 68 | 79 | ENNIDLVLNVED | 5 |
| 78 | 89 | EDFDVESKFERT | 6 |
| 112 | 123 | HAGVLPWHDGKQ | 7 |
| 186 | 197 | DGSSLPADVHRY | 8 |
| 195 | 206 | HRYMKMIQLGKT | 9 |
| 233 | 244 | TELPLTVSYDKV | 10 |
| 263 | 274 | QQFGFSEKDADE | 11 |
| 33 | 42 | TRPCSGDANC | 12 |
| 49 | 60 | RRPKLQLSVYTT | 13 |
| 68 | 78 | ENNIDLVLNVE | 14 |
| 80 | 89 | FDVESKFERT | 15 |
| 112 | 123 | HAGVLPWHDGKQ | 16 |
| 131 | 140 | TTYMVPKPEE | 17 |
| 141 | 150 | INLLTGESDT | 18 |
| 147 | 156 | ESDTQQIEAE | 19 |
| 157 | 167 | KKPTSALDEPV | 20 |
| 186 | 195 | DGSSLPADVH | 21 |
| 195 | 206 | HRYMKMIQLGKT | 22 |
| 235 | 244 | LPLTVSYDKV | 23 |
| 255 | 265 | MQDAVYSLQQF | 24 |
| 266 | 274 | GFSEKDADE | 25 |

As described in greater detail in the Examples section, epitopes presented in the shaded boxes of Table 1 were initially selected for monoclonal antibody production using the following criteria: (a) epitopes that reside within the predicted surface-exposed globular domains of CLPTM1L (e.g., residues at positions 32-284); (b) epitopes that avoid predicted glycosylation sites (e.g., residues at positions 91, 101, and 229); (c) epitopes that avoid the predicted disordered region (e.g., positions 141-162); and (d) epitopes having amino acid sequences that score highly on the basis of hydrophilicity, folding potential, and antigen presentation.

Monoclonal antibodies can be obtained by hybridoma technology, which is the process of producing hybrid cell lines by fusing an antibody-producing B cell with a myeloma cell that can grow in tissue culture. The resulting hybridoma line produces a monoclonal antibody of a single specificity. Hybridoma lines for monoclonal antibodies 6-1, 10-2, and 10-3 were deposited on Dec. 12, 2018, with the American Type Culture Collection at 10801 University Boulevard, Manassas, Va. 20110-2209, U.S.A., under Accession Nos. PTA-125531 (Hybridoma *Mus musculus* cell lines; ESS6-1), PTA-125531 (Hybridoma *Mus musculus* cell lines; ESS6-1), and PTA-125530 (Hybridoma *Mus musculus* cell lines; ESS10-3), respectively, under the terms and conditions of the Budapest Treaty.

In exemplary embodiments, a composition provided herein comprises a CLPTM1L-specific immunoglobulin (e.g., polyclonal or monoclonal antibody) that is chemically or structurally modified, conjugated chimerized, humanized, or otherwise engineered antibody. For example, compositions of the invention include a CLPTM1L-specific antibody modified as an immunoconjugate. As used herein, the term "immunoconjugate" refers to a therapeutic agent that comprises (1) an antibody that binds to an antigen (e.g., a cancer cell antigen) with high specificity, (2) an effector molecule, and (3) a linker. The effector molecule can be selected from the group consisting of therapeutic agents, prodrugs, peptides, proteins, enzymes, viruses, lipids, biological response modifiers, pharmaceutical agents, and polyethylene glycol (PEG). Preferably, the effector molecule has anti-cancer cell activity. See, e.g., Smaglo et al., *Nat. Rev. Clin. Oncol.* 11(11):637-48 (2014).

Appropriate linkers include, without limitation, can be a thioester bond, a disulfide bond, a hydrazone bond, or a peptide. Preferably, the linker operates to ensure that the effector does not separate from the antibody during transit and will reliably release the effector to a targeted cancer cell or tumor stroma. See, for review, Smaglo et al., *Nature Reviews Clin. Oncol.* 11:637-48 (2014). Without being bound by any particular mechanism or mode of action, it is believed that immunoconguates are particularly effective anticancer agents because they possess the potent anticancer effects of a therapeutic agent (e.g., chemotherapeutic) as well as the highly specific cancer targeting properties of a cancer cell antigen-specific monoclonal antibody. In exemplary embodiments, immunoconjugates of the present invention comprise a therapeutic agent selected from a pharmacologic agent, radioisotope, and toxin; a CLPTM1L-specific monoclonal or polyclonal antibody moiety; and a linker.

In some cases, a CLPTM1L-specific immunoglobulin of the present invention is a bispecific monoclonal antibody (BsMAb, BsAb). As used herein, the terms "bispecific monoclonal antibody," "BsMAb," and "BsAb" are used interchangeably and refer to an engineered immunoglobulin comprising two different monoclonal antibodies or fragments thereof. Accordingly, bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. For example, a BsMAb can be engineered to simultaneously bind an immune cell (e.g., a T cell, a B cell, a monocyte, a macrophage, a neutrophil, a dendritic cell, a phagocyte, a natural killer cell, an eosinophil, a basophil, a mast cell) and a cancer cell antigen (e.g., CLPTM1L) to target and kill the cancer cell.

A bispecific antibody of the invention can further comprise a human or a humanized Fc fragment such as a human IgG Fc fragment. CLPTM1L-specific immunoglobulins can be humanized or subjected to Fc modification according to any appropriate methodology. As used herein, the term "humanized antibody" generally refers to a human antibody that has one or more amino acid residues introduced into it from a source that is non-human. These non-human amino acid residues are often referred to as "import" residues, which are typically taken from an "import" variable domain. Humanization is traditionally performed following the method of Winter and co-workers (Jones et al., *Nature,* 321:522-525 (1986); Reichmann et al., *Nature,* 332:323-327 (1988); Verhoeyen et al., *Science,* 239:1534-1536 (1988)), by substituting import hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. Bispecific antibodies can be prepared as full length antibodies or antibody fragments (e.g., $F(ab')_2$ bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody. Traditional production of full length bispecific antibodies is based on the co-expression of two immunoglobulin heavy chain-light chain pairs, where the two chains have different specificities (Millstein et al., *Nature,* 305:537-539 (1983)).

As used herein, the term "Fc" fragment refers to the carboxy-terminal portions of two heavy (H) chains held together by disulfide bonds. The effector functions of antibodies are determined by sequences in the Fc region, which region is also the part recognized by Fc receptors (FcR) found on certain types of cells. Fc regions can be modified to improve or reduce binding to effector regions. See, e.g., Vincent and Zurini, *Biotechnol. J.* 7(12):1444-50 (2012). Other examples of Fc engineering include modifying the half-life of immunoglobulin G (IgG). For example, antibody fragments having an increased in vivo half-life comprising a salvage receptor binding epitope residues are described in U.S. Pat. No. 5,869,046. Furthermore, engineered pH-dependent antigen binding can be applied to enhance the recycling of IgG via FcRn, enabling binding to additional target molecules. For review, see Kaneko and Niwa, *Biodrugs* 25(1):1-11 (2011). Other techniques for the production of antibody fragments will be apparent to the skilled practitioner.

Without being bound by any particular mechanism or mode of action, it is believed that bispecific monoclonal antibodies exhibit increased antibody-dependent cell-mediated cytotoxicity (Chames et al., *mAbs* 1:6, 539-547 (2009)). Accordingly, an effective dose of a CLPTM1L-targeted bispecific monoclonal antibody of the present invention can be lower than the effective dose of a conventional monoclonal CLPTM1L-specific antibody. In some cases, an effective dose of such a bispecific antibody is one or more orders of magnitude lower than that of a conventional monoclonal antibody. For example, an effective dose of a CLPTM1L-targeted bispecific monoclonal antibody can be around 0.01 $mg \cdot m^{-2} \cdot d^{-1}$ (milligrams per square meter body surface area per day).

Bispecific antibodies may also be used to localize cytotoxic agents to cancer cells. These antibodies possess a cancer/tumor-binding arm and an arm that binds a cytotoxic agent (e.g., saporin, anti-interferon-α, vinca alkaloid, ricin A chain, methotrexate, or radioactive isotope hapten).

Bispecific antibodies also include antibodies having more than two valencies. For example, bispecific antibodies include trifunctional hybrid antibodies which, as used herein, are antibodies capable of inducing antibody-mediated cytotoxicity (via interactions with tumor-associated antigens on target cancer cells) and T-cell mediated cytotoxicity (via recognition of cytotoxic T lymphocytes) as well as anti-tumor immunologic memory (via interactions of a Fc region with markers on accessory cells such as macrophages). See Tutt et al., *J. Immunol.* 147: 60 (1991). For example, bi- and tri-specific antibodies against CD16, CD19, and CD22 have been shown to activate natural killer cell activation against B-cell leukemia (Gleason et al., *Mol. Cancer. Ther.* 11(12):2674-84 (2012)).

Tri-specific antibodies (also known as trifunctional hybrid antibodies) comprise light and heavy chains originating from parental mouse IgG2a and rat IgG2b monoclonal antibodies, each having different antigen binding properties that provide additive tumor killing capabilities through the efficient recruitment of macrophages and NK cells and efficient co-stimulation of T cells through direct contact with accessory cells such as macrophages. By forming a tri-cell complex comprising a tumor cell, T cell, and accessory cell, trifunctional hybrid antibodies induce coordinated signaling events required for efficient tumor cell destruction. Among those coordinated signaling events are immune effector mechanisms regulating destructive processes such as phagocytosis and perforin-mediated necrosis. For example, tri-specific antibodies targeting chorionic embryonic antigen (CEA) and the T-cell co-receptors CD3 and CD28 have been shown to recruit T lymphocytes to kill CEA positive tumors (Wang et al., *J Biochem.* 135(4):555-65 (2004)).

In some embodiments, antibodies of the invention are modified with respect to effector function, e.g., so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and ADCC. See Caron et al., *J. Exp Med.* 176:1191-1195 (1992). Homodimeric antibodies with enhanced anti-infection activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et at, *Anti-Cancer Drug Design* 3:219-230 (1989).

In other cases, a CLPTM1L-specific antibody of the present invention is embodied in a chimeric antigen receptor T cell. As used herein, the term "chimeric antigen receptor T cell" refers to a genetically engineered antibody-T cell chimera that comprises a chimeric antigen receptor (CAR). As described herein, chimeric antigen receptor T cells of the present invention are therapeutic agents having the antigen specificity of a CLPTM1L-specific antibody and the polyfunctionality and potency of cellular immunity. Techniques for chimeric antigen receptor T cell therapies are known and available in the art. See, e.g., Kenderian et al., *Cancer Res.* 74(22):6383-9 (2014).

In exemplary embodiments, CLPTM1L-specific immunoglobulins provided herein are modified to possess altered binding properties or increased affinity to the target antigen by, for example, affinity improvement or affinity maturation. As used herein, the term "affinity-matured antibody" refers to an antibody or a fragment thereof with one or more amino acid substitutions in a variable region, which results in improved affinity of the antibody for an antigen, as compared to a parent (starting) antibody which does not possess those substitutions. Antibody affinity enhancement techniques are known and available in the art. For example, random mutagenesis (Groves et al., *J. Immunol. Methods,* 313:129-39, 2006) and site-directed mutagenesis methods (Barbas et al., *Proc. Natl. Acad. Sci. USA,* 91:3809-13, 1994) are known. In some cases, these mutagenesis methods are combined with, for example, in vitro display-based technologies such as phage or ribosome display to generate libraries of variants for subsequent screens (Almagro and Strohl, Antibody Engineering: Humanization, Affinity Maturation and Selection Methods. 307-327. In: Therapeutic Monoclonal Antibodies: From Bench to Clinic. Ed. Zhiqiang An. John Wiley & Sons, Inc. 2009). Preferably, a modified antibody obtained by affinity improvement or affinity maturation as described herein will exhibit 2-fold, 5-fold, 10-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, 10000-fold or more improved activity for the target antigen compared to a starting antibody. For example, Kaneko and Zurini review optimizing therapeutic antibodies.

In some cases, an immunoglobulin of the invention specifically targets a CLPTM1L polypeptide having one or more mutations. Frameshift and missense mutations of CLPTM1L polypeptides that may be targeted may include, but are not limited to, those set forth in Table 2. The amino acid residue positions are numbered relative to the amino acid sequence of human CLPTM1L set forth as SEQ ID NO:2. Nucleotide positions for coding sequence mutations are numbered relative to the nucleotide sequence of human CLPTM1L set forth as SEQ ID NO:1. Somatic CLPTM1L mutations have been found in tumors of the autonomic ganglia, breast, central nervous system, endometrium, kidney, large intestine, liver, lung, ovary, prostate, skin, stomach, and upper respiratory tract. Each of the known CLPTM1L mutations is rare (<3% of tumors tested), and the functional effects of these mutations are unknown.

TABLE 2

Known Frameshift and Missense Mutations in Human Tumors.

| Position | CDS Mutation | AA Mutation | Type |
|---|---|---|---|
| 206 | c.616delA | p.T206fs*17 | Deletion - Frameshift |
| 61 | c.181A > G | p.T61A | Substitution - Missense |
| 72 | c.214G > A | p.D72N | Substitution - Missense |
| 74 | c.221T > C | p.V74A | Substitution - Missense |
| 105 | c.313T > C | p.Y105H | Substitution - Missense |
| 108 | c.323T > A | p.I108N | Substitution - Missense |
| 110 | c.329T > C | p.L110P | Substitution - Missense |
| 113 | c.338C > A | p.A113D | Substitution - Missense |
| 132 | c.394A > G | p.T132A | Substitution - Missense |
| 151 | c.452A > C | p.Q151P | Substitution - Missense |
| 159 | c.476C > T | p.P159L | Substitution - Missense |
| 175 | c.524C > T | p.A175V | Substitution - Missense |
| 196 | c.586C > T | p.R196W | Substitution - Missense |
| 196 | c.587G > A | p.R196Q | Substitution - Missense |
| 216 | c.646G > A | p.D216N | Substitution - Missense |
| 221 | c.661C > T | p.R221C | Substitution - Missense |
| 250 | c.749G > A | p.R250H | Substitution - Missense |

TABLE 2-continued

Known Frameshift and Missense Mutations in Human Tumors.

| Position | CDS Mutation | AA Mutation | Type |
|---|---|---|---|
| 266 | c.796G > A | p.G266R | Substitution - Missense |
| 313 | c.939G > T | p.K313N | Substitution - Missense |
| 319 | c.957C > G | p.I319M | Substitution - Missense |
| 320 | c.959G > A | p.G320D | Substitution - Missense |
| 322 | c.965C > T | p.S322F | Substitution - Missense |
| 353 | c.1058C > T | p.A353V | Substitution - Missense |
| 377 | c.1128_1129CC > AA | p.L377M | Substitution - Missense |
| 390 | c.1168G > A | p.E390K | Substitution - Missense |
| 396 | c.1187A > G | p.Y396C | Substitution - Missense |
| 400 | c.1198G > T | p.A400S | Substitution - Missense |
| 405 | c.1214C > T | p.S405L | Substitution - Missense |
| 430 | c.1289C > A | p.S430Y | Substitution - Missense |
| 431 | c.1291T > C | p.W431R | Substitution - Missense |
| 465 | c.1394C > T | p.P465L | Substitution - Missense |
| 490 | c.1469C > T | p.T490M | Substitution - Missense |
| 493 | c.1477C > T | p.R493W | Substitution - Missense |
| 498 | c.1493G > A | p.R498Q | Substitution - Missense |
| 500 | c.1498G > A | p.D500N | Substitution - Missense |
| 517 | c.1550A > G | p.K517R | Substitution - Missense |
| 529 | c.1587G > C | p.E529D | Substitution - Missense |
| 532 | c.1595C > T | p.T532M | Substitution - Missense |
| 533 | c.1597C > T | p.R533W | Substitution - Missense |
| 538 | c.1612G > A | p.D538N | Substitution - Missense |

*CDS = coding sequence

In another aspect, the present invention provides a nanoparticle conjugated to one or more CLPTM1L-specific immunoglobulins. Generally, antibody-conjugated nanoparticles are able bind to targets with high affinity and cross biological barriers (e.g., blood-brain barrier (BBB)) and, therefore, are advantageous for molecular and cellular targeting. Accordingly, a an antibody-conjugated nanoparticle provided herein is useful for a variety of biomedical applications such as in vivo diagnosis, clinical therapies, targeted drug delivery, gene therapy, cell labeling/tracking, and molecular imaging. In some cases, nanoparticles of the present invention are lipid-based vehicles (e.g., liposomes, solid lipid nanoparticles, micelles); polymer carriers, such as hydrogels, polymersomes, dendrimers, and nanofibers; metallic nanoparticles (e.g., gold, silver, titanium); carbon structures (e.g., nanotubes, nanohorns, nanodiamonds (NDs), grapheme); or inorganic particles (e.g., silica). See, e.g., Chow and Ho, *Sci Transl Med* 5:216rv4 (2013); Montenegro et al., *Adv. Drug Delivery Rev.* 65:677-688 (2013).

In a further aspect, the present invention provides compositions comprising an immunoglobulin that targets a CLPTM1L polypeptide and at least one pharmaceutically acceptable carrier, diluent, or excipient. As used herein, the phrase "pharmaceutically acceptable" refers to those agents, compounds, materials, compositions, and/or dosage forms which are, within the scope of sound medical judgment, suitable for use in contact with the tissues of humans and animals without excessive toxicity, irritation, allergic response, or other problems or complications, commensurate with a reasonable benefit/risk ratio.

In another aspect, compositions of the present invention include peptides comprised of part of the CLPTM1L amino acid sequence. For example, the present invention provides a peptide having the amino acid sequence of SEQ ID NO:4, 5, 6, 7, 8, 9, 10, 11, 12, 13, 14, 15, 16, 17, 18, 19, 20, 21, 22, 23, 24, or 25 (see Table 1). Additional CLPTM1L peptides of the present invention include peptides selected according to the above-defined epitope properties. Peptides may represent 8-22 amino acid length portions of SEQ ID NO. 2. In some cases, a CLPTM1L peptide may be embodied as a therapeutic agent. For example, a CLPTM1L peptide can be embodied in a peptide vaccine, a ligand blocking peptide, or a competitive inhibitory peptide. Such agents are expected to be useful therapeutic agents for treating or preventing lung cancer. Peptide vaccines are particularly amenable to prophylactic approaches. It is further expected that a CLPTM1L epitope, a CLPTM1L immunoglobulin, or any other CLPTM1L-targeting therapeutic agent will be useful in the treatment or prevention of many cancer types including, without limitation, lung, cervical, myeloblastic leukemia, pancreatic, bladder, glioma, prostate, basal cell carcinoma, and melanoma.

In some cases, a composition of the present invention is an aptamer having specificity for a CLPTM1L target molecule. As used herein, the term "aptamer" refers to a structured oligonucleotide-based or peptide-based molecule having high affinity and specificity for a specific target molecule (e.g., proteins, phospholipids, iron channels, nucleic acids, whole cells) due to unique structural features that restrict the aptamer to particular conformations. Oligonucleotide aptamers such as ribonucleic acid (RNA) and single-strand deoxyribonucleic acid (ssDNA) aptamers. Peptide aptamers are combinatorial protein molecules that comprise a short peptide region attached at both ends to a protein scaffold. Methods for designing and identifying therapeutic aptamers having high affinity and specificity for a CLPTM1L target molecule are known in the art. See, e.g., Rohloff et al., *Molecular Therapy Nucleic Acids* 3:e201 (2014); Zhu et al., *Theranostics* 4(9):931-944 (2014); Ellington and Szostak, *Nature* 346:818-822 (1990).

Compositions provided herein can comprise at least one pharmaceutically acceptable diluent, excipient, or carrier. As used herein, "pharmaceutically acceptable carrier" refers to any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

Regardless of the route of administration selected, therapeutic agents of the present invention, which may be used in a suitable hydrated form, and/or the pharmaceutical compositions of the present invention, can be formulated into pharmaceutically acceptable dosage forms by conventional methods known to those of skill in the art.

In certain embodiments, a pharmaceutical composition provided herein comprises one or more CLPTM1L-targeting agents, a chemotherapeutic agent, and a pharmaceutically acceptable carrier. Chemotherapeutic agents include, without limitation, platinum-based agents, such as cisplatin, gemcitabine, and carboplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon .alpha., and tretinoin (ATRA); antibiotic natural antineoplastics, such as bleomycin, dactinomycin, daunorubicin, doxorubicin, and mitomycin; and *vinca* alkaloid natural antineoplastics, such as vinblastine and vincristine.

In other embodiments, compositions of the invention provided herein can additionally comprise one or more other biologically active substances including, without limitation, therapeutic drugs or pro-drugs such as chemotherapeutic agents other than those identified above, scavenger compounds, antibiotics, antiviral agents, antifungal agents, anti-inflammatory agents, vasoconstrictors and anticoagulants, antigens useful for cancer vaccine applications or corresponding pro-drugs.

Methods of Using Compositions of the Invention

In one aspect, the present invention is directed to methods of treating or preventing a disease or condition in a subject by inhibiting CLPTM1L. For example, the present invention provides methods comprising administering to a subject in need thereof an immunoglobulin or a composition comprising an immunoglobulin that targets and specifically binds to CLPTM1L. As used herein, the term "subject" refers to an individual having, suspected of having, or susceptible to having a disease or condition associated with CLPTM1L protein dysfunction (e.g., pathogenic production, modification, or function) or for which there is a genetic association with CLPTM1L (e.g., a disease or condition associated with a gain in CLPTM1L locus copy number or a genotype for susceptibility to the disease or disorder). By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, the terms "treating," "treat," and "treatment" refer to the management and care of a patient for the purpose of combating the disease, condition, or disorder. The terms embrace both preventative, i.e., prophylactic, and palliative treatments. In some cases, the term "treated" refers to any beneficial effect on progression of a disease or condition. Beneficial effects can include reversing, alleviating, inhibiting the progress of, preventing, or reducing the likelihood of the disease or condition to which the term applies or one or more symptoms or manifestations of such a disease or condition. Where the disease or condition is a tumor, cancer, or cancer-associated condition, treating can refer to the management and care of a patient for the purpose of combating cancer, and can include reversing, alleviating, inhibiting the progress of, preventing, reducing the size of, or reducing the likelihood of, or lessening the severity of any aspect of the cancer or cancer-associated condition (e.g., metastasis, tumor growth). A therapeutic beneficial effect on the health and well-being of a patient includes, but it not limited to: (1) curing the cancer; (2) slowing the progress of the cancer; (3) causing the tumor to regress; or (4) alleviating one or more symptoms of the cancer. As used herein, the terms "preventing" and "prevent" refer not only to a complete prevention of a certain disease or condition, but also to partially or substantially attenuating, reducing the risk of, or delaying the development or recurrence of the disease or condition to which the term applies.

In some cases the methods provided herein are directed to treating or preventing a tumor cancer in a subject by administering a composition provided herein. In an exemplary embodiment, the method treats or prevent a solid tumor in the subject receiving administration of a composition comprising a CLPTM1L-targeting agent to a subject in need thereof. As used herein, the term "cancer" includes, without limitation, solid tumors and blood-borne tumors (e.g., leukemias). The term cancer includes, without limitation, diseases of the skin, tissues, organs, bone, cartilage, blood, and vessels. The term further encompasses both primary and metastatic cancers. In some cases, therefore, methods of treating or preventing cancer as provided by the present invention include methods of inhibiting, retarding, or preventing growth of a tumor or tumor cells. A subject in need thereof may include, for example, a subject who has been diagnosed with a tumor, including a pre-cancerous tumor, a cancer (e.g., a non-small cell lung cancer), or a subject who has been treated, including subjects that have been refractory to previous treatment.

In some cases, solid tumors appropriate for the present invention are considered to be a "refractory" or "resistant" solid tumor, meaning that the solid tumor does not respond to treatment. The tumor may be resistant at the outset of treatment or it may develop resistance during treatment. While any and all tumors that are susceptible to treatment and/or prophylactic administration of a CLPTM1L-targeting agent described herein are of course within the scope of this invention, it is anticipated that the compositions and methods provided herein will be particularly useful in the treatment of refractory tumors.

The methods provided herein are appropriate for treating or preventing any type of disease or condition associated with CLPTM1L protein dysfunction (e.g., pathogenic production, modification, or function) or any disease or condition for which there is a genetic association with CLPTM1L (e.g., a disease or condition associated with a gain in CLPTM1L locus copy number or a genotype for susceptibility to the disease or disorder). In an exemplary embodiment, a method provided herein is for the treatment or prevention of a cancer, a tumor (e.g., a solid tumor), or a pre-neoplastic lesion (e.g., pre-cancerous lesion). Examples of cancers appropriate for methods of treating or preventing as provided herein include, without limitation, lung cancer, pancreatic cancer, prostate cancer, skin cancer, bladder cancer, kidney cancer, ovarian cancer, colon cancer, colorectal cancer, breast cancer, cervical cancer, brain cancer, esophageal cancer, and stomach cancer. Solid tumors can be associated with cancers and pre-neoplastic lesions of the lung, pancreas, prostate, breast, kidney, and other sarcomas, carcinomas, and glioblastomas. Other diseases or conditions appropriate for methods of treating or preventing as provided herein include, without limitation, lymphomas, chronic leukemia, and acute leukemia.

In some cases, a method provided herein can be practiced to treat or prevent a disease or condition in a subject, where the disease or condition exhibits chemotherapeutic drug resistance. For example, a subject can be diagnosed or identified as having a disease or condition such as cancer that exhibits resistance to a chemotherapeutic agent such as cisplatin or gemcitabine. CLPTM1L has been found to be highly expressed in cisplatin resistant ovarian tumor cell lines. Moreover, CLPTM1L appears to be anti-apoptotic under genotoxic conditions. Examples of cancers for which treatment involves administering cisplatin include lung cancer, colorectal cancer, non-small cell lung cancer (NSCLC), bronchioloalviolar cell lung cancer, bone cancer, pancreatic cancer, skin cancer, cancer of the head or neck, cutaneous melanoma, intraocular melanoma, uterine cancer, ovarian cancer, rectal cancer, anal region cancer, stomach cancer, gastric cancer, colon cancer, breast cancer, uterine cancer, fallopian tube carcinoma, endometrial carcinoma, cervical carcinoma, Hodgkin's Disease, esophagus cancer, small intestine cancer, endocrine system cancer, thyroid gland cancer, parathyroid gland cancer, adrenal gland cancer, soft tissue sarcoma, prostate cancer, bladder cancer, kidney cancer, renal cell carcinoma, renal pelvis carcinoma, mesothelioma, hepatocellular cancer, biliary cancer, chronic leukemia, acute leukemia, lymphocytic lymphoma, CNS neoplasm, spinal axis cancer, brain stem glioma, glioblastoma multiforme, astrocytoma, schwannoma, ependymoma, medulloblastoma, meningioma, squamous cell carcinoma and pituitary adenoma tumors or tumor metastases.

In some cases, a method provided herein can be practiced to treat or prevent a cancer associated with a mutation, translocation, amplification, or deletion of at least a portion of at least one of the following: K-Ras, H-Ras, N-Ras, RASSFI, PI3KCA, PTEN, EGFR, FGFR1, PDGFRA, BRAF, AKL, ROS1, BCL-x, BIM, BAD, BAX, AKT, and mTOR. In an exemplary embodiment, a method provided herein can be practiced to treat or prevent a cancer for which at least one of these genes suspected of being or demonstrated to be regulated by CLPTM1L.

In some cases, a method provided herein can be practiced to treat or prevent a cancer previously or currently being subjected to radiation therapy. As used herein, the term "radiation therapy" refers to any manner of treatment of solid tumors and cancers with ionizing radiation and includes, without limitation, external beam radiotherapy, stereotatic radiotherapy, virtual simulation, 3-dimensional conformal radiotherapy, intensity-modulated radiotherapy, ionizing particle therapy, and radioisotope therapy.

In other cases, a method provided herein can be practiced to treat or prevent a cancer previously or currently being subjected to chemotherapy using a chemotherapeutic agent such as, for example, an alkylating agent, a cross-linking agent, an anti-metabolite, an antibiotic, a topoisomerase inhibitor, or a mitotic inhibitor. As used herein, the term "chemotherapeutic agent" refers to any substance that, when administered in a therapeutically effective amount to a patient suffering from a tumor or cancer, has a therapeutic beneficial effect on the health and well-being of the patient. A therapeutic beneficial effect on the health and well-being of a patient includes, but it not limited to: (1) curing the cancer; (2) slowing the progress of the cancer; (3) causing the tumor to regress; or (4) alleviating one or more symptoms of the cancer. As used herein, a chemotherapeutic agent also includes any substance that, when administered in a prophylactic amount to a patient afflicted with a solid tumor or who has been rendered substantially free of cancer as the result of one or more therapeutic treatment regimes, has a beneficial effect on the health and well-being of the patient.

The method also can be practiced to treat or prevent a cancer if use of such a therapeutic agent is anticipated. For example, methods provided herein are useful to treat or prevent a cancer for which targeting CLPTM1L sensitizes the cancer cells to DNA damage-induced apoptosis. As used herein, the terms "sensitize" and "sensitized" refers to cells made more responsive to an agent, a treatment, an environment, a stimulus, or a condition. For example, a "sensitized" cell can exhibit an increase in the magnitude of said response or an increase in any type of response. In an exemplary embodiment, cancer cells exhibit increased apoptosis when sensitized to DNA damage by targeting CLPTM1L according to a method provided herein.

In some cases, a method provided herein can be practiced to treat or prevent a cancer suspected of being or demonstrated to be refractory to one or more chemotherapeutics such as, for example, an alkylating agent, a cross-linking agent, an anti-metabolite, an antibiotic, a topoisomerase inhibitor, or a mitotic inhibitor. For example, a method provided herein can be appropriate to treat or prevent a cancer for which targeting CLPTM1L using an immunoglobulin sensitizes the cancer cells to cytotoxic treatment with a cross-linking agent and a topoisomerase inhibitor.

In exemplary embodiments, a method of treating or preventing cancer as provided herein comprises administering to a subject in need thereof two or more CLPTM1L-specific immunoglobulins. The two or more CLPTM1L-specific immunoglobulins can be administered simultaneously or sequentially. For example, the method can comprise administering two or more CLPTM1L-specific immunoglobulins, where the immunoglobulins are selected for capacity to increase sensitivity of CLPTM1L-expressing tumor cells to a chemotherapeutic agent (e.g., cisplatin, gemcitabine) and/or for an enhanced capacity for cytotoxicity toward CLPTM1L-expressing tumor cells. The combination can comprise antibodies having specificity to different polypeptides or to different epitopes on the same polypeptide. Such combination therapies have been shown to improve tumor responses and reverse resistance of tumor cells to a single agent. See, e.g., Weiner et al., *Nature Rev. Immunol.* 10:317-327 (2010).

In another aspect, provided herein is a method of treating or preventing cancer in a subject, where the method comprises administering an immunoconjugate. As described herein, immunoconjugates are effective cytotoxic and anticancer therapeutic agents.

In a further aspect, provided herein is a method of treating or preventing cancer in a subject, where the method comprises administering activated T cells to a subject in need thereof. Such activated T cell therapy methods generally comprise ex-vivo activation and expansion of T cells. See, for review, Slaney et al., *Cancer Res.* 74:7168-7174 (2014). In some cases, T cells are obtained from a subject, then purified, expanded, and activated ex vivo. Activation comprises culturing purified and expanded T cells in the presence of a cancer cell-specific or tumor specific antigen (e.g., a monoclonal antibody provided herein). The resulting activated T cells are provided back to the subject. T cells activated in this manner have enhanced immunostimulatory capabilities. In exemplary embodiments, T cells obtained from a subject in need of treatment according to a method provided herein are cultured in the presence of one or more CLPTM1L-specific monoclonal antibodies (e.g., mAbs 6-1, 10-2, and 10-3).

Methods of treating or preventing cancer as provided herein can be practiced at any appropriate time. In some cases, a composition comprising a CLPTM1L-targeting agent as provided herein is administered to a subject following diagnosis of a cancer or a pre-neoplastic lesion (e.g., pre-cancerous lesion) in, for example, a biological sample from the subject. In other cases, a composition comprising a CLPTM1L-targeting agent as provided herein is administered to a subject following identification of copy number gain or expression of CLPTM1L in a biological sample from the subject, where the level of expression is above a threshold that is empirically determined to constitute cancer risk.

Determination of such a threshold includes analysis of current and future data correlating CLPTM1L expression in normal tissue with incidence of a cancer. With respect to lung tissue, a threshold that is empirically determined to constitute cancer risk can be at least 2-fold greater average expression for one or more test lung tissue samples relative to the average expression in a healthy sample taken from surrounding tissue. In some cases, treatment may be indicated if it is determined that expression of CLPTM1L is higher in a test sample (e.g., tissue suspected of comprising cancer cells) compared to tissue surrounding the sampled tissue. In other cases, treatment may be indicated if it is determined that an increased amount of CLPTM1L is present on a tumor cell surface. Such an increased level of CLPTM1L can be detected by, for example, flow cytometry in circulating tumor cells or in solid tumors. A composition comprising a CLPTM1L-targeting agent as provided herein can be administered to a subject upon identification of one or more indicators or risk factors for the development of cancer or following identification of a genotype associated with a cancer in a biological sample from the subject. To prevent or slow tumor formation, a composition comprising a CLPTM1L-targeting agent as provided herein is administered to a subject prior to or in the absence of a cancer or pre-neoplastic lesion. In such cases, the composition is administered as a preventative agent.

Treatment or prevention according to a method provided herein can occur before, during, or after the subject is treated by surgery, radiation, and/or chemotherapy. In some cases, treatment according to a method provided herein prior to chemo- or radiotherapy may improve the outcome of the conventional therapy. In an exemplary embodiment, a composition comprising a CLPTM1L-targeting agent as provided herein is administered to a subject concurrently with one or more other treatments or preventative measures such as radiotherapy, chemotherapy, or surgery.

A composition comprising a CLPTM1L-targeting agent as provided herein is administered to a subject by any method that achieves the intended purpose or is deemed appropriate by those of skill in the art. For example, a composition of the present invention can be administered as a pharmaceutical, and may be administered systemically or locally via oral or parenteral administration. As used herein, the term "administration" includes oral and parenteral administration. Oral administration includes, for example, administration of oral agents. Such oral agents include, for example, granules, powders, tablets, capsules, solutions, emulsions, and suspensions. Parenteral administration includes, for example, administration of injections. Such injections include, for example, subcutaneous injections, intramuscular injections, and intraperitoneal injection. In some cases, intravenous injections such as drip infusions, intramuscular injections, intraperitoneal injections, subcutaneous injections, suppositories, enemas, oral enteric tablets, or the like can be selected.

Appropriate modes of administration can be determined based on the physical location of a tumor or tumors in the subject's body. In exemplary embodiments, a composition comprising a CLPTM1L-targeting agent as provided herein is administered to a subject having a diagnosis of lung cancer or a pre-cancerous lesion, where the composition is administered orally or intravenously. Alternatively, a composition comprising a CLPTM1L-targeting agent can be administered locally to an intended area of treatment. For example, a composition comprising a CLPTM1L-targeting agent can be administered by local injection during surgery.

Compositions can be administered to a subject in need thereof in dosage unit form where each discrete dosage unit contains a predetermined quantity of an active ingredient or compound that was calculated to elicit a desirable therapeutic effect when administered with, in some cases, a pharmaceutically acceptable carrier.

A therapeutically effective dose relates to the amount of a compound which is sufficient to improve the symptoms, for example a treatment, healing, prevention or improvement of such conditions. In exemplary embodiments, a therapeutically effective amount or dose is an amount such that free antibody is present in the blood. For dosage determinations, it can be advantageous to assess toxicity and therapeutic efficacy of a compound in cell cultures or in experimental animals. For example, the $LD_{50}$ (i.e., the dose lethal to 50% of the population) and $ED_{50}$ (i.e., the dose therapeutically effective in 50% of the population) can be determined. From these calculations, dosage ranges for use in humans can be formulated. Dosage ranges can vary depending on factors such as mode of administration. A therapeutically effective amount of a pharmaceutical composition provided herein can range from about 0.001 to 100 mg of antibody per kg body weight of the subject (e.g., about 0.01 to 100 mg/kg body weight; about 0.1 to 40 mg/kg body weight; about 1 to 20 mg/kg body weight).

In some cases, an appropriate dose for a monoclonal antibody can be from 0.005 mg/kg up to a maximum tolerated dose. In some cases, an appropriate dose of a pharmaceutical composition as provided herein can be determined according to body surface area of a subject, calculated using the subject's height and weight, to whom the composition will be administered. In such cases, a dose can be provided as a particular amount of the composition per $m^2$ (e.g., mg/$m^2$). In some cases, an appropriate dose can be between approximately 10 mg/$m^2$ and approximately 40 mg/$m^2$ of a monoclonal antibody. When converted to milligrams (mg) per kilogram (kg) of a subject's body weight, a dose of 15 mg/$m^2$ is the same as about 0.4 mg/kg. See Freireich et al., *Cancer Chemotherapy Rep.* 50(4):219-244 (1966). Additional information about dosage calculation can be found in Center for Drug Evaluation and Research, Center for Biologics Evaluation and Research (2002), *Estimating the safe starting dose in clinical trials for therapeutics in adult healthy volunteers*, U.S. Food and Drug Administration, Rockville, Md., USA.

It will be understood that mass of pharmaceutical composition comprising a monoclonal antibody as provided herein can refer to mass of the antibody plus a delivery agent or pharmaceutically acceptable carrier, if applicable. In some cases, dosages and dosage ranges appropriate for a composition provided herein can be determined using pharmacokinetic data (i.e., drug metabolism and clearance). As used herein, "pharmacokinetics" refers to the process by which a drug or pharmaceutical composition is absorbed, distributed, metabolized, and excreted from the body.

Clinicians, physicians, and other health care professionals can administer a composition to a subject in need thereof according to a method provided herein by a physician or other health professional. In some cases, a single administration of the composition may be sufficient. In other cases, more than one administration of the composition is performed at various intervals (e.g., once per week, twice per week, daily, monthly) or according to any other appropriate treatment regimen. The duration of treatment can be a single dose or periodic multiple doses for as long as administration of a composition provided herein is tolerated by the subject.

Any appropriate method can be practiced to determine, detect, or monitor a subject's response to treatment according to a method provided herein. As used herein, "determining a subject's response to treatment" refers to the assessment of the results of a therapy in a subject in response to administration of a composition provided herein or to treatment according to a method provided herein. For example, a subject's condition can be monitored continuously or evaluated at appropriate time intervals (e.g., at regular or irregular time points) to detect and/or monitor any changes in disease progression (e.g., change in tumor size) as an indicator of the subject's response to a composition comprising an RNAi-inducing construct targeted to CLPTM1L. In some cases, tumors can be measured to detect or monitor any change in, for example, tumor size or tumor growth rate (e.g., tumor expansion or shrinkage, inhibited or accelerated tumor growth rate). For example, detection methods such as computed tomography (CT), magnetic resonance imaging (MRI) scanning, and x-ray (e.g., chest x-ray) can be used. In some cases, ultrasound examinations can be used to detect and measure tumor regression or to detect progression of lesions. In other cases, evaluation of a tumor or pre-neoplastic lesion can involve cytology or histology of, for example, biopsy samples. For solid tumors, evaluation of a subject's response to treatment as provided herein can include assessing RECIST ("Response Evaluation Criteria in Solid Tumors"). RECIST criteria can be used to evaluate a subject's response to the therapy used to treat their disease or condition. See, for review, Therasse et al., *J. Natl. Cancer Inst.* 92:205-16, 2000.

In some cases, biomarkers (e.g., mRNA, protein) can be used to detect or monitor the efficacy of a treatment or prevention method described herein. In an exemplary embodiment, use of a biomarker can comprises a) administering a composition provided herein; b) determining the levels of a biomarker according to the present invention in one or more biological samples taken from the subject at different time points (before, during and/or after administration); and c) comparing the determinations made for the biological samples obtained during a particular phase of treatment and comparing them to controls or to levels determined for the subject's samples obtained at different phases of treatment. For bone and blood tumors, evaluation using biomarkers can include detecting or monitoring expression levels for one or more tumor markers and assessing hematologic indicators including, for example, mean platelet volume, platelet counts, leukocyte counts, and hemoglobin level. Other indicators or "efficacy markers" of a positive outcome following administration of a composition comprising a CLPTM1L-specific agent according to a method provided herein can include (1) reduced CLPTM1L transcript and/or protein levels in tumors or target tissues and (2) reduced phosphorylated Akt or Bcl-xL protein levels in tumors or target tissues. These efficacy markers can be determined by biopsy, aspirate, or lavage followed by, in an exemplary embodiment, an appropriate diagnostic test such as PCR, Western blotting, immunohistochemistry using specific antibodies. A positive result for any of the outcome criteria or evaluation methods described herein is indicative of the method's efficacy for treating or preventing the subject's disease or condition.

Indicators of a positive response to administration of a composition comprising a CLPTM1L-targeting agent according to a method provided herein can include, for example, a significant decrease in CLPTM1L transcript and/or CLPTM1L protein levels in tumors or target tissues relative to pre-treatment levels or to untreated samples (e.g., expression reduced to approximately 60%-80% of expression in a control sample). In some cases, an indicator of a positive response to administration of a composition comprising a CLPTM1L-targeting agent can be significantly reduced levels of phosphorylated Akt and/or Bcl-xL proteins in tumors or target tissues relative to pre-treatment levels or to untreated samples or a significant increase in apoptosis in tumors or target tissues relative to pre-treatment levels or to untreated samples. According to RECIST criteria, a partial response to treatment can be indicated by at least a 30% decrease in the sum of the longest diameter of a target lesions, taking as reference the baseline sum longest diameter, and a complete or substantially complete response to treatment can be indicated by the complete or nearly complete disappearance of all target lesions relative to measurements obtained for the subject prior to treatment (i.e., baseline measurement) or relative to a control or a comparative decrease in disease progression. In some cases, response to treatment is evaluated relative to one or more subjects who were not administered a composition described herein. Other parameters for evaluating a subject's response to treatment according to a method provided herein include detecting a comparative decrease in metastatic growth; detecting any improvement in RECIST criteria for solid tumors; documenting short-term or long-term survival; documenting disease-free survival; detecting increased or decreased expression of tumor markers; detecting hematologic changes for blood and bone cancers; detecting or monitoring positive or negative responses to radiotherapy and/or chemotherapy; and detecting an increase or decrease in recurrence of the treated disease or condition. In some cases, a subject treated according to a method provided herein may exhibit signs of stable disease, where there is neither sufficient shrinkage to qualify for partial response nor sufficient increase to qualify for progressive disease, taking as reference the smallest sum longest diameter since the treatment started (Therasse et al., supra).

The determination of the response of a subject to a specific therapy can be determined using any assessment criterion used in oncology and known by persons skilled in the art. Assessment parameters useful for describing progression of a disease include: disease-free progression which, as used herein, describes the ratio of subjects in complete remission who have not had disease relapse during the time period under study; objective response, which, as used in the present invention, describes the ratio of subjects treated in whom a complete or partial response is observed; tumor control, which, as used in the present invention, relates to the ratio of people treated in whom a complete response, partial response, minor response or stable disease months is observed; progression-free survival which, as used herein, is defined as the time from the beginning of the treatment until the first measurement of cancer growth. In a preferred embodiment, the response of a subject is determined by means of a parameter selected from time to progression and survival. In an exemplary embodiment, a subject's response to a treatment or preventative method provided herein should be statistically significant. The determination of whether a response is statistically significant can be carried out using statistical evaluation tools such as confidence intervals, determination of the p value, Student's t-test, Mann-Whitney test, etc. Preferred confidence intervals are at least 50%, at least 60%, at least 70%, at least 80%, at least 90%, at least 95%. Preferably, p values are 0.2, 0.1, or 0.05.

While the subject is being treated, the health of the subject may be monitored by measuring one or more of the relevant indices at predetermined times during a 24-hour period. All aspects of the treatment, including supplements, amounts, times of administration and formulation, can be optimized based on the results of such monitoring. A patient can be periodically reevaluated to determine the extent of improvement by measuring the same parameters. For example, a first such reevaluation can occur at the end of an appropriate length of time (e.g., about 2 weeks, about 4 weeks, about 8 weeks, or more) following the onset of therapy, and subsequent reevaluations can occur at appropriate intervals (e.g., every four to eight weeks during therapy and then every 3, 6, 9, or more months) thereafter.

The articles "a" and "an" are used herein to refer to one or to more than one (i.e., to at least one) of the grammatical object of the article. By way of example, "an antibody" means one antibody or more than one antibody. As such, the terms "a" (or "an"), "one or more," and "at least one" are used interchangeably herein.

While the present invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents and alternatives falling within the spirit and scope of the invention as defined by the appended claims.

The invention will be more fully understood upon consideration of the following non-limiting Examples.

EXAMPLES

Example 1—Structural Analysis of CLPTM1L

Figure 2:
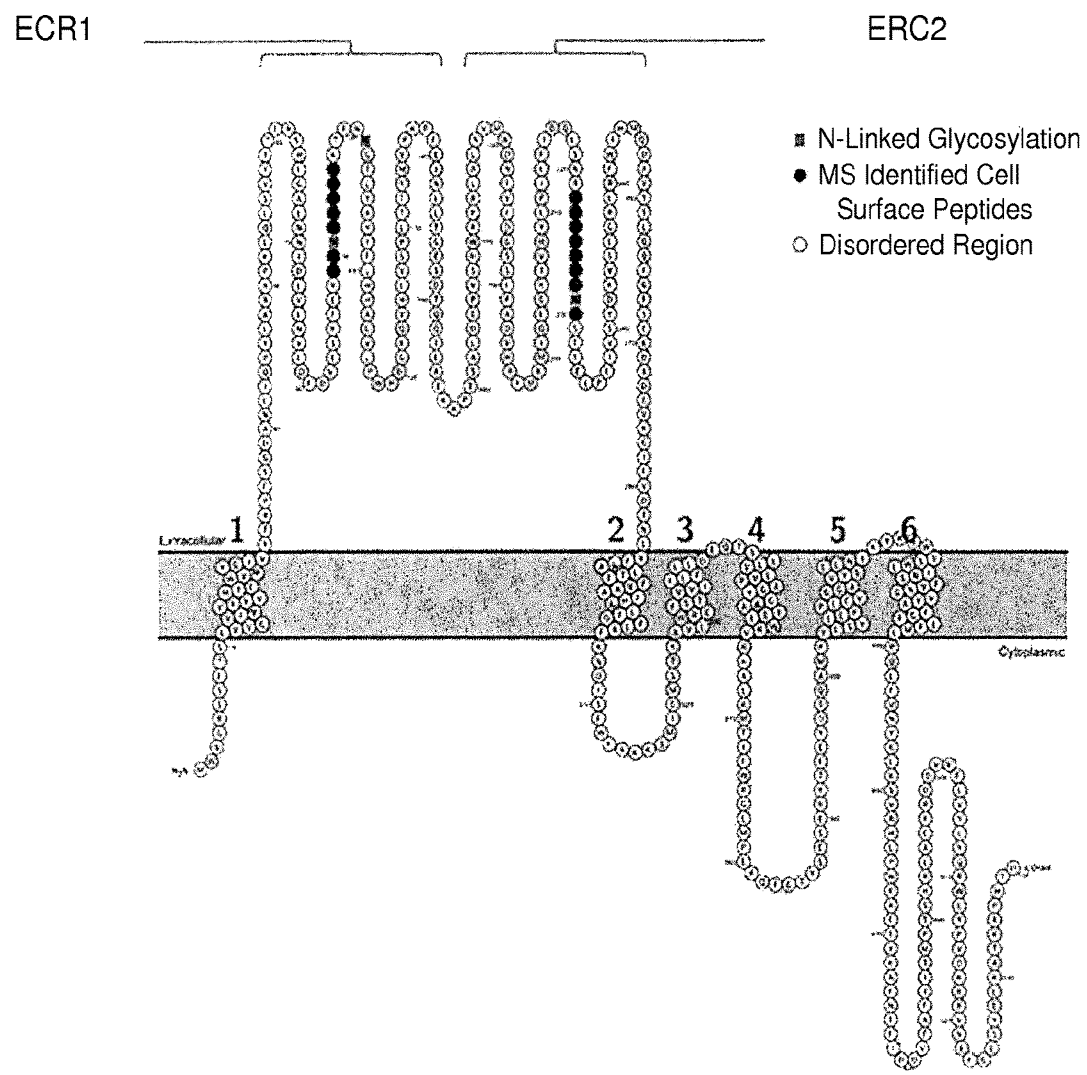
FIG. 2 presents (A) a summary of CLPTM1L predicted structure including orientation of the human sequence of CLPTM1L within the plasma membrane, two extracellular globular domains (ECR1 and ECR2), the interstitial disordered region, transmembrane regions, and identified glycosylated cell surface peptides (in blue) and predicted sites N-glycosylation sites (green). Monoclonal antibodies generated against CLPTM1L peptides targeting each ECR are indicated in parentheses. Image was generated using the Protter application (Omasits et al., Bioinformatics 30(6): 884-6 (2014)). (B) A splicing variant of CLPTM1L, lacking extracellular region 1 and some transmembrane domains changing the predicted structure. The expression pattern of this isoform is not known.
Figure 2:
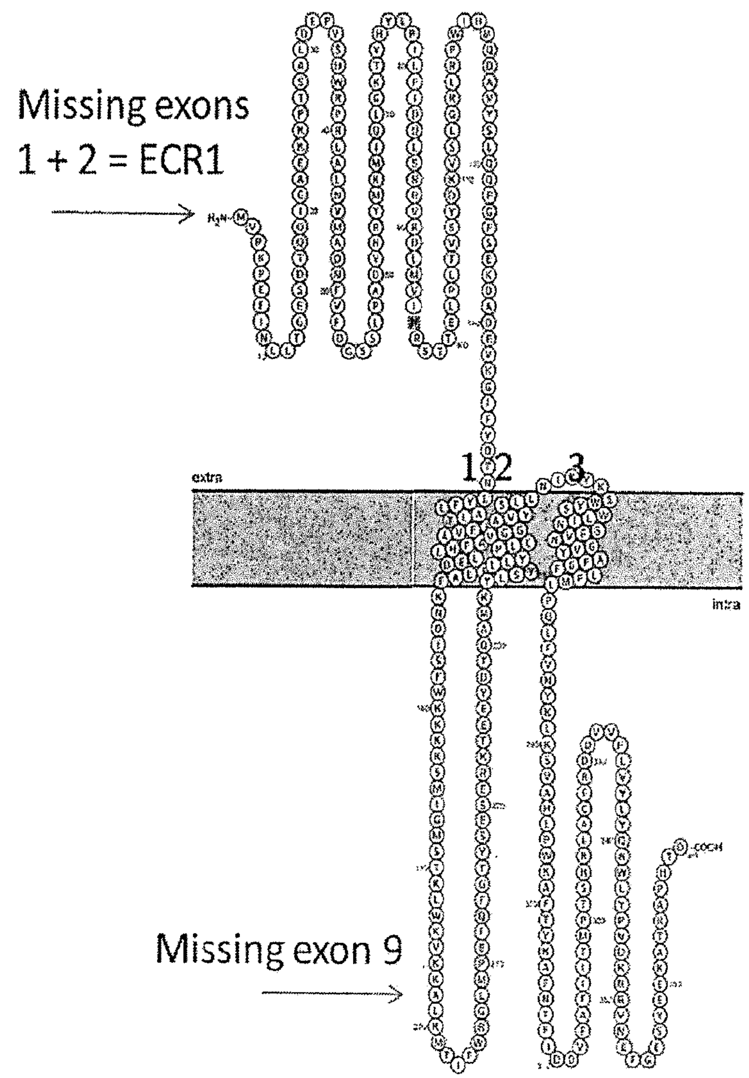

We generated a basic structural model of CLPTM1L that includes six transmembrane domains, extracellular globular domains (ECR1 and ECR2), the disordered region, and N-glycosylated cell-surface peptides identified by mass spectrometry (FIG. 2A). There is a putative alternatively spliced isoform of CLPTM1L lacking ECR1 and exons 1, 2, and 9 (FIG. 2B). Glycosylated (N-linked) amino acid residues are predicted at positions 91, 101, and 229 of the human CLPTM1L protein sequence (SEQ ID NO:2). Mass spectrometry evidence of glycosylation has been reported for amino acid residue 91 of human CLPTM1L (data not shown) and for residue 229 (Chen et al., *J Proteome Res.* 2009; 8:651-61). For a plasma membrane protein, this is highly indicative of extracellular orientation of the glycosylated region. It is predicted that this extracellular region comprises two separate globular domains separated by a small disordered region (amino acid residues 142-162) within the larger extracellular region (FIGS. 1A-1B).

Although our analysis of CLPTM1L suggested the possibility of plasma membrane localization and cell surface exposure, subcellular localization of CLPTM1L had not been well studied and plasma membrane localization was not previously reported. One study suggested that CLPTM1L may be localized to mitochondria. See Ni et al., *PLoS One* 7:e52598, 2012. The potential for CLPTM1L exposure at the surface of tumor cells has significant relevance to the ability to target this protein with exogenous agents.

Figure 3:
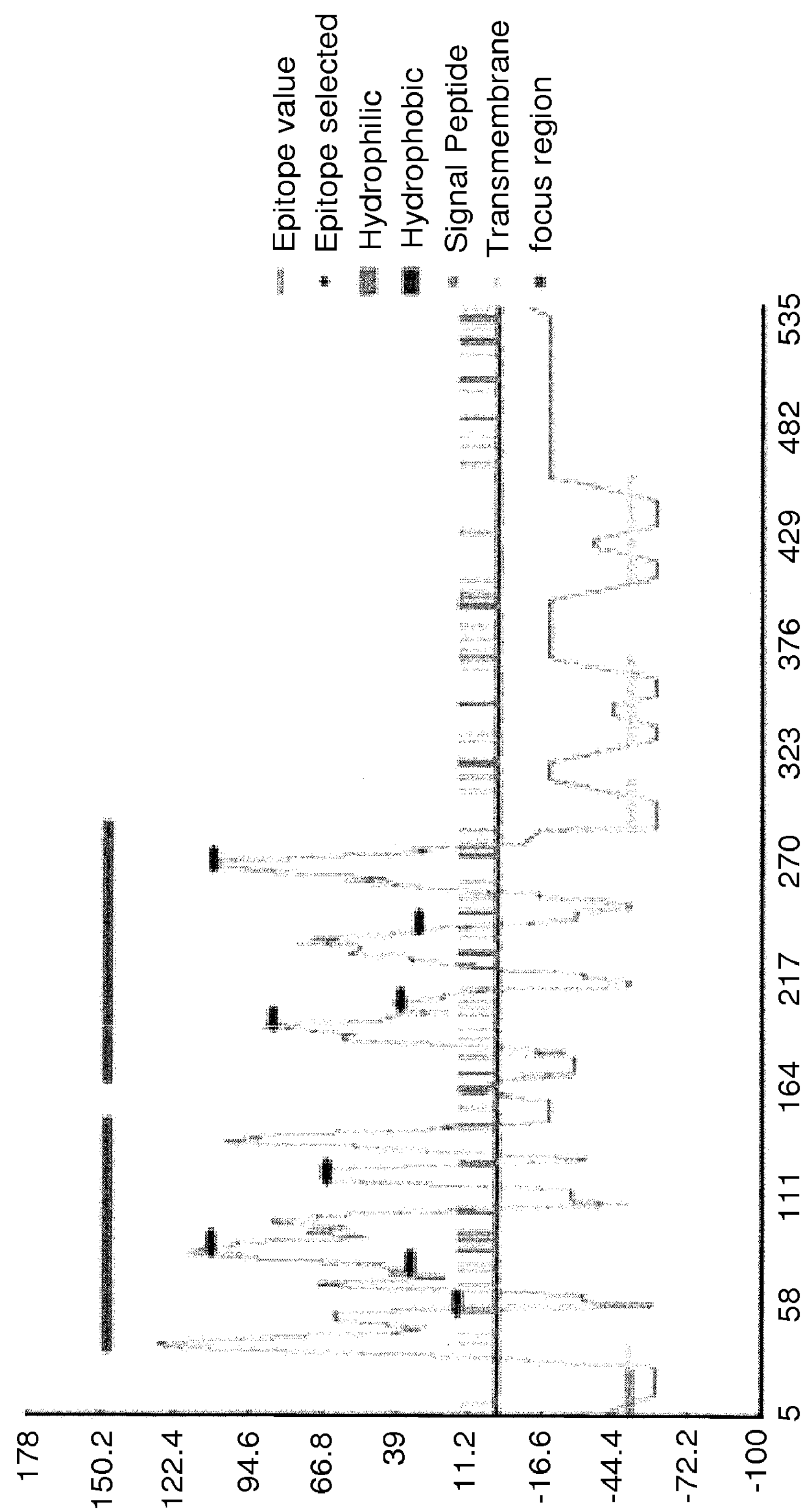
FIG. 3 depicts selection of epitopes to raise monoclonal antibodies specific for human CLPTM1L protein. The focus region for monoclonal antibody design included the ordered regions of the predicted extracellular domain. Glycosylation sites were excluded.

Since monoclonal antibodies are definable, consistent, reproducible, and capable of being manipulated, we contracted the production of a panel of monoclonal antibodies targeting the human CLPTM1L protein. Design of peptide epitopes against which to raise monoclonal antibodies took several factors into consideration. We designed the epitopes to reside within the cell surface exposed globular domains of CLPTM1L (residues 32-284, avoiding glycosylation sites (91, 101, 229), avoiding the disordered region (141-162), and prioritizing amino acid residues scoring highly on the basis of hydrophilicity, folding potential, and antigen presentation. Eight epitopes, each 11 amino acids in length, were selected for monoclonal antibody production (FIG. 3; see also shaded boxes of Table 1). While polyclonal antibodies may be generated against peptides of 8-22 amino acids, epitopes of 9-11 amino acids are typically chosen for specific monoclonal antibody production. Other potential epitopes selected bases on similar parameters are presented in the unshaded boxes of Table 1.

Figure 4:
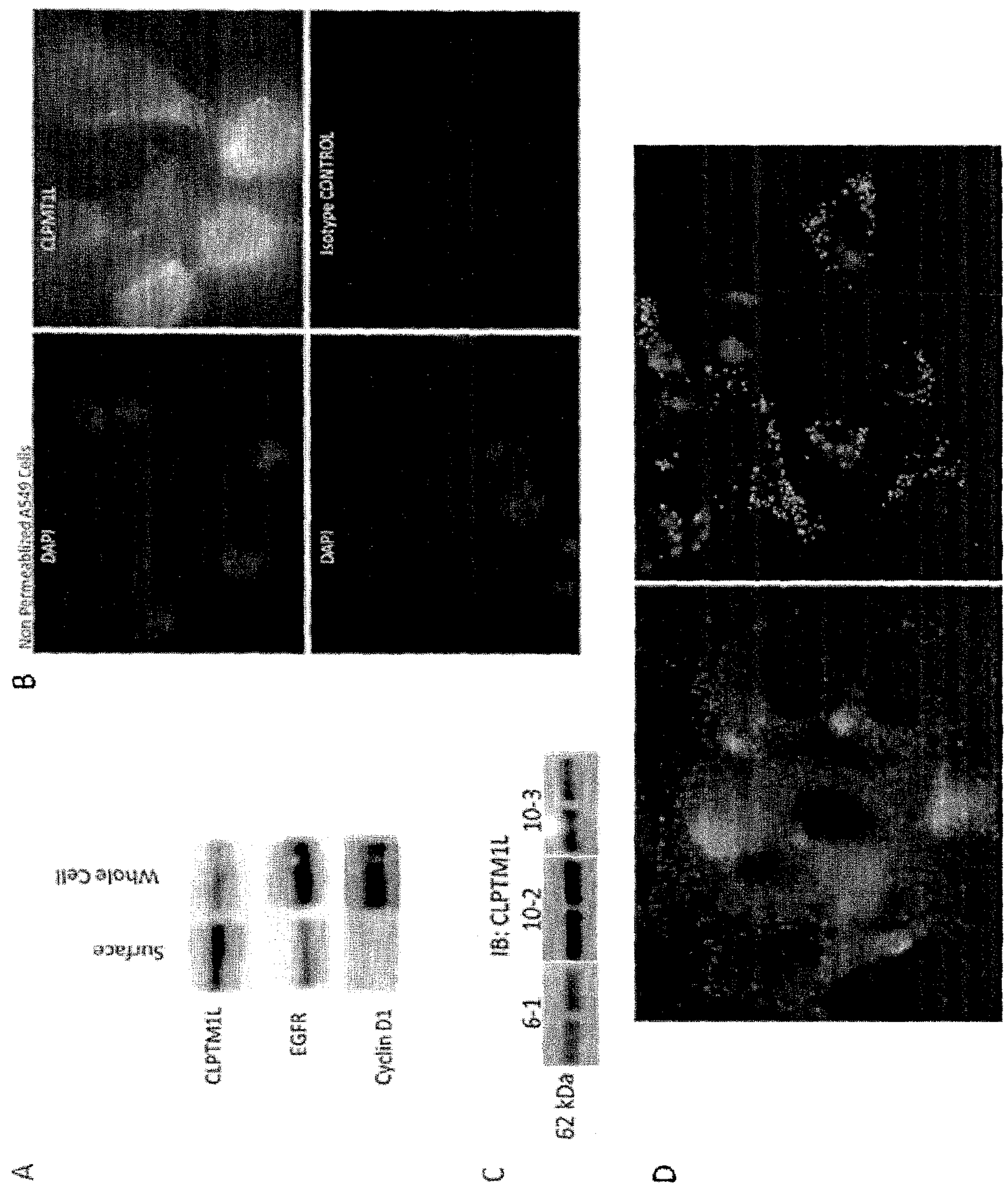
FIG. 4 demonstrates CLPTM1L localization. (A) Western blotting of cell surface and whole cell protein lysates for CLPTM1L, transmembrane receptor EGFR and nuclear protein Cyclin D1. Monoclonal antibodies 6-1, 10-2, and 10-3 were used for western blotting. (B) Immunofluorescent staining of non-permeablized A549 lung tumor cells using DAPI dye to stain cell nuclei and polyclonal antibody to the predicted extracellular N-terminus of human CLPTM1L followed by a secondary FITC conjugated antibody to detect CLPTM1L. A non-specific antibody was used as a control. Staining indicates punctuate plasma membrane localization of the protein. (C) Western blotting for CLPTM1L in H838 cells with monoclonal antibodies. (D) Immunofluorescent staining of non-permeabilized A549 cells with monoclonal CLPTM1L antibodies 6-1 (1000×) and 10-2 (400×). Monoclonal antibodies 6-1 and 10-2 were used for immunofluorescence.

To confirm the localization of CLPTM1L at the surface of tumor cells, we isolated cell-surface proteins from A549 human lung tumor cells by biotinylation and extraction with a streptavidin resin. Western analysis of whole cell and cell-surface lysates demonstrated a prevalence of CLPTM1L at the cell-surface (FIG. 4A). EGFR, used as a cell-surface localized control, was detected at the cell-surface at a lesser intensity than CLPTM1L relative to whole cell lysate signal. Cyclin D1, used as a nuclear protein control, was not detected at the cell surface. Immunofluorescence staining of non-permeabilized A549 cells for CLPTM1L revealed a punctate cell-surface staining pattern (FIG. 4B).

Our panel of monoclonal antibodies targeting the extracellular globular domains of CLPTM1L was tested for detection of CLPTM1L and immunofluorescent labeling of surface CLPTM1L. All antibodies strongly detected the 62-kilodalton CLPTM1L protein by western blot (FIG. 4C; some data not shown). All antibodies resulted in a cell-surface staining pattern when used for immunofluorescence on non-permeabilized A549 cells, with antibodies targeting ECR2 exhibiting a more distinct punctate staining (FIG. 4D; some data not shown).

Example 2—In Vitro Analysis of CLPTM1L Monoclonal Antibodies

Figure 5:
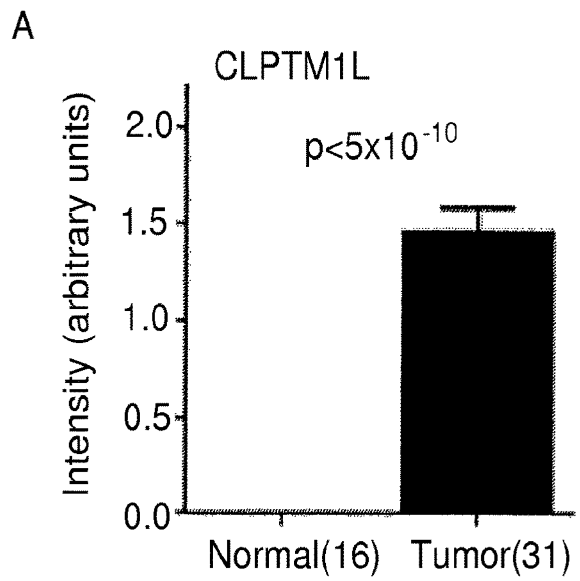
FIG. 5 presents graphs and images demonstrating that CLPTM1L expression is increased in pancreatic tumor tissue over normal pancreatic ductal epithelia and that higher expression is correlated with poor survival. (A) Immunohistochemical scoring of staining with antibody specific to CLPTM1L in pancreatic tumor vs. normal ductal epithelial tissues in 31 patients. (B) Kaplan-Meier survival curves stratified into tertiles of CLPTM1L expression. (C) Representative staining of tumor.
Figure 5:
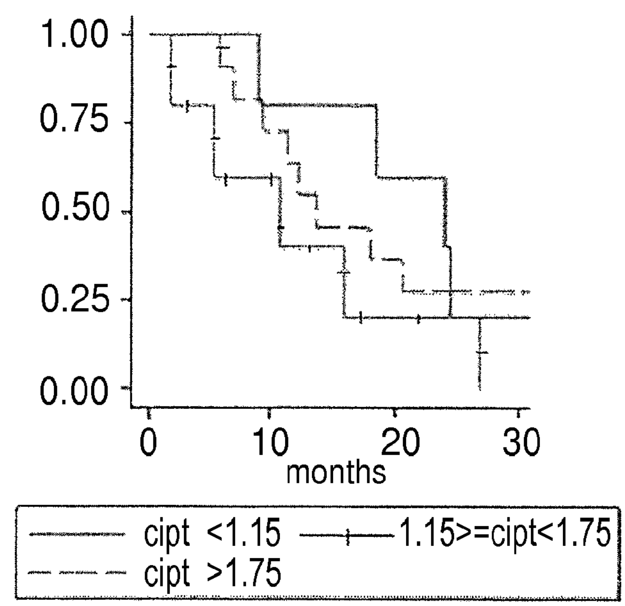
Figure 5:
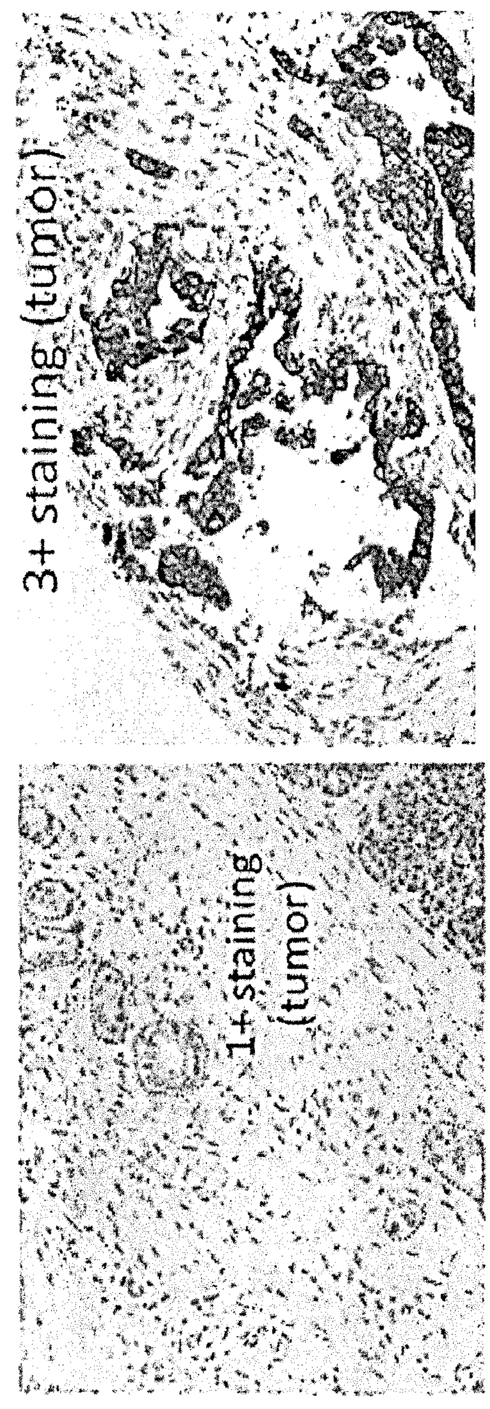

To determine if CLPTM1L expression was associated with K-Ras driven pancreatic cancer treated with adjuvant therapy, we utilized available pancreatic tissue microarrays on 31 patients using matched survival data. Staining intensity of tumors that were subjected CLPTM1L immunohistochemistry (IHC) were scored by three pathologists and the scores averaged. Staining was uniformly negative in normal ductal epithelia, while positive in 94% (29/31) of tumor cells ($r=0.78$, $p<5\times10{-}10$) (FIG. 5A). Tumors were scored as negative (0), weak (+1), moderate (+2) or strong (+3). Independent scores were averaged. Tumors had an average score of 1.46 while that of normal ductal epithelial was 0 ($p<0.05$). Tumors expressing low levels of CLPTM1L as defined by an average score of 1.15 or less were associated with increased survival, while patients with higher expression had shorter survival times. Patients exhibiting low CLPTM1L expression in tumor tissues had a median survival of 24 months, while patients with medium and high CLPTM1L expression in tumor tissues had a median survival of 11 and 14 months respectively (FIG. 5B). Representative tissues stained with CLPTM1L antibody are shown in FIG. 5C.

Figure 6:
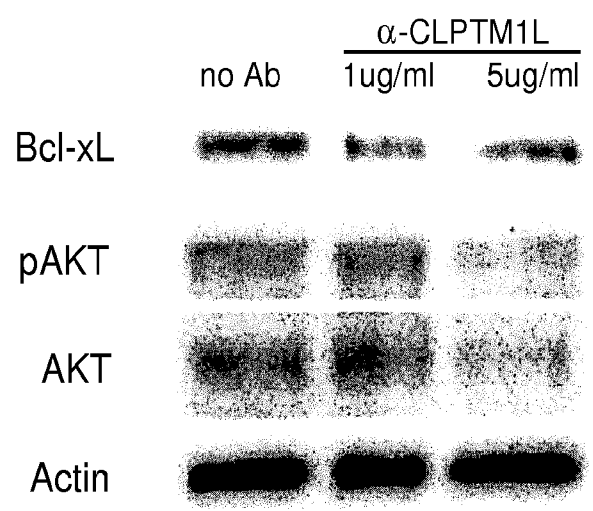
FIG. 6 demonstrates that targeting CLPTM1L in tumor cells modulates Bcl-xL and Akt survival signaling and sensitizes cells to killing with cisplatin. (A) Treating A549 cells with polyclonal anti-CLP antibody (1:1000=1 μg/mL) reduced accumulation of anti-apoptotic molecules Bcl-xL and total Akt. (B) Anti-CLPTM1L significantly increased sensitivity to killing upon cisplatin treatment for 24 hours ($p<0.05$). (C) Treatment with monoclonal anti-CLP (10-2) increased sensitivity of pancreatic adenocarcinoma cells to killing by gemcitabine (500 μM for 72 hours). (D) Treatment of pancreatic adenocarcinoma cells with monoclonal anti-CLP (10-2) reduced accumulation of phosphorylated Akt.
Figure 6:
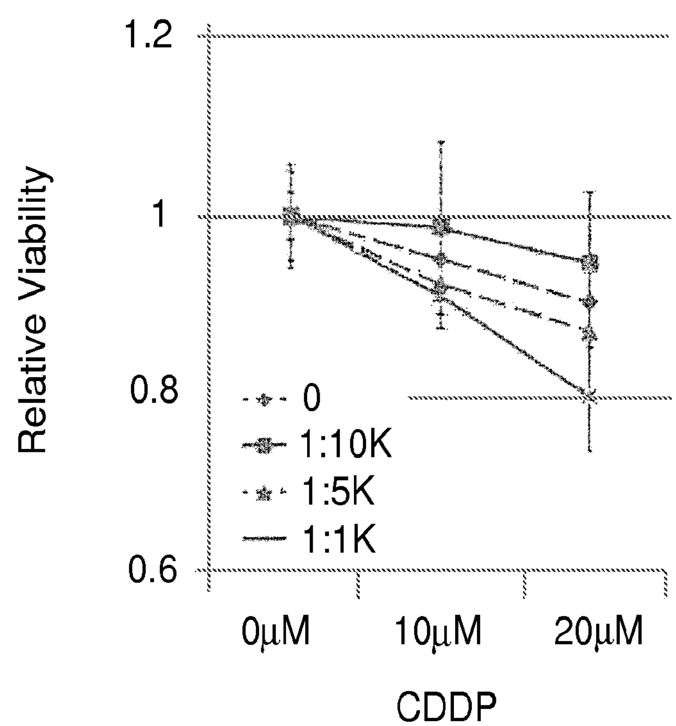
Figure 6:
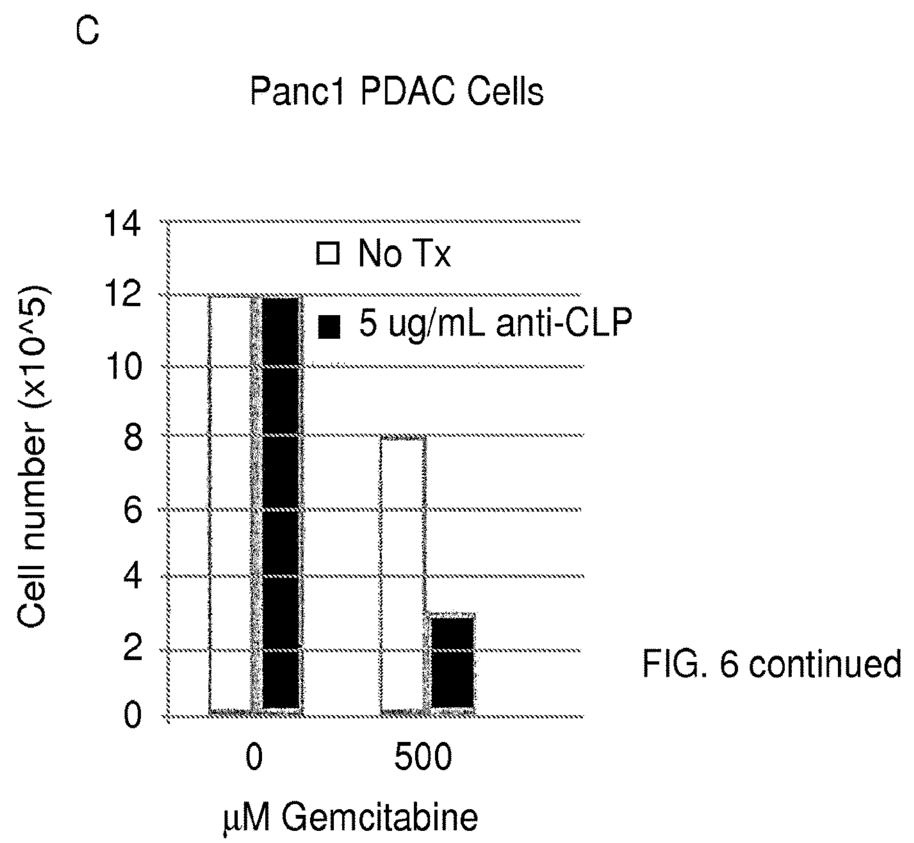
Figure 6:
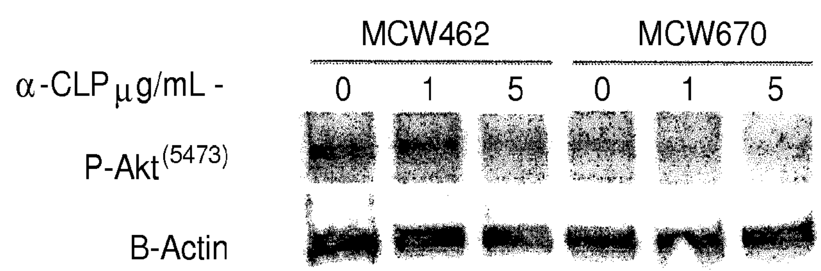
Figure 7:
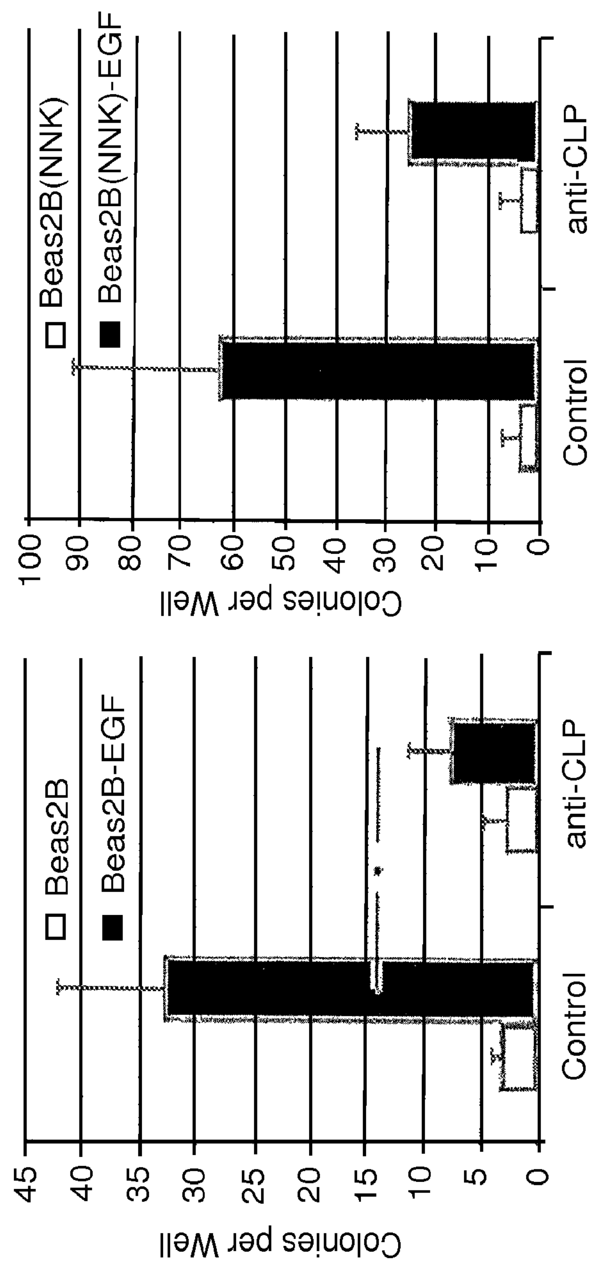
FIG. 7 presents images and graphs demonstrating that treatment with anti-CLP antibody (Ab) inhibits anchorage-independent growth of human lung tumor and bronchial epithelial cells in vitro. Anchorage-independent growth of human lung tumor cells, as measured by colony formation in 0.4% top agar over a 0.8% bottom agar layer, was inhibited by 55%-65% by anti-CLPTM1L treatment compared to solvent control treated cells ($p<0.05$). Treatments were administered one day after plating and again one week later. EGF treatment induced anchorage independent growth in Beas2B human bronchial epithelial cells, which was inhibited by 76% upon treatment with anti-CLP Ab.
Figure 7:
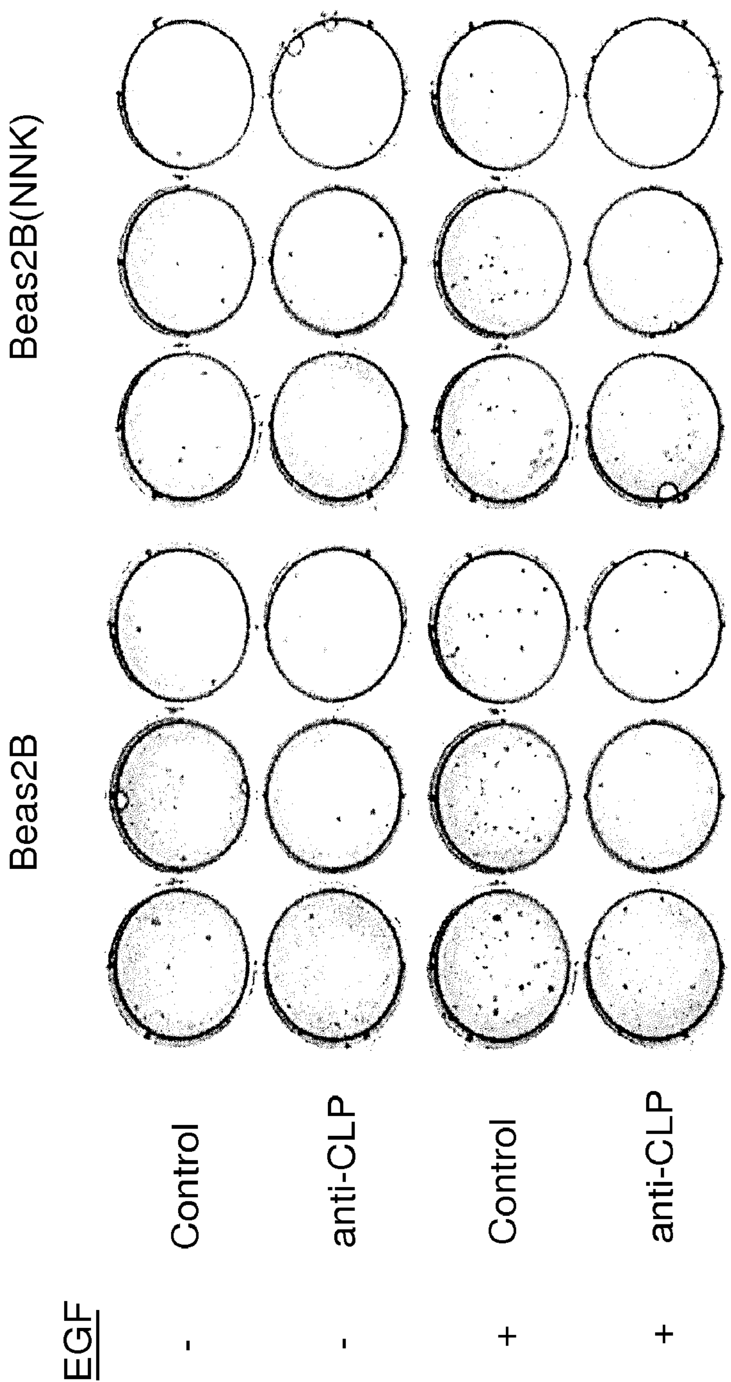

We previously demonstrated that targeting CLPTM1L in tumor cells modulates Bcl-xL and Akt survival signaling and sensitizes cells to killing with cisplatin. Polyclonal antibody raised against amino acid residues 18-307 of human CLPTM1L was applied to A549 human lung tumor cells at concentrations of 0, 1, and 5 μg/mL. After culture for 48 hours with polyclonal antibody treatment, Western blotting was conducted for Bcl-xL, total Akt1, and phospho-Akt1. Dose dependent decreases in the accumulation of both Bcl-xL and Akt1 with anti-CLPTM1L treatment were observed (FIG. 6A). To determine the effect of treatment with polyclonal antibody on sensitivity to cisplatin, cells were treated with dilutions of anti-CLPTM1L from 0.01 to 1 μg/mL for 24 hours. Cells were then exposed to cisplatin at 0, 10, and 20 μM concentrations for 48 hours. Treatment with anti-CLPTM1L resulted in a decrease in cell viability following cisplatin treatment that was dependent on the dose of antibody (FIG. 6B). These results demonstrate sensitization to cisplatin killing using the antibody.

Treatment with monoclonal anti-CLP (10-2) increased sensitivity of pancreatic adenocarcinoma cells to killing by gemcitabine (500 μM for 72 hours) (FIG. 6C) and also reduced accumulation of phosphorylated Akt (FIG. 6D).

In addition, treatment of A549 and H838 human lung tumor cells with our panel of monoclonal antibodies resulted in depletion of Bcl-xL and Akt phosphorylation with a range of efficacies. Western analysis revealed that treatment with antibodies targeting epitopes 6 and 10 resulted in dose dependent decreases in Bcl-xL and phospho-Akt1 accumulation. Likewise, sensitization to cisplatin killing was accomplished by treatment of tumor cells with anti-CLPTM1L monoclonal antibodies. Monoclonal antibody raised against epitope 10 effectively inhibited anchorage independent growth of A549 cells. Among all monoclonal antibodies raised against the extracellular domains of CLPTM1L, only those raised against epitope 10 were effective in inhibiting anchorage independent tumor spheroid growth of H838 cells. A summary of these results for each antibody clone is given in FIG. 10.

Figure 8:
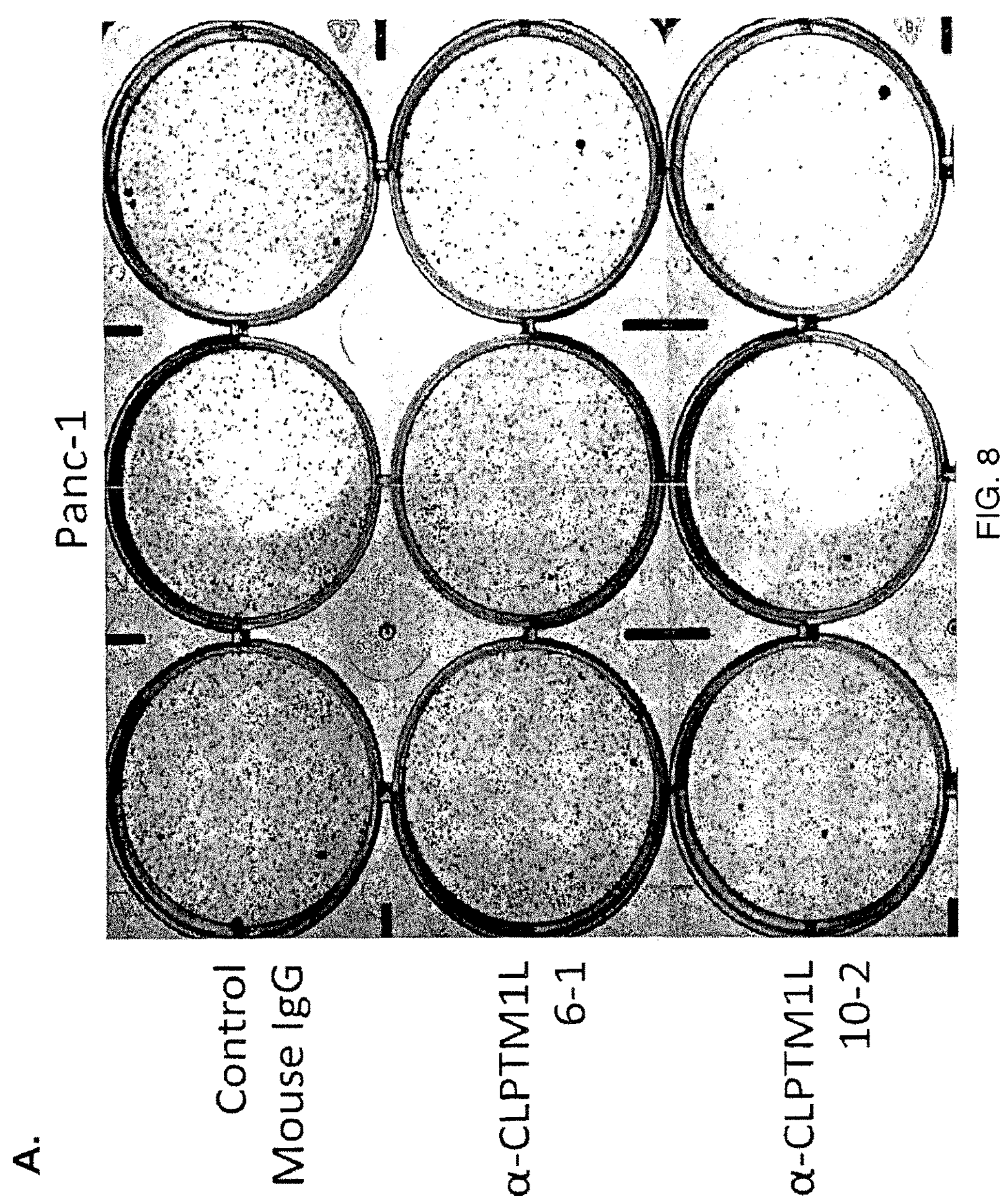
FIG. 8 demonstrates colony growth inhibition of pancreatic tumor cells by anti-CLPTM1L antibodies. (A) Panc-1 pancreatic tumor cells were plated on 6-well plates in triplicate at 1000 cells per well in DMEM/F12 w/10% FBS. After plating, the indicated antibodies were added to the culture media at 5 μg/mL. (B) Colonies per well were counted after 5 days in culture following fixation in methanol and staining with 0.5% crystal violet. **$p=0.005$.
Figure 8:
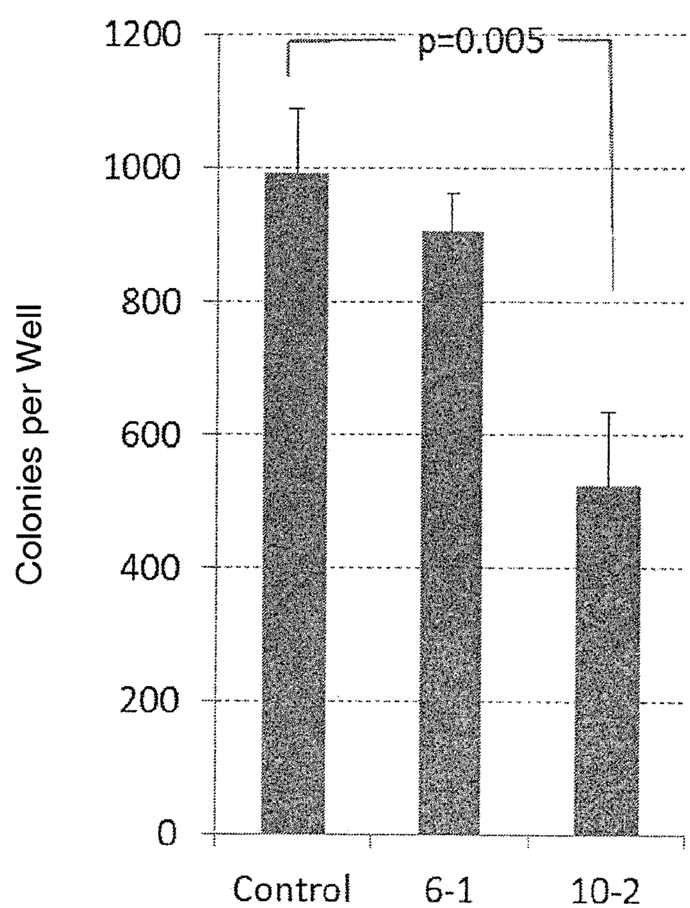

As shown in FIG. 8, we also discovered that treatment with monoclonal anti-CLPTM1L antibodies inhibited colony growth of pancreatic tumor cells. Panc1 pancreatic adenocarcinoma cells were plated at low density and treated with anti-CLPTM1L 6-1, 10-2, or control mouse IgG (FIGS. 8A-B). The number of resulting colonies after 5 days of growth was inhibited by up to 47% by anti-CLPTM1L treatment.

Figure 9:
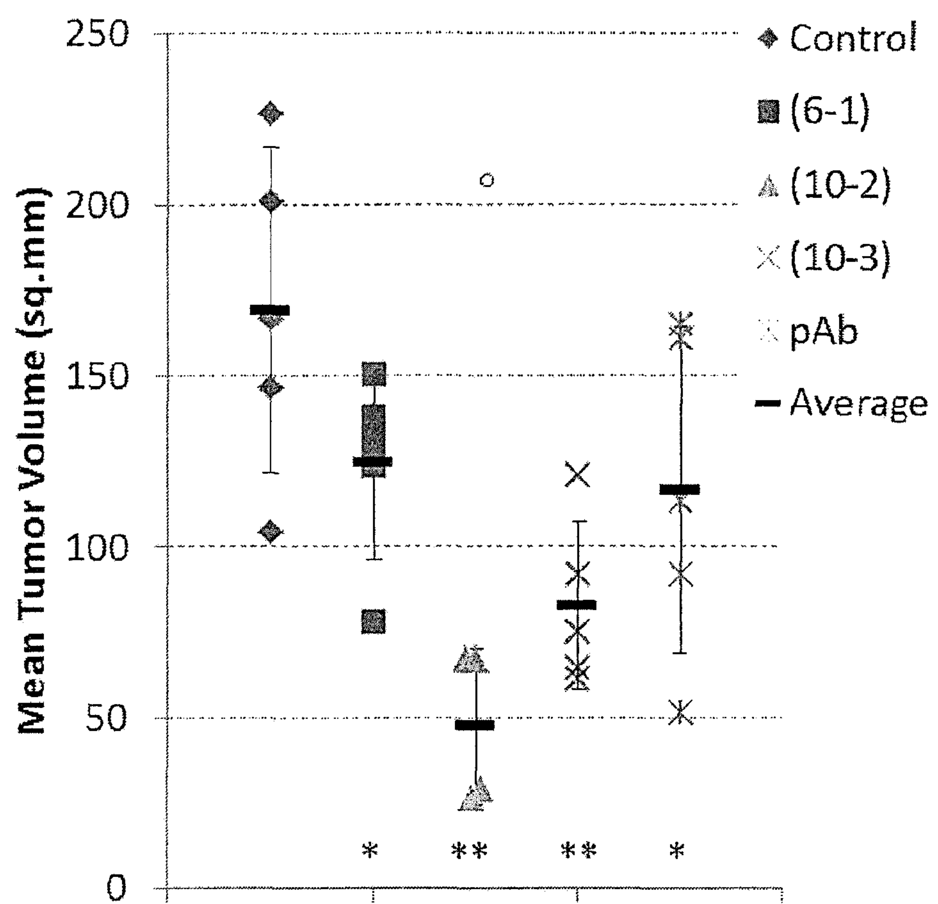
FIG. 9 presents xenograft models for inhibition of the growth of established human lung tumors. (A) Mean tumor volume in athymic nude mice injected subcutaneously with A549 tumor cells and treated with control ascites, polyclonal anti-CLPTM1L, or monoclonal anti-CLPTM1L clones after tumor establishment on days 0, 5, and 12. Error bars represent standard error of the mean. (B) Tumor volumes of individual tumors at day 17. Error bars represent standard deviations.*$p<0.05$, **$p<0.005$.
Figure 9:
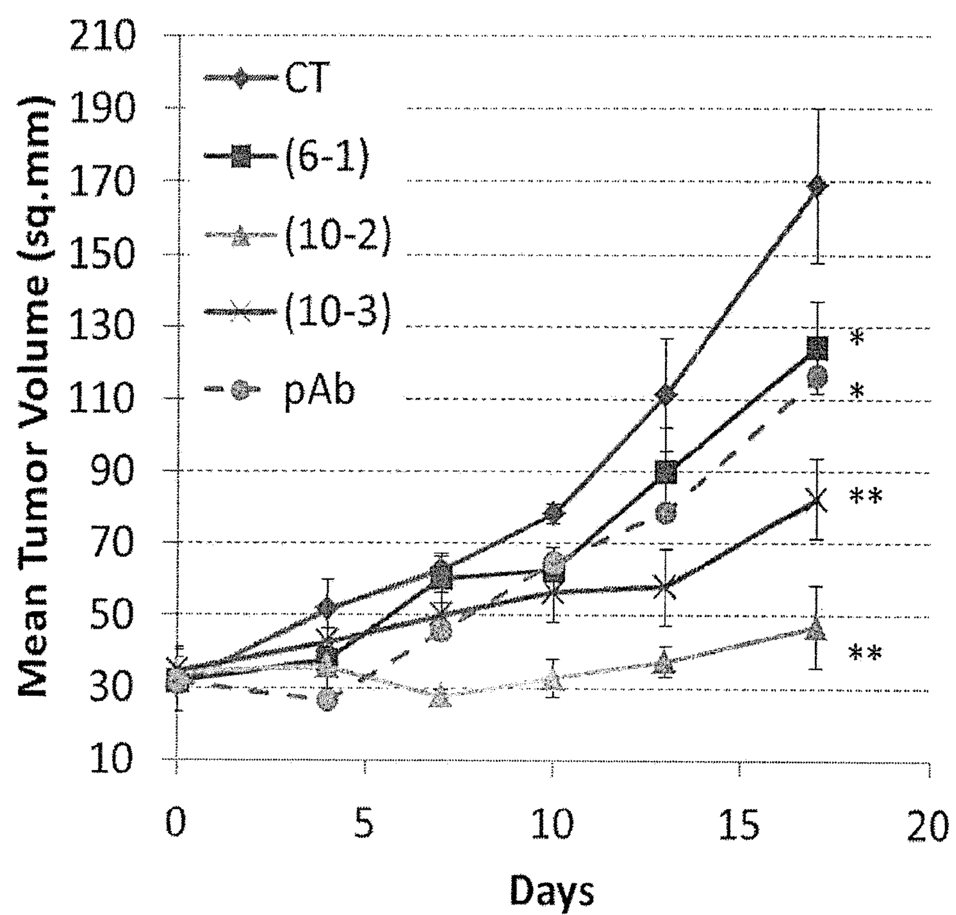

Example 3—Effect of CLPTM1L Monoclonal Antibodies on Human Lung Tumor Xenograft Model Monoclonal antibodies raised against epitope 6 in ECR1 (SEQ ID NO:6) and epitope 10 in ECR2 (SEQ ID NO:10) were evaluated in xenograft models for inhibition of the growth of established human lung tumor xenografts. A549 cell xenografts were established and mice were separated into groups of equal average tumor size and variance. Mice were treated intraperitoneally with 1 μL/g (estimated to be equivalent to 2-3 mg/kg of antibody) of the indicated monoclonal antibody clone or control ascites on days 0, 5, and 12 post-separation. One group was similarly treated with 1 mg/kg polyclonal antibody. Polyclonal antibody and monoclonal clone 6-1 modestly but significantly inhibited tumor growth over 17 days post-treatment (FIG. 9). Antibodies raised against epitope 10 (10-2 and 10-3) had a more robust and more significant inhibitory effect on tumor growth. Monoclonal clone 10-2 inhibited tumor growth by 88% ($p<0.005$).

The examples and data set forth above demonstrate that anti-CLPTM1L immunoglobulins are anti-tumor agents in vivo and in vitro. Furthermore, they describe specific epitopes expected to be efficacious in targeting the extracellular domains of CLPTM1L.

I claim:

1. A CLPTM1L-targeting agent, wherein the CLPTM1L-targeting agent is a monoclonal antibody specific for at least a portion of a CLPTM1L polypeptide and selected from anti-CLPTM1L monoclonal antibody clones 6-1 (ATCC PTA-125531), 10-2 (ATCC PTA-125532), and 10-3(ATCC PTA-125530).

2. A pharmaceutical composition comprising the CLPTM1L-targeting agent of claim 1 and a pharmaceutically acceptable carrier.

3. An article of manufacture comprising: (a) the pharmaceutical composition of claim 2, and (b) an insert providing instructions for treating a solid tumor in a human subject.

4. A method for treating a lung cancer comprising administering a therapeutically effective amount of a compound comprising a CLPTM1L-targeting agent to a subject in need thereof, wherein the CLPTM1L-targeting agent is a monoclonal antibody specific for at least a portion of a CLPTM1L polypeptide and selected from anti-CLPTM1L monoclonal antibody clones 6-1 (ATCC PTA-125531), 10-2 (ATCC PTA-125532), and 10-3 (ATCC PTA-125530), whereby the lung cancer is treated in the subject.

5. The method of claim 4, wherein the subject is a human.

6. The method of claim 4, wherein the lung cancer exhibits resistance to a chemotherapeutic agent.

7. The method of claim 6, wherein the chemotherapeutic agent is selected from the group consisting of cisplatin, gemcitabine, carboplatin, carmustine, methotrexate, fluorouracil, goserelin, leuprolide, tamoxifen, docetaxel, paclitaxel, aldesleukin, interleukin-2, etoposide (VP-16), interferon-alpha, tretinoin (ATRA), bleomycin, dactinomycin, daunorubicin, doxorubicin, mitomycin, vinblastine, and vincristine.

8. The method of claim 4, wherein the compound is administered with a pharmaceutically acceptable carrier.

* * * * *

UNITED STATES PATENT AND TRADEMARK OFFICE

CERTIFICATE OF CORRECTION

PATENT NO. : 10,266,586 B2
APPLICATION NO. : 15/111445
DATED : April 23, 2019
INVENTOR(S) : Michael A. James It is certified that error appears in the above-identified patent and that said Letters Patent is hereby corrected as shown below:

In the Specification

Column 12, Line 54, "at," should be --al.,--.

Column 23, Lines 38-39, "disease months" should be --disease ≥6 months--.

In the Claims

Column 81, Claim 4, Line 67, "istering a" should be --istering to a subject in need thereof a--.

Column 82, Claim 4, Lines 54-55, "agent to a subject in need thereof, wherein" should be --agent, wherein--.

Signed and Sealed this
Twenty-eighth Day of May, 2019

Andrei Iancu
*Director of the United States Patent and Trademark Office*